(12) United States Patent
Bandiera et al.

(10) Patent No.: US 9,012,487 B2
(45) Date of Patent: Apr. 21, 2015

(54) BICYCLO-PYRAZOLES ACTIVE AS KINASE INHIBITORS

(75) Inventors: Tiziano Bandiera, Gambolo (IT); Jay Aaron Bertrand, Villacortese (IT); Paolo Pevarello, Pavia (IT); Ettore Perrone, Boffalora S/Ticino (IT); Andrea Lombardi Borgia, Paullo (IT); Sten Christian Orrenius, Gallarate (IT); Mauro Angiolini, Gavirate (IT); Daniele Fancelli, Milan (IT)

(73) Assignee: Nerviano Medical Sciences S.r.l., Nerviano (MI) (IT)

( * ) Notice: Subject to any disclaimer, the term of this patent is extended or adjusted under 35 U.S.C. 154(b) by 648 days.

(21) Appl. No.: 12/281,602

(22) PCT Filed: Mar. 2, 2007

(86) PCT No.: PCT/EP2007/052024
§ 371 (c)(1),
(2), (4) Date: Oct. 15, 2008

(87) PCT Pub. No.: WO2007/099171
PCT Pub. Date: Sep. 7, 2007

(65) Prior Publication Data
US 2009/0136513 A1    May 28, 2009

Related U.S. Application Data

(60) Provisional application No. 60/778,898, filed on Mar. 3, 2006.

(51) Int. Cl.
| | | |
|---|---|---|
| C07D 487/04 | (2006.01) | |
| A61K 31/496 | (2006.01) | |
| A61K 31/5377 | (2006.01) | |
| A61K 31/4162 | (2006.01) | |

(52) U.S. Cl.
CPC .......... C07D 487/04 (2013.01); A61K 31/5377 (2013.01); A61K 31/4162 (2013.01); A61K 31/496 (2013.01)

(58) Field of Classification Search
CPC ............... C07D 487/04; A61K 31/496; A61K 31/5377; A61K 31/4162
USPC .......... 544/140, 371; 548/360.5; 514/254.06, 514/234.2, 407
See application file for complete search history.

(56) References Cited

U.S. PATENT DOCUMENTS 7,531,531 B2 * 5/2009 Fancelli et al. ............... 514/215
7,541,354 B2 * 6/2009 Fancelli et al. ............... 514/215

FOREIGN PATENT DOCUMENTS

| WO | WO 02/12242 A | 2/2002 |
| WO | WO 0212242 A2 * | 2/2002 |
| WO | WO 2004/056827 A | 7/2004 |

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*

* cited by examiner

*Primary Examiner* — Joseph Kosack
*Assistant Examiner* — Matthew Coughlin
(74) *Attorney, Agent, or Firm* — Scully, Scott, Murphy & Presser, P.C.

(57) ABSTRACT

A compound having formula (I): wherein: R, A, $R^1$ and $R^2$, are as defined in the specification, and pharmaceutical formulas thereof, and methods of use thereof, as Kinase inhibitors.

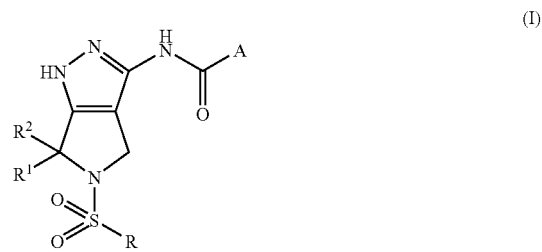

(I)

5 Claims, 2 Drawing Sheets

FIGURE 1

SEQ ID NO: 3

MGSPILGYWKIKGLVQPTRLLLEYLEEKYEEHLYERDEGDKWRNKKFELGLEFPNLPYYIDGDVK
LTQSMAIIRYIADKHNMLGGCPKERAEISMLEGAVLDIRYGVSRIAYSKDFETLKVDFLSKLPEMLK
MFEDRLCHKTYLNGDHVTHPDFMLYDALDVVLYMDPMCLDAFPKLVCFKKRIEAIPQIDKYLKSS
KYIAWPLQGWQATFGGGDHPPKSDLEVLFQGPGSRKRNNSRLGNGVLYASVNPEYFSAADVY
VPDEWEVAREKITMSRELGQGSFGMVYEGVAKGVVKDEPETRVAIKTVNEAASMRERIEFLNEA
SVMKEFNCHHVVRLLGVVSQGQPTLVIMELMTRGDLKSYLRSLRPEMENNPVLAPPSLSKMIQM
AGEIADGCANLNANKFVHRDLAARNCMVAEDFTVKIGDFGMTRDIYETDYYRKGGKGLLPVRW
MSPESLKDGVFTTYSDVWSFGVVLWEIATLAEQPYQGLSNEQVLRFVMEGGLLDKPDNCPDML
FELMRMCWQYNPKMRPSFLEIISSIKEEMEPGFREVSFYYSEENKLPEPEELDLEPENMESVPLD
PSASSSSLPLPDRHSGHKAENGPGPGVLVLRASFDERQPYAHMNGGRKNERALPLPQSSTC

BICYCLO-PYRAZOLES ACTIVE AS KINASE INHIBITORS

CROSS-REFERENCE TO RELATED APPLICATIONS

This application claims benefit of U.S. Provisional application No. 60/778,898, filed Mar. 3, 2006, the entire contents of which is incorporated herein by its reference.

BACKGROUND OF THE INVENTION

1. Field of the Invention

The present invention relates to certain bicyclic-pyrazole compounds, to pharmaceutical compositions thereof, and to the use of these bicyclic-pyrazole compounds or pharmaceutical compositions thereof in the treatment of certain diseases.

2. Discussion of the Background

The insulin-like growth factor 1 receptor (IGF-1R, IGF1R) is a member of the insulin receptor subfamily of RTKs. IGF-1R has a relatively ubiquitous pattern of tissue expression, and consists of two alpha chains, which are extracellular and contain ligand binding function, and two beta chains, which span the cell membrane and contain the intracellular kinase domains. The mature receptor consists of a disulphide-linked heterodimer of two pairs of alpha/beta subunits, resulting in an (alpha/beta)2 complex. IGF-1R is able to bind and be activated by the ligands insulin-like growth factor-1 and -2 (IGF-1 and IGF-2). Insulin will also activate IGF-1R, but only at supraphysiological concentrations (i.e. in the range of circa 100 nanoM-1 microM).

IGF-1 and IGF-2 are circulating growth factors which mediate many of the effects of Growth Hormone (GH), and which therefore have important roles in foetal and post-natal growth and metabolism. IGF-1R, like several other RTKs such as the EGF and PDGF receptor families, has potent mitogenic, anti-apoptotic and transforming activity in a wide range of cell types. Notably, it directly activates at least two major cell signaling pathways, the ras/MAPK pathway, through recruitment of SHC, and the PI-3 kinase/AKT (PKB) pathway, through recruitment and phosphorylation of the IRS adapter proteins.

There exist several lines of evidence suggesting that IGF-1R signaling can contribute to tumorigenesis, and that interfering with IGF-1R function represents a valid therapeutic option in cancer. IGF-1R signaling can promote tumorigenesis through multiple mechanisms. Aside from being mitogenic for most, if not all, cells which express IGF-1R promote cell survival and inhibit apoptosis through activation of the PI-3K/AKT and ras/MAPK, as well as other signaling pathways, depending on cellular context.

Various experimental strategies have demonstrated that interference with IGF-1R function can result in anti-tumor effects in a wide range of tumor cell types. Low molecular weight, selective inhibitors of IGF-1R kinase activity have also been described and these agents inhibit the in vitro and in vivo growth of a wide range of human tumor cells.

Since IGF-1R promotes cell proliferation, transformation, and protection from apoptosis in a wide range of cell types and in response to cooperation with diverse stimuli, it follows that inhibition of IGF-1R function might potentiate the effects of chemotherapeutic agents having diverse mechanisms of action. A blockade of IGF-1R function using the strategies described above, including selective IGF-1R kinase inhibitors, has been found to augment the in vitro, and/or in vivo activity of a wide range of agents including signal transduction inhibitors such as Gleevec, anti-EGFR and anti-HER2 blocking antibodies, cytotoxic agents such as adriamycin, doxorubicin, 5-FU, vinorelbine, and antihormonal therapy.

Aside from cancer, IGF-1R activity is also implicated in a wide range of pathophysiological processes in which inhibition of receptor activity could be expected to yield clinical benefit. These include, but are not limited to, acromegaly, conditions involving persistent inflammation and/or cell proliferation such as psoriasis and fibrotic lung disease, and benign prostatic hyperplasia. Reduction of IGF-1R signaling has also been associated with increased longevity in several animal models, potentially due to increased tolerance of oxidative stress, such as that which occurs during hyperoxia, and related settings could also be therapeutically targeted by inhibiting the receptor.

IGF-1R signaling provides angiogenic stimulus in many tissues, at least in part through stimulation of hypoxic responses, including upregulation of VEGF expression. Accordingly, systemic blockade of IGF-1R using a monoclonal antibody has been found to be an effective treatment in an animal model of diabetic retinopathy, a condition involving inappropriate VEGF expression. Similarly, IGF-1R function has also been strongly implicated in contributing to development of retinopathy of prematurity as well as in age-related macular degeneration. There is also evidence that IGF-1 contributes to vascular neointimal formation, and to atherosclerotic processes.

Thus, IGFs/IGF-1R play a significant role in tumorigenic processes in a wide range of human tumors, and inhibition of IGF-1R function through approaches that include inhibitors of IGF-1R kinase activity could be expected to yield therapeutic benefit, either alone or in combination with many agents. Such therapy could be extended to several other pathologies which involve inappropriate IGF-1R activity. Accordingly, there is a need for new compounds that can inhibit IGF-1R kinase activity.

SUMMARY OF THE INVENTION

It has been found that the compounds of Formula (I), described below, are inhibitors of the tyrosine kinase activity of the IGF-1R. The presence of a sulfonyl group linked to the nitrogen of the dihydropyrrole ring of the bicyclic pyrrolo[3,4-c]pyrazole system is crucial for the activity of the compounds of the present invention as IGF-1R tyrosine kinase inhibitors.

Accordingly, one aspect of the invention provides a compound represented by Formula (I):

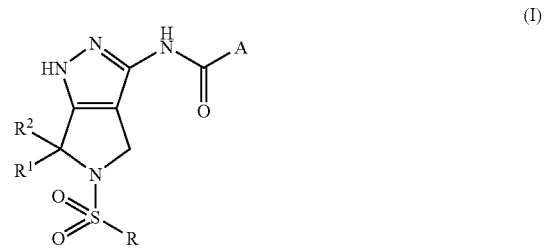

wherein:

R is selected from the group consisting of $(C_1-C_4)$alkyl, aryl and heteroaryl;

$R^1$ and $R^2$, which can be the same or different, are each independently selected from the group consisting of hydrogen and methyl;

A is selected from the group consisting of:

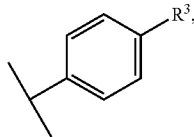

A0

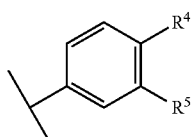

A1 and

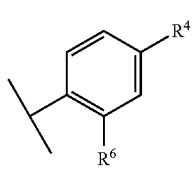

A2

$R^3$ is selected from the group consisting of $OR^7$, $NR^8R^9$ and heterocycloalkyl;

$R^4$ is selected from the group consisting of $NR^8R^9$ and heterocycloalkyl;

$R^5$ is selected from the group consisting of halogen, trifluoromethyl, $OR^7$, nitro, $NR^8R^9$, $NHCOR^{10}$ and $(C_1-C_4)$alkyl;

or $R^4$ and $R^5$, taken together with the carbon atoms to which they are bonded, form a heterocycloalkyl;

$R^6$ is selected from the group consisting of halogen, trifluoromethyl, nitro, amino and $NHCOR^{11}$;

$R^7$ is selected from the group consisting of $(C_1-C_4)$alkyl, aryl, and heterocycloalkyl;

$R^8$ and $R^9$, which can be the same or different, are each independently selected from the group consisting of hydrogen and $(C_1-C_4)$alkyl;

$R^{10}$ is $(C_1-C_4)$alkyl or $(C_3-C_5)$cycloalkyl;

$R^{11}$ is selected from the group consisting of isopropyl, cyclobutyl, —$CH_2NH_2$, —$CH_2NHCH_3$, —$CH_2N(CH_3)_2$, —$CH(NH_2)CH_3$, and pyrrolidin-2-yl;

or a pharmaceutically acceptable salt or solvate thereof, with the proviso that the compound of Formula (I) is not:

N-(5-methanesulfonyl-1,4,5,6-tetrahydro-pyrrolo[3,4-c]pyrazol-3-yl)-4-phenoxy-benzamide;

4-phenoxy-N-(5-phenylmethanesulfonyl-1,4,5,6-tetrahydro-pyrrolo[3,4-c]pyrazol-3-yl)-benzamide;

N-(5-benzenesulfonyl-1,4,5,6-tetrahydro-pyrrolo[3,4-c]pyrazol-3-yl)-4-(4-methyl-piperazin-1-yl)-benzamide;

2,3-dihydro-benzo[1,4]dioxine-6-carboxylic acid (5-benzenesulfonyl-1,4,5,6-tetrahydro-pyrrolo[3,4-c]pyrazol-3-yl)-amide;

2,3-dihydro-benzo[1,4]dioxine-6-carboxylic acid [5-(2-trifluoromethyl-benzenesulfonyl)-1,4,5,6-tetrahydro-pyrrolo[3,4-c]pyrazol-3-yl]-amide;

N-(5-methanesulfonyl-1,4,5,6-tetrahydro-pyrrolo[3,4-c]pyrazol-3-yl)-4-methoxy-benzamide;

4-methoxy-N-[5-(toluene-4-sulfonyl)-1,4,5,6-tetrahydro-pyrrolo[3,4-c]pyrazol-3-yl]-benzamide; or 4-methoxy-N-(5-phenylmethanesulfonyl-1,4,5,6-tetrahydro-pyrrolo[3,4-c]pyrazol-3-yl)-benzamide.

Another aspect of the invention relates to a pharmaceutical composition comprising an amount of the compound according to Formula (I) and a pharmaceutically acceptable carrier.

Another aspect of the invention relates to a method of treating a disorder or condition in a mammal, wherein said disorder or condition is caused by or associated with dysregulated protein kinase activity, particularly IGF-1R or Aurora kinases activity, and more particularly IGF-1R kinase activity comprising administering to said mammal in need of said treatment the compound of Formula (I).

Another aspect of the invention relates to a method of inhibiting tyrosine kinase activity of IGF-1R comprising administering to the IGF-1R an amount of the compound of Formula (I) that is effective in inhibiting tyrosine kinase activity of the IGF-1R.

Another aspect of the invention relates to a method of treating a disorder or condition in a mammal, wherein inhibition of tyrosine kinase activity of the IGF-1R is needed in said mammal, comprising administering to said mammal an amount of a compound of Formula (I) that is effective in inhibiting tyrosine kinase activity of the IGF-1R.

Another aspect of the invention relates to a method of treating a disorder or condition in a mammal for which inhibition of tyrosine kinase activity of the IGF-1R is needed in said mammal, comprising administering to said mammal an amount of the compound of Formula (I) that is effective in treating said disorder or condition.

Another aspect of the invention relates to a method of treating a disorder or condition selected from the group consisting of cancer, cell proliferative disorders, viral infections, retinopathies, age related macular degeneration, atherosclerosis, conditions involving vascular smooth muscle proliferation or neointimal formation, restenosis following angioplasty or surgery, graft vessel disease, acromegaly, disorders secondary to acromegaly, hypertrophic conditions in which IGF/IGF-1R signaling is implicated, benign prostatic hyperplasia, psoriasis, pulmonary fibrosis, pathologies related to chronic or acute oxidative stress or hyperoxia-induced tissue damage, metabolic disorders in which elevated IGF levels or IGF-1R activity are implicated, and obesity, in a mammal, comprising administering to said mammal in need of said treatment an amount of a compound of Formula (I) that is effective in treating said disorder or condition.

Another aspect of the invention relates to a method of treating a disorder or condition selected from the group consisting of cancer, cell proliferative disorders, viral infections, retinopathies, age related macular degeneration, atherosclerosis, conditions involving vascular smooth muscle proliferation or neointimal formation, restenosis following angioplasty or surgery, graft vessel disease, acromegaly, disorders secondary to acromegaly, hypertrophic conditions in which IGF/IGF-1R signaling is implicated, benign prostatic hyperplasia, psoriasis, pulmonary fibrosis, pathologies related to chronic or acute oxidative stress or hyperoxia-induced tissue damage, metabolic disorders in which elevated IGF levels or IGF-1R activity are implicated, and obesity, in a mammal, comprising administering to said mammal in need of said treatment an amount of a compound of Formula (I) that is effective in inhibiting tyrosine kinase activity of IGF-1R.

In another embodiment, the cancer in the above methods is selected from the group consisting of carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

In another embodiment, the proliferative disorder in the above methods is selected from the group consisting of familial adenomatosis polyposis, neuro-fibromatosis, arthritis and glomerulonephritis.

Another aspect of the invention relates to a method of treating diseases mediated by dysregulated protein kinase activity, which includes receptor tyrosine kinases (RTKs), non-receptor protein tyrosine kinases (CTKs) and serine/threonine protein kinases (STKs), in a mammal, which method comprises administering to said mammal in need of said treatment a pharmaceutical composition comprising a compound of Formula (I) in combination with one or more chemotherapeutic agents or radiotherapy. Such chemotherapeutic agents can include, but are not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

The compounds of Formula I also include derivatives of the compounds of Formula (I). The pyrrolo[3,4-c]pyrazole derivatives of Formula (I) can be prepared through a synthetic process consisting of standard synthetic transformations, which are comprised within the scope of the invention, and reported for instance in Smith, Michael—*March's Advanced Organic Chemistry: reactions mechanisms and structure*— 5th Edition, Michael B. Smith and Jerry March, John Wiley & Sons Inc., New York (NY), 2001), which is incorporated herein as reference. It is known to the skilled person that transformation of a chemical function into another can require that one or more reactive centers in the compound containing this function be protected in order to avoid undesired side reactions. Protection of such reactive centers, and subsequent deprotection at the end of the synthetic transformations, can be accomplished following standard procedures described in: Green, Theodora W. and Wuts, Peter G. M.—*Protective Groups in Organic Synthesis, Third Edition*, John Wiley & Sons Inc., New York (NY), 1999, which is incorporated herein as reference.

Analogues of compounds of Formula (I) have been described in the PCT international application WO 2002012242.

The present invention also provides a pharmaceutical composition comprising one or more compounds of Formula (I) or a pharmaceutically acceptable salt thereof and a pharmaceutically acceptable excipient, carrier or diluent.

BRIEF DESCRIPTION OF THE FIGURE

FIG. 1: FIG. 1 represents SEQ ID NO: 3, which is a fusion protein which consists essentially of an N-terminal GST/linker peptide moiety (amino acids 1-231 of SEQ ID NO: 3) and a C-terminal moiety representing the human IGF-1R intracellular domain (amino acids 232-639 of SEQ ID NO: 3).

FIG. 2 shows the inhibition of IGF1R auto-phosphorylation in MCF-7 starved cells stimulated with 10 nM IGF1 by compounds of formula (I), exemplified by compounds of examples 43 and 49. Treatment of starved MCF-7 cells with 10 nM IGF1 induced receptor auto-phosphorylation as shown by the appearance of a more intense band of phosphorylated IGF1R (pIGF1R). Incubation of cells with increasing concentrations of compounds described in examples 43 and 49 prior to treatment with IGF1 resulted in inhibition of IGF1-induced IGF1R auto-phosphorylation as shown by the decrease in intensity or disappearance of the band of phosphorylated IGF1R (pIGF1R).

DETAILED DESCRIPTION OF THE INVENTION

Figure 2:
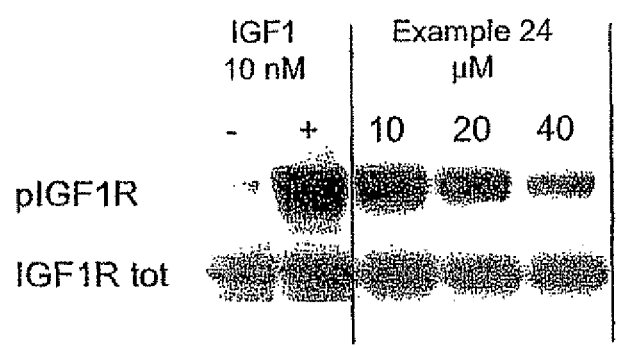
FIG. 2.

The invention relates to a compound represented by Formula (I):

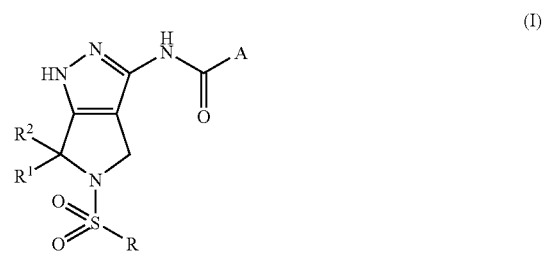

wherein:
R is selected from the group consisting of $(C_1\text{-}C_4)$alkyl, aryl and heteroaryl;
$R^1$ and $R^2$, which can be the same or different, are each independently selected from the group consisting of hydrogen and methyl;
A is selected from the group consisting of:

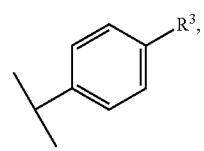

A0

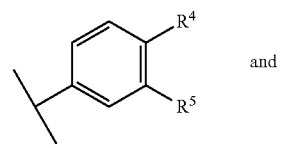

and

A1

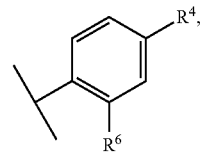

A2

$R^3$ is selected from the group consisting of $OR^7$, $NR^8R^9$ and heterocycloalkyl;
$R^4$ is selected from the group consisting of $NR^8R^9$ and heterocycloalkyl;
$R^5$ is selected from the group consisting of halogen, trifluoromethyl, $OR^7$, nitro, $NR^8R^9$, $NHCOR^{10}$ and $(C_1\text{-}C_4)$alkyl;
or $R^4$ and $R^5$, taken together with the carbon atoms to which they are bonded, form a heterocycloalkyl;
$R^6$ is selected from the group consisting of halogen, trifluoromethyl, nitro, amino and $NHCOR^{11}$;
$R^7$ is selected from the group consisting of $(C_1\text{-}C_4)$alkyl, aryl, and heterocycloalkyl;
$R^8$ and $R^9$, which can be the same or different, are each independently selected from the group consisting of hydrogen and $(C_1\text{-}C_4)$alkyl;
$R^{10}$ is $(C_1\text{-}C_4)$alkyl or $(C_3\text{-}C_5)$cycloalkyl;

$R^{11}$ is selected from the group consisting of isopropyl, cyclobutyl, —CH$_2$NH$_2$, —CH$_2$NHCH$_3$, —CH$_2$N(CH$_3$)$_2$, —CH(NH$_2$)CH$_3$, and pyrrolidin-2-yl;

or a pharmaceutically acceptable salt or solvate thereof, with the proviso that the compound of Formula (I) is not:

N-(5-methanesulfonyl-1,4,5,6-tetrahydro-pyrrolo[3,4-c]pyrazol-3-yl)-4-phenoxy-benzamide;

4-phenoxy-N-(5-phenylmethanesulfonyl-1,4,5,6-tetrahydro-pyrrolo[3,4-c]pyrazol-3-yl)-benzamide;

N-(5-benzenesulfonyl-1,4,5,6-tetrahydro-pyrrolo[3,4-c]pyrazol-3-yl)-4-(4-methyl-piperazin-1-yl)-benzamide;

2,3-dihydro-benzo[1,4]dioxine-6-carboxylic acid (5-benzenesulfonyl-1,4,5,6-tetrahydro-pyrrolo[3,4-c]pyrazol-3-yl)-amide;

2,3-dihydro-benzo[1,4]dioxine-6-carboxylic acid [5-(2-trifluoromethyl-benzenesulfonyl)-1,4,5,6-tetrahydro-pyrrolo[3,4-c]pyrazol-3-yl]-amide;

N-(5-methanesulfonyl-1,4,5,6-tetrahydro-pyrrolo[3,4-c]pyrazol-3-yl)-4-methoxy-benzamide;

4-methoxy-N-[5-(toluene-4-sulfonyl)-1,4,5,6-tetrahydro-pyrrolo[3,4-c]pyrazol-3-yl]-benzamide; or 4-methoxy-N-(5-phenylmethanesulfonyl-1,4,5,6-tetrahydro-pyrrolo[3,4-c]pyrazol-3-yl)-benzamide.

Fused bicyclic compounds comprising pyrazole moieties and possessing kinase inhibitory activity were disclosed in WO 00/69846, WO 02/12242, WO 03/028720 and WO04/056827, all in the name of the applicant itself.

In addition to the above, similar derivatives were disclosed in WO 2005/030776 in the name of Vertex. The compounds of Formula (I) of the present invention are comprised in the general formula of the aforementioned WO02/12242, but were not specifically therein.

The compounds of Formula (I) can have one or more asymmetric centres, and can therefore exist as individual optical isomers or racemic mixtures. Accordingly, all the possible isomers, and their mixtures, of the compounds of Formula (I) are within the scope of the present invention. Derivatives of compounds of Formula (I) originating from metabolism in a mammal, and the pharmaceutically acceptable bio-precursors (otherwise referred to as pro-drugs) of the compounds of Formula (I) are also within the scope of the present invention.

In addition to the above, as known to those skilled in the art, the unsubstituted pyrazole ring of the compounds of Formula (I) rapidly equilibrates in solution to form mixtures of tautomers, as depicted below:

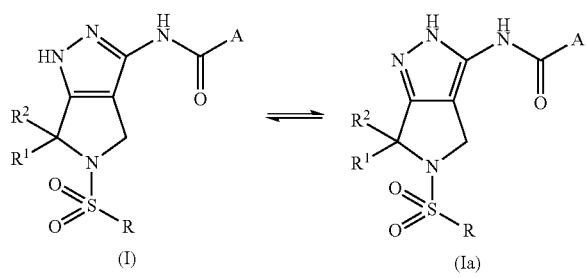

Accordingly, in the present invention, where only one tautomer is indicated for the compounds of Formula (I), the other tautomer (Ia) is also within the scope of the present invention, unless otherwise indicated.

The general terms as used herein, unless otherwise specified, have the meaning reported below.

Except where stated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkylamino", "dialkylamino" etc.

The term "(C$_1$-C$_4$)alkyl" refers to a saturated aliphatic hydrocarbon radical, including straight chain and branched chain groups of from 1 to 4 carbon atoms, e.g. methyl, ethyl, propyl, 2-propyl, n-butyl, iso-butyl, and tert-butyl. The alkyl group can be substituted or unsubstituted. When substituted, the substituent groups are preferably one to three, more preferably one or two substituents independently selected from the group consisting of aryl, halogen, trifluoromethyl, hydroxy, alkoxy, alkylthio, cyano, formyl, alkylcarbonyl, alkylsulphonyl, amino, monoalkylamino, dialkylamino, arylalkylamino, carboxy, carboxamido, monoalkylcarboxamido and dialkylcarboxamido.

The term "(C$_3$-C$_5$)cycloalkyl" refers to a 3 to 5-membered all-carbon monocyclic ring, which can contain one double bond. Examples of cycloalkyl groups are cyclopropane, cyclobutane, cyclopentane, cyclopentene. A cycloalkyl group can be substituted or unsubstituted. When substituted, the substituent groups are preferably one or two substituents, independently selected from the group consisting of halogen, trifluoromethyl, hydroxy, hydroxyalkyl, alkoxy, alkylthio, cyano, formyl, alkylcarbonyl, alkylsulphonyl, amino, monoalkylamino, dialkylamino, arylalkylamino, carboxy, carboxamido, monoalkylcarboxamido and dialkylcarboxamido.

The term "heterocycloalkyl" refers to a 5- or 6-membered, saturated or partially unsaturated carbocyclic ring where one or more carbon atoms are replaced by heteroatoms such as nitrogen, oxygen and sulfur. Not limiting examples of heterocycloalkyl groups are, for instance, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, isoxazolidine, isoxazoline, thiazolidine, thiazoline, isothiazoline, dioxane, piperazine, morpholine, thiomorpholine, and the like. A heterocycloalkyl group can be substituted or unsubstituted. When substituted, the substituent groups are preferably one or two substituents, independently selected from the group consisting of (C$_1$-C$_4$)alkyl, halogen, trifluoromethyl, hydroxy, hydroxyalkyl, alkoxy, alkylthio, cyano, formyl, alkylcarbonyl, alkylsulphonyl, amino, monoalkylamino, dialkylamino, arylalkylamino, carboxy, carboxamido, monoalkylcarboxamido and dialkylcarboxamido.

The term "heteroaryl" refers a mono-, bi- or heterocyclic with from 1 to 4 ring systems, either fused or linked to each other by single bonds, wherein at least one of the heterocyclic rings is aromatic. Not limiting examples of heteroaryl groups include pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl, and the like.

The term "aryl" refers to a mono-, bi- or poly-carbocyclic with from 1 to 4 ring systems, either fused or linked to each other by single bonds, wherein at least one of the carbocyclic rings is aromatic. Not limiting examples of aryl groups include phenyl, indanyl, biphenyl, α- or β-naphthyl, fluorenyl, 9,10-dihydroanthracenyl, and the like.

The terms "aryl" and "heteroaryl" can also refer to aromatic carbocyclic or heterocyclic rings, respectively, further fused or linked to non-aromatic heterocyclic rings, typically 5- to 7-membered heterocycles. Not limiting examples of such aryl and heteroaryl groups are, for instance, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl, and the like. The aryl or heteroaryl groups can be unsubstituted or substituted by one to three, preferably one or two, substituents selected from $(C_1\text{-}C_4)$ alkyl, halogen, trifluoromethyl, hydroxy, hydroxyalkyl, alkoxy, alkylthio, cyano, formyl, alkylcarbonyl, alkylsulphonyl, amino, monoalkylamino, dialkylamino, arylalkylamino, carboxy, carboxamido, monoalkylcarboxamido, dialkylcarboxamido.

The term "halogen" indicates fluorine, chlorine, bromine or iodine.

The term "trifluoromethyl" indicates a —$CF_3$ group.

The term "hydroxy" indicates an —OH group.

The term "hydroxyalkyl" indicates a hydroxy group linked to an alkyl group. Examples of hydroxyalkyl groups are hydroxymethyl (—$CH_2OH$), 2-hydroxyethyl (—$CH_2CH_2OH$) and the like.

The term "alkoxy" indicates a residue where an alkyl group substitutes the hydrogen of the hydroxy (—O-alkyl). Examples of alkoxy groups are methoxy (—$OCH_3$), ethoxy (—$OCH_2CH_3$), isopropyloxy [—$OCH(CH_3)_2$], and the like.

The term "alkylthio" indicates an alkyl group linked to a sulphur atom (—S-alkyl). Examples of alkylthio groups are methylthio (—$SCH_3$), ethylthio (—$SCH_2CH_3$), isopropylthio [—$SCH(CH_3)_2$], and the like.

The term "cyano" indicates a —CN residue.

The term "formyl" indicates a —CHO residue.

The term "alkylcarbonyl" indicates an alkyl residue linked to a CO group [—C(=O)alkyl]. Examples of alkylcarbonyl are methylcarbonyl [—C(=O)$CH_3$], ethylcarbonyl [—C(=O)$CH_2CH_3$], and the like.

The term "alkylsulphonyl" indicates a —$SO_2$alkyl group. Examples of alkylsulphonyl groups are methylsulphonyl (—$SO_2CH_3$), ethylsulphonyl (—$SO_2CH_2CH_3$), and the like.

The term "nitro" indicates a —$NO_2$ group.

The term "amino" indicates an —$NH_2$ group.

The terms "monoalkylamino" or "dialkylamino" indicate an amino group where one or both hydrogens are substituted by an alkyl group. Examples of monoalkylamino are methylamino (—$NHCH_3$), ethylamino (—$NHCH_2CH_3$) and the like. Examples of dialkylamino are dimethylamino [—N($CH_3)_2$], diethylamino [—N($CH_2CH_3)_2$], and the like.

The term "arylalkylamino" indicates an aryl group linked to an amino function through an alkyl group. Examples or arylalkylamino are benzylamino (—$NHCH_2$Phenyl), phenethylamino (—$NHCH_2CH_2$Phenyl), and the like.

The term "carboxy" indicates a COOH group.

The term "carboxamido" indicates a —$CONH_2$ group.

The terms "monoalkylcarboxamido" or "dialkylcarboxamido" indicate a carboxamido group where one or both hydrogens are substituted by an alkyl group. Examples of monoalkylcarboxamido are methylcarboxamido (—$CONHCH_3$), ethylcarboxamido (—$CONHCH_2CH_3$), and the like. Examples of dialkylcarboxamido are dimethylcarboxamido [—$CON(CH_3)_2$], diethylcarboxamido [—$CON(CH_2CH_3)_2$], and the like.

The term "pharmaceutically acceptable salt" of compounds of Formula (I) refers to those salts that retain the biological effectiveness and properties of the parent compound. Such salts include: acid addition salt with inorganic acids such as hydrochloric, hydrobromic, nitric, phosphoric, sulfuric, and perchloric acid and the like, or with organic acids such as acetic, trifluoroacetic, propionic, glycolic, lactic, (D) or (L) malic, maleic, methanesulfonic, ethanesulfonic, benzoic, p-toluenesulfonic, salicylic, cinnamic, mandelic, tartaric, citric, succinic or malonic acid and the like; salts formed when an acidic proton present in a compound of Formula (I) is either replaced by a metal ion, e.g., an alkali metal ion such as sodium or potassium, or an alkaline earth ion such as calcium or magnesium, or coordinates with an organic base such as ethanolamine, diethanolamine, triethanolamine, tromethamine, N-methylglucamine, and the like.

Preferred compounds of Formula (I) are the compounds wherein:

R is selected from the group consisting of $(C_1\text{-}C_4)$alkyl and aryl;

A is selected from the group consisting of:

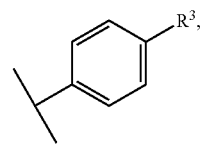

A0

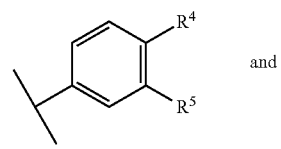

and

A1

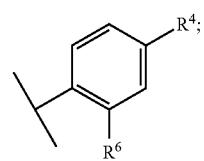

A2

$R^1$ and $R^2$, which can be the same or different, are each independently selected from the group consisting of hydrogen and methyl;

$R^3$ is selected from the group consisting of $OR^7$, $NR^8R^9$ and heterocycloalkyl;

$R^4$ is selected from the group consisting of $NR^8R^9$ and heterocycloalkyl;

$R^5$ is selected from the group consisting of halogen, trifluoromethyl, nitro, $NR^8R^9$, $NHCOR^{10}$, and $(C_1\text{-}C_4)$alkyl;

or $R^4$ and $R^5$, taken together with the carbon atoms to which they are bonded, form a heterocycloalkyl;

$R^6$ is selected from the group consisting of halogen, amino, and $NHCOR^{11}$;

$R^7$ is selected from the group consisting of $(C_1\text{-}C_4)$alkyl and heterocycloalkyl;

$R^8$ and $R^9$, which can be the same or different, are each independently selected from the group consisting of hydrogen and $(C_1\text{-}C_4)$alkyl;

$R^{10}$ is selected from the group consisting of $(C_1\text{-}C_4)$alkyl and $(C_3\text{-}C_5)$cycloalkyl; and $R^{11}$ is selected from the group consisting of isopropyl, cyclobutyl, —$CH_2NH_2$, —$CH_2NHCH_3$, —$CH_2N(CH_3)_2$, —$CH(NH_2)CH_3$, and pyrrolidin-2-yl.

Other preferred compounds of Formula (I) are the compounds wherein:

R is selected from the group consisting of $(C_1\text{-}C_4)$alkyl and aryl;

A is selected from the group consisting of:

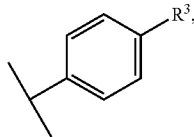
A0

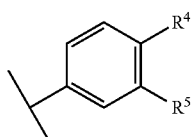
A1
and

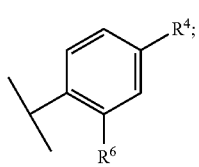
A2

$R^1$ and $R^2$, which can be the same or different, are each independently selected from the group consisting of hydrogen and methyl;

$R^3$ is heterocycloalkyl;

$R^4$ is selected from the group consisting of $NR^8R^9$ and heterocycloalkyl;

$R^5$ is selected from the group consisting of halogen, trifluoromethyl, nitro, $NR^8R^9$, $NHCOR^{10}$, and $(C_1-C_4)$alkyl;

or $R^4$ and $R^5$, taken together with the carbon atoms to which they are bonded, form a heterocycloalkyl, which is preferentially a dihydro-oxazine or a tetrahydropyrazine;

$R^6$ is selected from the group consisting of halogen, amino, and $NHCOR^{11}$;

$R^8$ and $R^9$, which can be the same or different, are each independently selected from the group consisting of hydrogen and $(C_1-C_4)$alkyl;

$R^{10}$ is selected from the group consisting of $(C_1-C_4)$alkyl and $(C_3-C_5)$cycloalkyl; and $R^{11}$ is selected from the group consisting of isopropyl, cyclobutyl, —$CH_2N(CH_3)_2$, and pyrrolidin-2-yl.

Further preferred compounds of Formula (I) are the compounds wherein:

R is aryl;

A is selected from the group consisting of:

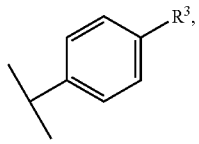
A0

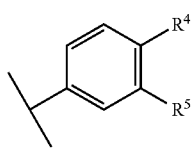
A1
and

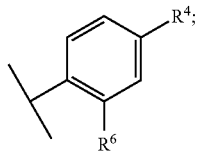
A2

$R^1$ and $R^2$, which can be the same or different, are each independently selected from the group consisting of hydrogen and methyl;

$R^3$ is heterocycloalkyl;

$R^4$ is selected from the group consisting of $NR^8R^9$ and heterocycloalkyl;

$R^5$ is selected from the group consisting of halogen, $NR^8R^9$, $NHCOR^{10}$, and $(C_1-C_4)$alkyl;

$R^6$ is selected from the group consisting of halogen, and $NHCOR^{11}$;

$R^8$ and $R^9$, which can be the same or different, are each independently selected from the group consisting of hydrogen and $(C_1-C_4)$alkyl;

$R^{10}$ is selected from the group consisting of $(C_1-C_4)$alkyl and $(C_3-C_5)$cycloalkyl; and $R^{11}$ is selected from the group consisting of isopropyl, cyclobutyl, —$CH_2N(CH_3)_2$, and pyrrolidin-2-yl.

Particularly preferred compounds of Formula (I) are the compounds wherein:

R is aryl;

A is selected from the group consisting of:

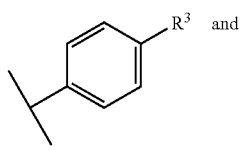
A0
and

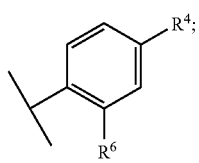
A2

$R^1$ and $R^2$ are each methyl;

$R^3$ is heterocycloalkyl;

$R^4$ is selected from the group consisting of $NR^8R^9$ and heterocycloalkyl;

$R^6$ is selected from the group consisting of halogen, and $NHCOR^{11}$;

$R^8$ and $R^9$, which can be the same or different, are each independently selected from the group consisting of hydrogen and $(C_1-C_4)$alkyl; and $R^{11}$ is selected from the group consisting of isopropyl, cyclobutyl, and —$CH_2N(CH_3)_2$.

More preferred compounds of Formula (I) are the compounds wherein:

R is selected from the group consisting of phenyl, a 2-substituted-phenyl, a 3-substituted-phenyl, a 2,6-di-substituted-phenyl and a 3,5-di-substituted-phenyl;

A is selected from the group consisting of:

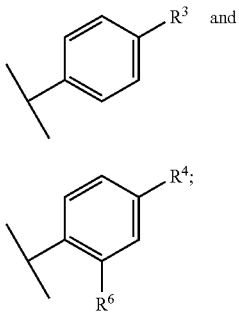

$R^1$ and $R^2$ are each methyl;
$R^3$ is a six-membered heterocycloalkyl;
$R^4$ is selected from the group consisting of $NR^8R^9$ and a six-membered heterocycloalkyl;
$R^6$ is selected from the group consisting of halogen, and $NHCOR^{11}$;
$R^8$ and $R^9$, which can be the same or different, are each independently selected from the group consisting of hydrogen and $(C_1-C_4)$alkyl; and
$R^{11}$ is selected from the group consisting of isopropyl, cyclobutyl and $CH_2N(CH_3)_2$.

Most preferred compounds of Formula (I) are the compounds wherein:
R is selected from the group consisting of phenyl, a 3-substituted-phenyl and a 3,5-di-substituted-phenyl;
A is selected from the group consisting of:

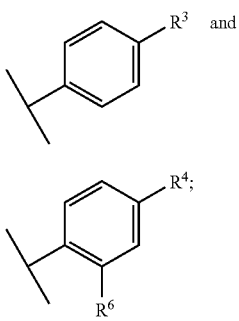

$R^1$ and $R^2$ are each methyl;
$R^3$ is selected from the group consisting of morpholine and a substituted piperazine;
$R^4$ is selected from the group consisting of $NR^8R^9$, morpholine and a substituted piperazine
$R^6$ is selected from the group consisting of fluorine and $NHCOR^{11}$;
$R^8$ and $R^9$ are each methyl; and
$R^{11}$ is selected from the group consisting of isopropyl, cyclobutyl and —$CH_2N(CH_3)_2$.

Specific, not limiting, examples of compounds of the invention, whenever appropriate in the form of pharmaceutically acceptable salts, are the following:
N-(5-Benzenesulfonyl-1,4,5,6-tetrahydro-pyrrolo[3,4-c] pyrazol-3-yl)-4-piperazin-1-yl-benzamide;
N-(5-Benzenesulfonyl-1,4,5,6-tetrahydro-pyrrolo[3,4-c] pyrazol-3-yl)-4-(4-methyl-piperazin-1-yl)-benzamide;
4-(4-Methyl-piperazin-1-yl)-N-[5-(thiophene-2-sulfonyl)-1,4,5,6-tetrahydro-pyrrolo[3,4-c]pyrazol-3-yl]-benzamide;
N-[5-(3-Chloro-thiophene-2-sulfonyl)-1,4,5,6-tetrahydro-pyrrolo[3,4-c]pyrazol-3-yl]-4-(4-methyl-piperazin-1-yl)-benzamide;
N-[5-(1,2-Dimethyl-1H-imidazole-4-sulfonyl)-1,4,5,6-tetrahydro-pyrrolo[3,4-c]pyrazol-3-yl]-4-(4-methyl-piperazin-1-yl)-benzamide;
N-(5-Methanesulfonyl-1,4,5,6-tetrahydro-pyrrolo[3,4-c] pyrazol-3-yl)-4-(4-methyl-piperazin-1-yl)-benzamide;
4-(4-Methyl-piperazin-1-yl)-N-[5-(propane-2-sulfonyl)-1,4,5,6-tetrahydro-pyrrolo[3,4-c]pyrazol-3-yl]-benzamide;
N-[5-(Butane-1 sulfonyl)-1,4,5,6-tetrahydro-pyrrolo[3,4-c] pyrazol-3-yl]-4-(4-methyl-piperazin-1-yl)-benzamide;
4-(4-Methyl-piperazin-1-yl)-N-(5-phenylmethanesulfonyl-1,4,5,6-tetrahydro-pyrrolo[3,4-c]pyrazol-3-yl)-benzamide;
N-(5-Benzenesulfonyl-1,4,5,6-tetrahydro-pyrrolo[3,4-c] pyrazol-3-yl)-4-(4-ethyl-piperazin-1-yl)-benzamide;
N-(5-Benzenesulfonyl-1,4,5,6-tetrahydro-pyrrolo[3,4-c] pyrazol-3-yl)-4-(4-isopropyl-piperazin-1-yl)-benzamide;
N-(5-Benzenesulfonyl-1,4,5,6-tetrahydro-pyrrolo[3,4-c] pyrazol-3-yl)-4-(4-tert-butyl-piperazin-1-yl)-benzamide;
N-(5-Benzenesulfonyl-1,4,5,6-tetrahydro-pyrrolo[3,4-c] pyrazol-3-yl)-4-[4-(2-hydroxy-ethyl)-piperazin-1-yl]-benzamide;
N-(5-Benzenesulfonyl-1,4,5,6-tetrahydro-pyrrolo[3,4-c] pyrazol-3-yl)-4-(4-benzyl-piperazin-1-yl)-benzamide;
N-(5-Benzenesulfonyl-1,4,5,6-tetrahydro-pyrrolo[3,4-c] pyrazol-3-yl)-4-(4-cyclopropyl-piperazin-1-yl)-benzamide;
N-(5-Benzenesulfonyl-1,4,5,6-tetrahydro-pyrrolo[3,4-c] pyrazol-3-yl)-4-(3,4-dimethyl-piperazin-1-yl)-benzamide;
N-(5-Benzenesulfonyl-1,4,5,6-tetrahydro-pyrrolo[3,4-c] pyrazol-3-yl)-4-morpholin-4-yl-benzamide;
N-(5-Benzenesulfonyl-1,4,5,6-tetrahydro-pyrrolo[3,4-c] pyrazol-3-yl)-4-piperidin-1-yl-benzamide;
N-(5-Benzenesulfonyl-1,4,5,6-tetrahydro-pyrrolo[3,4-c] pyrazol-3-yl)-4-(4-hydroxy-piperidin-1-yl)-benzamide;
N-(5-Benzenesulfonyl-1,4,5,6-tetrahydro-pyrrolo[3,4-c] pyrazol-3-yl)-4-(4-fluoro-piperidin-1-yl)-benzamide;
N-(5-Benzenesulfonyl-1,4,5,6-tetrahydro-pyrrolo[3,4-c] pyrazol-3-yl)-4-(1-methyl-piperidin-4-yl)-benzamide;
N-(5-Benzenesulfonyl-1,4,5,6-tetrahydro-pyrrolo[3,4-c] pyrazol-3-yl)-4-(1-methyl-piperidin-4-yloxy)-benzamide;
N-(5-Benzenesulfonyl-1,4,5,6-tetrahydro-pyrrolo[3,4-c] pyrazol-3-yl)-4-((S)-2-hydroxymethyl-pyrrolidin-1-yl)-benzamide;
N-[5-(2-Fluoro-benzenesulfonyl)-1,4,5,6-tetrahydro-pyrrolo[3,4-c]pyrazol-3-yl]-4-(4-methyl-piperazin-1-yl)-benzamide;
N-[5-(3-Fluoro-benzenesulfonyl)-1,4,5,6-tetrahydro-pyrrolo[3,4-c]pyrazol-3-yl]-4-(4-methyl-piperazin-1-yl)-benzamide;
N-[5-(4-Fluoro-benzenesulfonyl)-1,4,5,6-tetrahydro-pyrrolo[3,4-c]pyrazol-3-yl]-4-(4-methyl-piperazin-1-yl)-benzamide;
N-[5-(2-Chloro-benzenesulfonyl)-1,4,5,6-tetrahydro-pyrrolo[3,4-c]pyrazol-3-yl]-4-(4-methyl-piperazin-1-yl)-benzamide;
N-[5-(3-Chloro-benzenesulfonyl)-1,4,5,6-tetrahydro-pyrrolo[3,4-c]pyrazol-3-yl]-4-(4-methyl-piperazin-1-yl)-benzamide;

N-[5-(4-Chloro-benzenesulfonyl)-1,4,5,6-tetrahydro-pyrrolo[3,4-c]pyrazol-3-yl]-4-(4-methyl-piperazin-1-yl)-benzamide;

4-(4-Methyl-piperazin-1-yl)-N-[5-(toluene-2-sulfonyl)-1,4,5,6-tetrahydro-pyrrolo[3,4-c]pyrazol-3-yl]-benzamide;

4-(4-Methyl-piperazin-1-yl)-N-[5-(toluene-3-sulfonyl)-1,4,5,6-tetrahydro-pyrrolo[3,4-c]pyrazol-3-yl]-benzamide;

4-(4-Methyl-piperazin-1-yl)-N-[5-toluene-4-sulfonyl)-1,4,5,6-tetrahydro-pyrrolo[3,4-c]pyrazol-3-yl]-benzamide;

4-(4-Methyl-piperazin-1-yl)-N-[5-(2-trifluoromethyl-benzenesulfonyl)-1,4,5,6-tetrahydro-pyrrolo[3,4-c]pyrazol-3-yl]-benzamide;

4-(4-Methyl-piperazin-1-yl)-N-[5-(3-trifluoromethyl-benzenesulfonyl)-1,4,5,6-tetrahydro-pyrrolo[3,4-c]pyrazol-3-yl]-benzamide;

4-(4-Methyl-piperazin-1-yl)-N-[5-(4-trifluoromethyl-benzenesulfonyl)-1,4,5,6-tetrahydro-pyrrolo[3,4-c]pyrazol-3-yl]-benzamide;

N-[5-(2-Cyano-benzenesulfonyl)-1,4,5,6-tetrahydro-pyrrolo[3,4-c]pyrazol-3-yl]-4-(4-methyl-piperazin-1-yl)-benzamide;

N-[5-(3-Cyano-benzenesulfonyl)-1,4,5,6-tetrahydro-pyrrolo[3,4-c]pyrazol-3-yl]-4-(4-methyl-piperazin-1-yl)benzamide;

N-[5-(4-Cyano-benzenesulfonyl)-1,4,5,6-tetrahydro-pyrrolo[3,4-c]pyrazol-3-yl]-4-(4-methyl-piperazin-1-yl)-benzamide;

3-{3-[4-(4-Methyl-piperazin-1-yl)-benzoylamino]-4,6-dihydro-1H-pyrrolo[3,4-c]pyrazole-5-sulfonyl}-benzoic acid;

N-[5-(3-Hydroxy-benzenesulfonyl)-1,4,5,6-tetrahydro-pyrrolo[3,4-c]pyrazol-3-yl]-4-(4-methyl-piperazin-1-yl)-benzamide;

N-[5-(4-Hydroxy-benzenesulfonyl)-1,4,5,6-tetrahydro-pyrrolo[3,4-c]pyrazol-3-yl]-4-(4-methyl-piperazin-1-yl)-benzamide;

N-[5-(3-Methoxy-benzenesulfonyl)-1,4,5,6-tetrahydro-pyrrolo[3,4-c]pyrazol-3-yl]-4-(4-methyl-piperazin-1-yl)benzamide;

N-[5-(4-Methoxy-benzenesulfonyl)-1,4,5,6-tetrahydro-pyrrolo[3,4-c]pyrazol-3-yl]-4-(4-methyl-piperazin-1-yl)-benzamide;

4-(4-Methyl-piperazin-1-yl)-N-[5-(4-trifluoromethoxy-benzenesulfonyl)-1,4,5,6-tetrahydro-pyrrolo[3,4-c]pyrazol-3-yl]-benzamide;

N-[5-(3-Amino-benzenesulfonyl)-1,4,5,6-tetrahydro-pyrrolo[3,4-c]pyrazol-3-yl]-4-(4-methyl-piperazin-1-yl)-benzamide;

N-[5-(2,6-Difluoro-benzenesulfonyl)-1,4,5,6-tetrahydro-pyrrolo[3,4-c]pyrazol-3-yl]-4-(4-methyl-piperazin-1-yl)-benzamide;

N-[5-(2,5-Difluoro-benzenesulfonyl)-1,4,5,6-tetrahydro-pyrrolo[3,4-c]pyrazol-3-yl]-4-(4-methyl-piperazin-1-yl)-benzamide;

N-[5-(3,4-Difluoro-benzenesulfonyl)-1,4,5,6-tetrahydro-pyrrolo[3,4-c]pyrazol-3-yl]-4-(4-methyl-piperazin-1-yl)-benzamide;

N-[5-(3,5-Difluoro-benzenesulfonyl-1,4,5,6-tetrahydro-pyrrolo[3,4-c]pyrazol-3-yl]-4-(4-methyl-piperazin-1-yl)-benzamide;

N-[5-(2,6-Dichloro-benzenesulfonyl)-1,4,5,6-tetrahydro-pyrrolo[3,4-c]pyrazol-3-yl]-4-(4-methyl-piperazin-1-yl)-benzamide;

N-[5-(2-Chloro-6-methyl-benzenesulfonyl)-1,4,5,6-tetrahydro-pyrrolo[3,4-c]pyrazol-3-yl]-4-(4-methyl-piperazin-1-yl)benzamide;

N-(5-Benzenesulfonyl-1,4,5,6-tetrahydro-pyrrolo[3,4-c]pyrazol-3-yl)-4-(4-methyl-piperazin-1-yl)-2-trifluoromethyl-benzamide;

N-(5-Benzenesulfonyl-1,4,5,6-tetrahydro-pyrrolo[3,4-c]pyrazol-3-yl)-4-(4-methyl-piperazin-1-yl)-3-trifluoromethyl-benzamide;

N-(5-Benzenesulfonyl-1,4,5,6-tetrahydro-pyrrolo[3,4-c]pyrazol-3-yl)-4-(4-methyl-piperazin-1-yl)-3-nitro-benzamide;

3-Amino-N-(5-benzenesulfonyl-1,4,5,6-tetrahydro-pyrrolo[3,4-c]pyrazol-3-yl)-4-(4-methyl-piperazin-1-yl)-benzamide;

4-Methyl-3,4-dihydro-2H-benzo[1,4]oxazine-7-carboxylic acid (5-benzenesulfonyl-1,4,5,6-tetrahydro-pyrrolo[3,4-c]pyrazol-3-yl)-amide;

4-Ethyl-3,4-dihydro-2H-benzo[1,4]oxazine-7-carboxylic acid (5-benzenesulfonyl-1,4,5,6-tetrahydro-pyrrolo[3,4-c]pyrazol-3-yl)-amide;

4-(2-Hydroxy-ethyl)-3,4-dihydro-2H-benzo[1,4]oxazine-7-carboxylic acid (5-benzenesulfonyl-1,4,5,6-tetrahydro-pyrrolo[3,4-c]pyrazol-3-yl)-amide;

4-(2-Benzyloxy-ethyl)-3,4-dihydro-2H-benzo[1,4]oxazine-7-carboxylic acid (5-benzenesulfonyl-1,4,5,6-tetrahydro-pyrrolo[3,4-c]pyrazol-3-yl)-amide;

N-[5-(3-Fluoro-benzenesulfonyl)-1,4,5,6-tetrahydro-pyrrolo[3,4-c]pyrazol-3-yl]-4-piperazin-1-yl-benzamide;

4-(3,4-Dimethyl-piperazin-1-yl)-N-[5-(3-fluoro-benzenesulfonyl)-1,4,5,6-tetrahydro-pyrrolo[3,4-c]pyrazol-3-yl]-benzamide;

N-[5-(3-Fluoro-benzenesulfonyl)-1,4,5,6-tetrahydro-pyrrolo[3,4-c]pyrazol-3-yl]-4-(3-hydroxymethyl-piperazin-1-yl)-benzamide;

N-[5-(3-Fluoro-benzenesulfonyl)-1,4,5,6-tetrahydro-pyrrolo[3,4-c]pyrazol-3-yl]-4-(2-hydroxymethyl-4-methyl-piperazin-1-yl)-benzamide;

N-[5-(3-Fluoro-benzenesulfonyl)-1,4,5,6-tetrahydro-pyrrolo[3,4-c]pyrazol-3-yl]-4-(3-hydroxymethyl-4-methyl-piperazin-1-yl)-benzamide;

N-[5-(3-Fluoro-benzenesulfonyl)-1,4,5,6-tetrahydro-pyrrolo[3,4-c]pyrazol-3-yl]-4-(3-methoxymethyl-4-methyl-piperazin-1-yl)-benzamide;

4-(3-Benzyloxymethyl-piperazin-1-yl)-N-[5-(3-fluoro-benzenesulfonyl)-1,4,5,6-tetrahydro-pyrrolo[3,4-c]pyrazol-3-yl]-benzamide;

4-(3-Benzyloxymethyl-4-methyl-piperazin-1-yl)-N-[5-(3-fluoro-benzenesulfonyl)-1,4,5,6-tetrahydro-pyrrolo[3,4-c]pyrazol-3-yl]-benzamide;

4-(4-Cyclopropyl-piperazin-1-yl)-N-[5-(3-fluoro-benzenesulfonyl)-1,4,5,6-tetrahydro-pyrrolo[3,4-c]pyrazol-3-yl]-benzamide;

4-(4-tert-Butyl-piperazin-1-yl)-N-[5-(3-fluoro-benzenesulfonyl)-1,4,5,6-tetrahydro-pyrrolo[3,4-c]pyrazol-3-yl]-benzamide;

N-[5-(3-Fluoro-benzenesulfonyl)-1,4,5,6-tetrahydro-pyrrolo[3,4-c]pyrazol-3-yl]-4-morpholin-4-yl-benzamide;

N-[5-(3-Fluoro-benzenesulfonyl)-1,4,5,6-tetrahydro-pyrrolo[3,4-c]pyrazol-3-yl]-4-(3-hydroxy-piperidin-1-yl)-benzamide;

N-[5-(3-Fluoro-benzenesulfonyl)-1,4,5,6-tetrahydro-pyrrolo[3,4-c]pyrazol-3-yl]-4-(3-hydroxymethyl-piperidin-1-yl)-benzamide;

4-[(2-Dimethylamino-ethyl)-methyl-amino]-N-[5-(3-fluoro-benzenesulfonyl)-1,4,5,6-tetrahydro-pyrrolo[3,4-c]pyrazol-3-yl]-benzamide;

4-(2-Dimethylamino-ethylamino)-N-[5-(3-fluoro-benzenesulfonyl)-1,4,5,6-tetrahydro-pyrrolo[3,4-c]pyrazol-3-yl]-benzamide;

N-[5-(3-Fluoro-benzenesulfonyl)-1,4,5,6-tetrahydro-pyrrolo[3,4-c]pyrazol-3-yl]-4-(4-methyl-piperazin-1-yl)-2-trifluoromethyl-benzamide;
N-[5-(3-Fluoro-benzenesulfonyl)-1,4,5,6-tetrahydro-pyrrolo[3,4-c]pyrazol-3-yl]-4-(4-methyl-piperazin-1-yl)-3-trifluoromethyl-benzamide;
N-[5-(3-Fluoro-benzenesulfonyl)-1,4,5,6-tetrahydro-pyrrolo[3,4-c]pyrazol-3-yl]-4-(4-methyl-piperazin-1-yl)-3-nitro-benzamide;
3-Amino-N-[5-(3-fluoro-benzenesulfonyl)-1,4,5,6-tetrahydro-pyrrolo[3,4-c]pyrazol-3-yl]-4-(4-methyl-piperazin-1-yl)-benzamide;
3-Acetylamino-N-[5-(3-fluoro-benzenesulfonyl)-1,4,5,6-tetrahydro-pyrrolo[3,4-c]pyrazol-3-yl]-4-(4-methyl-piperazin-1-yl)-benzamide;
3-(Cyclopropanecarbonyl-amino)-N-[5-(3-fluoro-benzenesulfonyl)-1,4,5,6-tetrahydro-pyrrolo[3,4-c]pyrazol-3-yl]-4-(4-methyl-piperazin-1-yl)-benzamide;
N-[5-(3-Fluoro-benzenesulfonyl)-1,4,5,6-tetrahydro-pyrrolo[3,4-c]pyrazol-3-yl]-3-(2-hydroxy-acetylamino)-4-(4-methyl-piperazin-1-yl)-benzamide;
N-[5-(3-Fluoro-benzenesulfonyl)-1,4,5,6-tetrahydro-pyrrolo[3,4-c]pyrazol-3-yl]-3-(2-methoxy-acetylamino)-4-(4-methyl-piperazin-1-yl)-benzamide;
N-[5-(3-Fluoro-benzenesulfonyl)-1,4,5,6-tetrahydro-pyrrolo[3,4-c]pyrazol-3-yl]-3-hydroxymethyl-4-(4-methyl-piperazin-1-yl)-benzamide;
N-[5-(3-Fluoro-benzenesulfonyl)-1,4,5,6-tetrahydro-pyrrolo[3,4-c]pyrazol-3-yl]-3-[(2-hydroxy-ethyl)-methyl-amino]-4-(4-methyl-piperazin-1-yl)-benzamide;
N-[5-(3-Fluoro-benzenesulfonyl)-1,4,5,6-tetrahydro-pyrrolo[3,4-c]pyrazol-3-yl]-4-(4-methyl-piperazin-1-yl)-2-nitro-benzamide;
2-Amino-N-[5-(3-fluoro-benzenesulfonyl)-1,4,5,6-tetrahydro-pyrrolo[3,4-c]pyrazol-3-yl]-4-(4-methyl-piperazin-1-yl)-benzamide;
1-Methyl-1,2,3,4-tetrahydro-quinoxaline-6-carboxylic acid [5-(3-fluoro-benzenesulfonyl)-1,4,5,6-tetrahydro-pyrrolo[3,4-c]pyrazol-3-yl]-amide;
1-Cyclopropanecarbonyl-1,2,3,4-tetrahydro-quinoxaline-6-carboxylic acid [5-(3-fluoro-benzenesulfonyl)-1,4,5,6-tetrahydro-pyrrolo[3,4-c]pyrazol-3-yl]-amide;
4-Methyl-3,4-dihydro-2H-benzo[1,4]oxazine-7-carboxylic acid [5-(3-fluoro-benzenesulfonyl)-1,4,5,6-tetrahydro-pyrrolo[3,4-c]pyrazol-3-yl]-amide;
4-Ethyl-3,4-dihydro-2H-benzo[1,4]oxazine-7-carboxylic acid [5-(3-fluoro-benzenesulfonyl)-1,4,5,6-tetrahydro-pyrrolo[3,4-c]pyrazol-3-yl]-amide,
4-Isopropyl-3,4-dihydro-2H-benzo[1,4]oxazine-7-carboxylic acid [5-(3-fluoro-benzenesulfonyl)-1,4,5,6-tetrahydro-pyrrolo[3,4-c]pyrazol-3-yl]-amide;
4-(2-Hydroxy-ethyl)-3,4-dihydro-2H-benzo[1,4]oxazine-7-carboxylic acid [5-(3-fluoro-benzenesulfonyl)-1,4,5,6-tetrahydro-pyrrolo[3,4-c]pyrazol-3-yl]-amide;
N-(5-Benzenesulfonyl-6,6-dimethyl-1,4,5,6-tetrahydro-pyrrolo[3,4-c]pyrazol-3-yl)-4-piperazin-1-yl-benzamide;
N-(5-Benzenesulfonyl-6,6-dimethyl-1,4,5,6-tetrahydro-pyrrolo[3,4-c]pyrazol-3-yl)-4-(4-methyl-piperazin-1-yl)-benzamide;
N-(5-Benzenesulfonyl-6,6-dimethyl-1,4,5,6-tetrahydro-pyrrolo[3,4-c]pyrazol-3-yl)-4-morpholin-4-yl-benzamide;
N-(5-Benzenesulfonyl-6,6-dimethyl-1,4,5,6-tetrahydro-pyrrolo[3,4-c]pyrazol-3-yl)-4-dimethylamino-benzamide;
N-[5-(2-Fluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
N-[5-(3-Fluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
N-[5-(3-Fluoro-benzenesulfonyl)-6,6-dimethyl-1,4,5,6-tetrahydro-pyrrolo[3,4-c]pyrazol-3-yl]-4-morpholin-4-yl-benzamide;
4-Dimethylamino-N-[5-(3-fluoro-benzenesulfonyl)-6,6-dimethyl-1,4,5,6-tetrahydro-pyrrolo[3,4-c]pyrazol-3-yl]-benzamide;
N-[5-(4-Fluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
N-[5-(3,4-Difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
N-[5-(3,5-Difluoro-benzenesulfonyl)-6,6-dimethyl-1,4,5,6-tetrahydro-pyrrolo[3,4-c]pyrazol-3-yl]-4-piperazin-1-yl-benzamide;
N-[5-(3,5-Difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
N-[5-(3,5-Difluoro-benzenesulfonyl)-6,6-dimethyl-1,4,5,6-tetrahydro-pyrrolo[3,4-c]pyrazol-3-yl]-4-(4-ethyl-piperazin-1-yl)-benzamide;
N-[5-(3,5-Difluoro-benzenesulfonyl)-6,6-dimethyl-1,4,5,6-tetrahydro-pyrrolo[3,4-c]pyrazol-3-yl]-4-(4-isopropyl-piperazin-1-yl)-benzamide;
4-(4-tert-Butyl-piperazin-1-yl)-N-[5-(3,5-difluoro-benzenesulfonyl)-6,6-dimethyl-1,4,5,6-tetrahydro-pyrrolo[3,4-c]pyrazol-3-yl]-benzamide;
4-(4-Cyclopropyl-piperazin-1-yl)-N-[5-(3,5-difluoro-benzenesulfonyl)-6,6-dimethyl-1,4,5,6-tetrahydro-pyrrolo[3,4-c]pyrazol-3-yl]-benzamide;
N-[5-(3,5-Difluoro-benzenesulfonyl)-6,6-dimethyl-1,4,5,6-tetrahydro-pyrrolo[3,4-c]pyrazol-3-yl]-4-morpholin-4-yl-benzamide;
N-[5-(3,5-Difluoro-benzenesulfonyl)-6,6-dimethyl-1,4,5,6-tetrahydro-pyrrolo[3,4-c]pyrazol-3-yl]-4-dimethylamino-benzamide;
N-[5-(3,5-Difluoro-benzenesulfonyl)-6,6-dimethyl-1,4,5,6-tetrahydro-pyrrolo[3,4-c]pyrazol-3-yl]-2-fluoro-4-(4-methyl-piperazin-1-yl)-benzamide;
N-[5-(3,5-Difluoro-benzenesulfonyl)-6,6-dimethyl-1,4,5,6-tetrahydro-pyrrolo[3,4-c]pyrazol-3-yl]-4-(4-methyl-piperazin-1-yl)-2-nitro-benzamide;
2-Amino-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
N-[5-(3,5-Difluoro-benzenesulfonyl)-6,6-dimethyl-1,4,5,6-tetrahydro-pyrrolo[3,4-c]pyrazol-3-yl]-3-fluoro-4-(4-methyl-piperazin-1-yl)-benzamide;
N-[5-(3,5-Difluoro-benzenesulfonyl)-6,6-dimethyl-1,4,5,6-tetrahydro-pyrrolo[3,4-c]pyrazol-3-yl]-4-(4-methyl-piperazin-1-yl)-3-nitro-benzamide;
2-Acetylamino-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
N-[5-(3,5-Difluoro-benzenesulfonyl)-6,6-dimethyl-1,4,5,6-tetrahydro-pyrrolo[3,4-c]pyrazol-3-yl]-2-isobutyrylamino-4-(4-methyl-piperazin-1-yl)-benzamide;
2-(Cyclobutanecarbonyl-amino)-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;
2-(2-Amino-acetylamino)-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

N-[5-(3,5-Difluoro-benzenesulfonyl)-6,6-dimethyl-1,4,5,6-tetrahydro-pyrrolo[3,4-c]pyrazol-3-yl]-2-(2-methylamino-acetylamino)-4-(4-methyl-piperazin-1-yl)-benzamide;

N-[5-(3,5-Difluoro-benzenesulfonyl)-6,6-dimethyl-1,4,5,6-tetrahydro-pyrrolo[3,4-c]pyrazol-3-yl]-2-(2-dimethylamino-acetylamino)-4-(4-methyl-piperazin-1-yl)-benzamide;

2-((S)-2-Amino-propionylamino)-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

(S)-Pyrrolidine-2-carboxylic acid [2-[5-(3,5-difluoro-benzenesulfonyl)-6,6-dimethyl-1,4,5,6-tetrahydro-pyrrolo[3,4-c]pyrazol-3-ylcarbamoyl]-5-(4-methyl-piperazin-1-yl)-phenyl]-amide;

(R)-Pyrrolidine-2-carboxylic acid [2-[5-(3,5-difluoro-benzenesulfonyl)-6,6-dimethyl-1,4,5,6-tetrahydro-pyrrolo[3,4-c]pyrazol-3-ylcarbamoyl]-5-(4-methyl-piperazin-1-yl)-phenyl]-amide;

N-[5-(3,5-Difluoro-benzenesulfonyl)-6,6-dimethyl-1,4,5,6-tetrahydro-pyrrolo[3,4-c]pyrazol-3-yl]-4-morpholin-4-yl-2-nitro-benzamide;

2-Amino-N-[5-(3,5-difluoro-benzenesulfonyl)-6,6-dimethyl-1,4,5,6-tetrahydro-pyrrolo[3,4-c]pyrazol-3-yl]-4-morpholin-4-yl-benzamide;

2-(2-Amino-acetylamino)-N-[5-(3,5-difluoro-benzenesulfonyl)-6,6-dimethyl-1,4,5,6-tetrahydro-pyrrolo[3,4-c]pyrazol-3-yl]-4-morpholin-4-yl-benzamide;

N-[5-(3,5-Difluoro-benzenesulfonyl)-6,6-dimethyl-1,4,5,6-tetrahydro-pyrrolo[3,4-c]pyrazol-3-yl]-2-(2-methylamino-acetylamino)-4-morpholin-4-yl-benzamide;

N-[5-(3,5-Difluoro-benzenesulfonyl)-6,6-dimethyl-1,4,5,6-tetrahydro-pyrrolo[3,4-c]pyrazol-3-yl]-2-(2-dimethylamino-acetylamino)-4-morpholin-4-yl-benzamide;

(S)-Pyrrolidine-2-carboxylic acid {2-[5-(3,5-difluoro-benzenesulfonyl)-6,6-dimethyl-1,4,5,6-tetrahydro-pyrrolo[3,4-c]pyrazol-3-ylcarbamoyl]-5-morpholin-4-yl-phenyl}-amide;

(R)-Pyrrolidine-2-carboxylic acid {2-[5-(3,5-difluoro-benzenesulfonyl)-6,6-dimethyl-1,4,5,6-tetrahydro-pyrrolo[3,4-c]pyrazol-3-ylcarbamoyl]-5-morpholin-4-yl-phenyl}-amide;

N-[5-(3,5-Difluoro-benzenesulfonyl)-6,6-dimethyl-1,4,5,6-tetrahydro-pyrrolo[3,4-c]pyrazol-3-yl]-4-dimethylamino-2-nitro-benzamide;

2-Amino-N-[5-(3,5-difluoro-benzenesulfonyl)-6,6-dimethyl-1,4,5,6-tetrahydro-pyrrolo[3,4-c]pyrazol-3-yl]-4-dimethylamino-benzamide;

2-(2-Amino-acetylamino)-N-[5-(3,5-difluoro-benzenesulfonyl)-6,6-dimethyl-1,4,5,6-tetrahydro-pyrrolo[3,4-c]pyrazol-3-yl]-4-dimethylamino-benzamide;

N-[5-(3,5-Difluoro-benzenesulfonyl)-6,6-dimethyl-1,4,5,6-tetrahydro-pyrrolo[3,4-c]pyrazol-3-yl]-4-dimethylamino-2-(2-methylamino-acetylamino)-benzamide;

N-[5-(3,5-Difluoro-benzenesulfonyl)-6,6-dimethyl-1,4,5,6-tetrahydro-pyrrolo[3,4-c]pyrazol-3-yl]-4-dimethylamino-2-(2-dimethylamino-acetylamino)-benzamide;

Pyrrolidine-2-carboxylic acid {2-[5-(3,5-difluoro-benzenesulfonyl)-6,6-dimethyl-1,4,5,6-tetrahydro-pyrrolo[3,4-c]pyrazol-3-ylcarbamoyl]-5-dimethylamino-phenyl}-amide;

4-Methyl-3,4-dihydro-2H-benzo[1,4]oxazine-7-carboxylic acid [5-(3,5-difluoro-benzenesulfonyl)-6,6-dimethyl-1,4,5,6-tetrahydro-pyrrolo[3,4-c]pyrazol-3-yl]-amide; and 4-(2-Hydroxy-ethyl)-3,4-dihydro-2H-benzo[1,4]oxazine-7-carboxylic acid [5-(3,5-difluoro-benzenesulfonyl)-6,6-dimethyl-1,4,5,6-tetrahydro-pyrrolo[3,4-c]pyrazol-3-yl]-amide.

As previously indicated, a further object of the present invention is represented by the process for preparing the compounds of Formula (I) and the pharmaceutically acceptable salts thereof, which process comprises:

a) reacting a compound of Formula (II) with a compound of Formula (III),

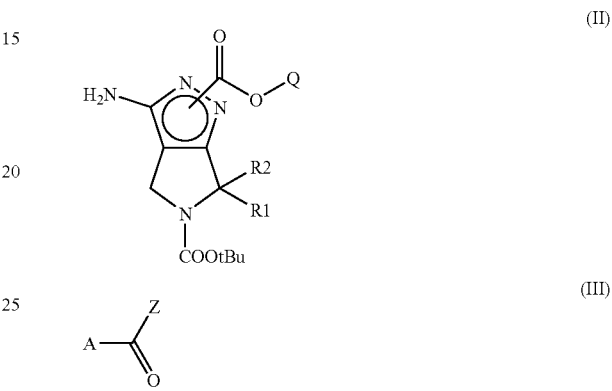

wherein A, $R^1$ and $R^2$ are as defined above, Q is a lower alkyl group, for instance a $(C_1-C_4)$alkyl group, more preferably methyl or ethyl, tbu represents tert-butyl and Z is hydroxy, halogen or a suitable leaving group, so as to obtain a compound of Formula (IV);

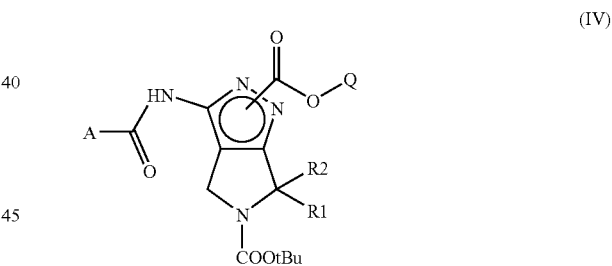

b) reacting a compound of Formula (IV), wherein A, $R^1$, $R^2$, and Q are as defined above, under acidic conditions so as to obtain a compound of Formula (V);

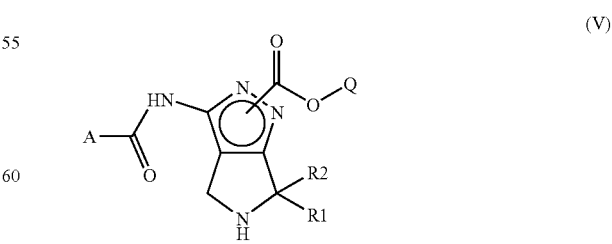

c) reacting a compound of formula (V), wherein A, $R^1$, $R^2$, and Q are as defined above, with a compound of Formula (VI),

(VI)

wherein R and Z are as defined above, so as to obtain a compound of Formula (VII);

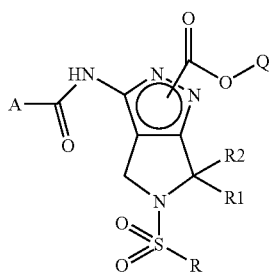

(VII)

d) reacting a compound of Formula (VII), wherein R, $R^1$, $R^2$, A, and Q are as defined above, under basic conditions so as to obtain the corresponding compound of Formula (I) and, if desired, converting it into a pharmaceutically acceptable salt thereof.

Alternatively, a compound of Formula (VII), as defined above, can be transformed into another compound of Formula (VII). Such transformation comprises:

e) converting a compound of Formula (VII), wherein R, $R^1$, $R^2$, and Q are as defined above, A is A1 or A2 and $R^5$ or $R^6$ is $NO_2$, into another compound of Formula (VII), wherein $R^5$ or $R^6$ is $NH_2$ and A1, A2, R, $R^1$, $R^2$, and Q are as defined above;

f) reacting the compound of Formula (VII) thus obtained, wherein A represents a residue of Formula (A1):

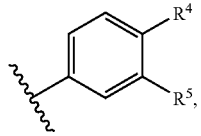

(A1)

R, $R^1$, $R^2$, $R^4$ and Q are as defined above and $R^5$ is $NH_2$, with a compound of Formula (VIII),

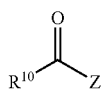

(VIII)

wherein $R^{10}$ and Z are as defined above, so as to obtain another compound of Formula (VII), wherein $R^5$ is $NHCOR^{10}$, and A, R, $R^{10}$, $R^1$, $R^2$, and Q are as defined above. Such compound can be reacted as described under d) to obtain a compound of Formula (I), which can be converted, if desired, into a pharmaceutically acceptable salt thereof. Alternatively, a compound of Formula (VII), wherein A represents a residue of Formula (A1), R, $R^1$, $R^2$, and Q are as defined above and $R^5$ is $NH_2$, can be first reacted as described under d) to obtain a compound of Formula (I) that can be further reacted with a compound of Formula (VIII) to obtain a compound of Formula (IX),

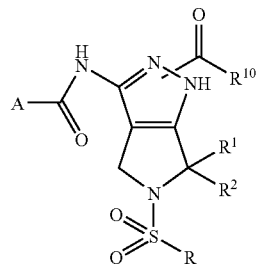

(IX)

wherein A, R, $R^1$, $R^2$, and $R^{10}$ are as defined above, and $R^5$ is $NHCOR^{10}$. A compound of Formula (IX) can be reacted as described under d) to obtain a compound of Formula (I), which can be converted, if desired, into a pharmaceutically acceptable salt thereof.

g) A compound of Formula (VII) can be reacted with a compound of Formula (X):

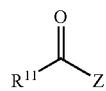

(X)

wherein $R^{11}$ and Z are as defined above; A represents a residue of Formula (A2):

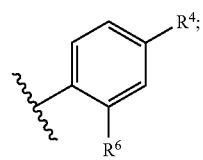

(A2)

R, $R^1$, $R^2$, $R^4$, and Q are as defined above, and $R^6$ is $NH_2$, so as to obtain another compound of Formula (VII), wherein $R^6$ is $NHCOR^{11}$, and A, R, $R^{11}$, $R^1$, $R^2$, and Q are as defined above. Such compound can be reacted as described under d) to obtain a compound of Formula (I), which can be converted, if desired, into a pharmaceutically acceptable salt thereof.

h) A compound of Formula (VII), wherein R, $R^1$, $R^2$, and Q are as defined above, A represents a residue of Formula (A1), $R^4$ is as defined above, and $R^5$ is $NH_2$, can then be reacted with a suitable aldehyde or ketone, so as to obtain another compound of Formula (VII), wherein R, $R^1$, $R^2$, Q are as defined above, A represents a residue of Formula (A1), $R^4$ is as defined above and $R^5$ is a $NR^8R^9$ group, wherein one of $R^8$ or $R^9$ is hydrogen and the other is an optionally further substituted straight or branched $(C_1-C_4)$alkyl. Such compound can then be reacted as described under d) to obtain a compound of Formula (I), which can be converted, if desired, into a pharmaceutically acceptable salt thereof.

Alternatively, a compound of Formula (VII), wherein R, $R^1$, $R^2$, and Q are as defined above, A represents a residue of Formula (A1), $R^4$ is as defined above and $R^5$ is $NH_2$, is first reacted as described under d) to obtain a compound of Formula (I), wherein R, $R^1$ and $R^2$ are as defined above, A represents a residue of Formula (A1), and $R^5$ is $NH_2$. Such compound is then reacted with a suitable aldehyde or ketone, as described above, to give another compound of Formula (I), wherein R, $R^1$ and $R^2$ are as defined above, A represents a residue of Formula (A1), $R^4$ is as defined above, and $R^5$ is a $NR^8R^9$ group, wherein one of $R^8$ or $R^9$ is hydrogen and the other is an optionally further substituted straight or branched ($C_1$-$C_4$)alkyl.

i) A compound of Formula (VII), wherein R, $R^1$, $R^2$, and Q are as defined above, A represents a residue of Formula (A1), $R^4$ is as defined above and $R^5$ is a $NR^8R^9$ group, wherein one of $R^8$ or $R^9$ is hydrogen and the other is an optionally further substituted straight or branched ($C_1$-$C_4$)alkyl, can then be reacted with a suitable aldehyde or ketone, so as to obtain another compound of Formula (VII) wherein $R^5$ is a $NR^8R^9$ group, wherein both $R^8$ and $R^9$ represent an optionally further substituted straight or branched ($C_1$-$C_4$)alkyl. Such compound can then be reacted as described under d) to obtain a compound of Formula (I) as defined above. Alternatively, the same procedure can be applied starting from a compound of Formula (I), wherein R, $R^1$ and $R^2$ are as defined above, A represents a residue of Formula (A1), $R^4$ is as defined above, and $R^5$ is a $NR^8R^9$ group, wherein one of $R^8$ or $R^9$ is hydrogen and the other is an optionally further substituted straight or branched ($C_1$-$C_4$)alkyl. It is to be noted that a compound of formula (II), (IV), (V) and (VII) as above defined can be in any one of its isomeric forms a or b:

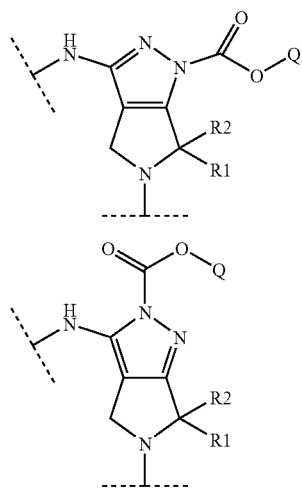

The synthesis of a compound of Formula (I), according to the synthetic process described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The following procedures provide non-limiting examples of preparations of the compounds of the present invention.

According to step (a) of the process, the reaction between a compound of Formula (II) and a compound of Formula (III) can be carried out in a variety of ways, according to conventional methods for acylating amino derivatives. As an example, a compound of Formula (II) can be reacted with an acyl chloride of Formula (III), wherein Z represents a chlorine atom. Preferably, this reaction is carried out in a suitable solvent such as, for instance, tetrahydrofuran, dichloromethane, toluene, diethyl ether, 1,4-dioxane, acetonitrile and in the presence of a proton scavenger such as triethylamine, pyridine, N,N-diisopropylethylamine, at a temperature ranging from room temperature to reflux, for a suitable time, typically from about 30 min. to about 96 hours.

According to step (b) of the process, the compound of Formula (IV) is easily deprotected at the dihydropyrrole nitrogen atom, by acidic treatment. This reaction can be conveniently carried out in the presence of a mineral or organic acid such as, for instance, hydrochloric, trifluoroacetic or methansulfonic acid, in a suitable solvent such as tetrahydrofuran, dichloromethane, 1,4-dioxane, a lower alcohol (e.g. methanol or ethanol), at a temperature ranging from room temperature to about 40° C. and for a time ranging from about 1 hour to about 96 hours.

The compound of Formula (V) thus obtained is further reacted, according to step (c) of the process, with a compound of Formula (VI). From the above it is clear to the skilled person that this sulfonylation reaction can be accomplished in a variety of ways and operative conditions, which are widely known in the art for the preparation of sulfonamides. As an example, the reaction between a compound of Formula (V) and a sulfonyl chloride (VI), wherein Z is a chlorine atom, can be carried out in a suitable solvent such as, for instance, diethyl ether, tetrahydrofuran, dichloromethane, chloroform, toluene, 1,4-dioxane, acetonitrile, and in the presence of a proton scavenger such as triethylamine, pyridine, N,N-diisopropylethylamine, at a temperature ranging from about –10° C. to reflux, for a suitable time, typically from about 30 min. to about 96 hours.

According to step (d) of the process, a compound of Formula (VII) is deprotected at the pyrazole nitrogen atom by working according to conventional methods enabling, for instance, the selective hydrolysis of the carbamate group. As an example, this reaction can be carried out under basic conditions, for instance in the presence of sodium hydroxide, potassium hydroxide or lithium hydroxide, or a tertiary amine such as triethylamine, and in a suitable solvent such as N,N-dimethylformamide, methanol, ethanol, tetrahydrofuran, water and mixtures thereof. Typically, the reaction is carried out at temperatures ranging from room temperature to about 60° C. and for a time ranging from about 30 minutes to about 96 hours.

According to step (e) of the process, a compound of Formula (VII), as defined above, can be converted into another compound of Formula (VII), wherein $R^5$ or $R^6$ is $NH_2$, in a variety of ways, according to conventional methods for reducing a nitro to an amino group. Preferably, this reaction is carried out in a suitable solvent such as, for instance, methanol, ethanol, water, tetrahydrofuran, 1,4-dioxane, N,N-dimethylformamide, acetic acid, or mixtures thereof, in the presence of a suitable reducing agent, such as for instance, hydrogen and a hydrogenation catalyst, or a metal such as iron or zinc in the present of an inorganic acid, such as hydrochloric acid, or by treatment with tin (II) chloride, or by treatment with cyclohexene, cyclohexadiene, formic acid or ammonium formate and a hydrogenation catalyst, at a temperature ranging from 0° C. to reflux and for a time ranging from about 1 hour to about 96 hours. The hydrogenation catalyst is usually a metal, most often palladium, which can be used as such or supported on carbon.

A compound of Formula (VII), wherein $R^5$ or $R^6$ is $NH_2$, or a compound of Formula (I), wherein $R^5$ or $R^6$ is $NH_2$, can be further reacted, according to step (f) or (g) of the process, with a compound of Formula (VIII) or (X), respectively. From the above it is clear to the skilled person that also this acylation reaction can be accomplished in a variety of ways and operative conditions, which are widely known in the art for the preparation of carboxamides. As an example, the reaction between a compound of Formula (VII) or a compound of Formula (I) and a carboxylic acid derivative of Formula (VIII) or (X), wherein Z is a suitable leaving group, can be carried out in the presence of a tertiary base, such as triethylamine, N,N-diisopropylethylamine or pyridine, in a suitable solvent, such as toluene, dichloromethane, chloroform, diethyl ether, tetrahydrofuran, 1,4-dioxane, acetonitrile, or N,N-dimethylformamide, at a temperature ranging from about −10° C. to reflux and for a period of time ranging from about 1 hour to about 96 hours. The compound of Formula (VII) or of Formula (IX) thus obtained can be reacted as described under d) to give a compound of Formula (I).

According to step (h) of the process, the reaction between a compound of Formula (VII), as defined above, and an aldehyde or a ketone can be carried out in a variety of ways, according to conventional methods for reductive alkylation. Preferably, this reaction is carried out in a suitable solvent such as, for instance, methanol, ethanol, N,N-dimethylformamide, dichloromethane, tetrahydrofuran, or a mixture thereof, in the presence of a suitable reducing agents such as, for instance, sodium borohydride, sodium cyano borohydride, sodium triacetoxy borohydride, hydrogen and a hydrogenation catalyst, and in the presence of an acid catalyst, such as, for instance, acetic acid, trifluoroacetic acid, at a temperature ranging from 0° C. to reflux and for a time ranging from about 1 hour to about 96 hours. This procedure can be repeated on a compound of Formula (VII), wherein R, $R^1$, $R^2$, and Q are as defined above, A represents a residue of Formula (A1), $R^4$ is as defined above, and $R^5$ is a $NR^8R^9$ group, wherein one of $R^8$ or $R^9$ is hydrogen and the other is an optionally further substituted straight or branched ($C_1$-$C_4$) alkyl, to obtain another compound of Formula (VII) wherein $R^5$ is a $NR^8R^9$ group, wherein both $R^8$ and $R^9$ represent an optionally further substituted straight or branched ($C_1$-$C_4$) alkyl.

In cases where a compound of Formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—*Enantiomers, Racemates, and Resolutions*, John Wiley & Sons Inc., New York (NY), 1981, which is incorporated herein for reference.

A compound of Formula (I) can also be transformed into a pharmaceutically acceptable salt according to standard procedures that are known to those skilled in the art. Alternatively, a compound of Formula (I) that is obtained as a salt can be transformed into the free base or the free acid according to standard procedures that are known to the skilled person.

The starting materials of the process of the invention are known or can be prepared according to known methods.

As an example, the preparation of a compound of Formula (II) wherein Q represents ethyl and $R^1$ and $R^2$ are each hydrogen is disclosed in the international application WO 02/12242 (see, in particular, example 26 at page 249; this same compound is therein named as 3-amino-4,6-dihydro-pyrrolo[3,4-c]pyrazole-1,5-dicarboxylic acid 5-tert-butyl ester 1-ethyl ester). Moreover, the preparation of a compound of Formula (II), wherein Q represents ethyl and $R^1$ and $R^2$ are methyl, is disclosed in the international application WO 04/056827 (see, in particular, example 6 at page 50; this same compound is therein named as 5-tert-butyl-1-ethyl-3-amino-6,6-dimethylpyrrolo[3,4-c]pyrazole-2,5(4H,6H)-dicarboxylate).

Additional compounds of Formula (II), wherein Q represents a lower alkyl group other than ethyl, can be prepared by applying procedures similar to those disclosed in the above mentioned patent applications.

The compounds of Formulae (III), (VIII) and (X), for instance those wherein Z represents a halogen atom, e.g. a chlorine atom, are either known or can be obtained from the corresponding carboxylic acids. These corresponding carboxylic acids are either known or can be prepared according to conventional methods.

The compounds of Formula (VI), for instance those wherein Z represents a halogen atom, e.g. a chlorine atom, are either known or can be prepared from sulfonic acids according to conventional methods.

Assays

Compounds of the present invention were tested in biochemical as well as in cell-based assays, as described below.

The short forms and abbreviations used have the following meaning

| | |
|---|---|
| Ci | Curie |
| DMSO | dimethylsulfoxide |
| ID | identity |
| KDa | kiloDalton |
| MicroCi | microCurie |
| mg | milligram |
| microg | microgram |
| mL | milliliter |
| microL | microliter |
| M | molar |
| mM | millimolar |
| microM | micromolar |
| nM | nanomolar |

Preparation of IGF-1R for Use in Biochemical Assay

Cloning and Expression

Human cDNA was used as template for amplification by polymerase chain reaction (PCR) of the whole cytoplasmic portion of IGF-1R (amino acid residues 960-1367), which includes the entire kinase domain. PCR was conducted using the forward primer sequence 5'-CTCGGATCCAGAAA-GAGAAATAACAGCAGGCTG-3' (SEQ ID NO: 1) and the reverse primer sequence 5'-CTCGGATCCTCAGCAGGTC-GAAGACTGGGGCAGCGG-3' (SEQ ID NO: 2). In order to facilitate subsequent cloning steps, both primers comprise a BamHI restriction endonuclease site sequence. The PCR product was cloned into a transfer vector for the baculovirus expression system, pVL1393 (Pharmingen), modified to include the sequence encoding the Glutathione S-transferase (GST) fusion protein and a PreScission cleavage site upstream of the inserted gene of interest. The GST-IGF-1R coding region corresponds to nucleic acid residues of 4168-6084. The final protein encoded by the open reading frame corresponds to a fusion protein of 639 amino acids, shown in SEQ ID NO: 3 (FIG. 1). This fusion protein consists essentially of an N-terminal GST/linker peptide moiety (amino acids 1-231 of SEQ ID NO: 3) and a C-terminal moiety representing the human IGF-1R intracellular domain (amino acids 232-639 of SEQ ID NO: 3). The fusion protein has a predicted molecular weight of 72.8 kDa. In order to obtain fusion protein, Sf21 insect cells (Invitrogen) were cotransfected with 2 microg of purified plasmid and 1 microg of virus DNA (BaculoGold™ Transfection Kit, Pharmingen), as described in the Baculovirus instruction manual (Pharmingen). A first amplification of the virus was performed using 600 microL of cotransfected virus on $6×10^6$ Sf21 in a monolayer culture, in 12 mL of medium (TNM-FH Grace's medium—Pharmingen). After 3 days the medium was collected, centrifuged and transferred to a sterile tube. A second amplification was prepared with the same method using 2 mL on $3\times10^7$ cells, diluted in 40 mL of medium. For the third amplification of virus, 1 mL of supernatant from the second round were used per $3\times10^7$ cells diluted in 40 mL of medium.

Protein expression was performed in H5 insect cells infected with 14 mL virus/$1\times10^9$ insect cells (MOI=1.5) for 65 h with shaking at 27° C. Cells were harvested by centrifugation at 1200×g for 10 minutes.

Protein Purification

Cells were resuspended in phosphate buffered saline solution (PBS), 20 mM dithiothreitol (DTT), CHAPS 0.2%, 20% glycerol, 1 mM OVA, "Complete" protease inhibitor cocktail (1 tablet/50 mL buffer; Roche Diagnostics, Milan, Italy) and lysed by liquid extrusion with a Gaulin homogenizer (Niro Soavi, Italy). The lysate was centrifuged at 14000×g for 45 minutes and the supernatant was loaded onto a column containing 10 mL Glutathione Sepharose (Amersham Biosciences). The column was first washed with PBS buffer for 5 column volumes, then with 100 mM Tris pH 8.0, 20% glycerol for 5 column volumes, and lastly eluted with 10 mM glutathione in 100 mM Tris pH 8.0, 20% glycerol. Fractions of 10 mL were collected, and protein-rich fractions were pooled. Typically, 20 mg of fusion protein were recovered from $1\times10^9$ cells, and this was typically >85% pure as judged by SDS-PAGE followed by Coomassie staining. Purified protein was stored at −80° C. prior to its use in biochemical assays.

Inhibition Assay for IGF-1R Kinase Activity

The inhibitory activity of putative kinase inhibitors and the potency of selected compounds was determined using a Scintillation Proximity Assay (SPA) in 96 well microtiter plate format. The assay is based on the ability of streptavidin-coated SPA beads to capture a biotinylated peptide containing a site that can be phosphorylated by IGF-1R kinase. When a radioactively labeled phosphate moiety is transferred by the kinase to the biotinylated peptide, this stimulates light emission by the bead, which is measured in a scintillation counter.

The buffers/components used in the assay were as follows. Kinase Buffer (buffer KB) was composed of 50 mM HEPES, 3 mM MnCl$_2$, 1 mM DTT, 3 microM Na$_3$VO$_4$, pH 7.9. Enzyme Buffer (buffer EB) was composed of buffer KB containing 0.6 mg/mL BSA (bovine serum albumin). SPA scintillation beads (Product Code Number RPNQ0007, Amersham Biosciences, Piscataway, N.J. USA) were prepared as a 10 mg/mL suspension in PBS containing 32 mM EDTA, 500 microM unlabeled ATP, and 0.1% Triton X-100. This preparation is referred to below as "SPA bead suspension". On the day of assay, IGF-1R was pre-phosphorylated in order to linearize reaction kinetics. To achieve this, the desired quantity of enzyme was incubated for 30 min at 28° C. at a concentration of 1050 nM enzyme in buffer EB containing 100 microM unlabeled ATP. After preincubation, and immediately before assay, this pre-phosphorylated IGF-1R kinase preparation was diluted to an enzyme concentration of 60 nM by addition of 16.5 volumes of buffer KB. This diluted prephosphorylated enzyme is referred to below as "enzyme mix".

The substrate used in the assay was a carboxy-terminally biotinylated peptide of the following sequence: KKKSPGEYVNIEFGGGGGK-biotin (SEQ ID NO: 4). The peptide was obtained in batches of >95% peptide purity from American Peptide Company, Inc. (Sunnyvale, Calif., USA). "ATP Mix", referred to below, consisted of buffer KB containing 6 nM $^{33}$Pγ-ATP (gamma phosphate-labeled, Redivue™ Code Number AH9968, 1000-3000 Ci/mmole, Amersham Biosciences Piscataway, N.J. USA), 18 microM unlabeled ATP, and 30 microM biotinylated substrate peptide. This solution contained these components at 3× their final reaction concentration. Compounds to be tested were prepared in 100% DMSO at appropriate concentrations. These preparations were then diluted 33-fold using buffer KB, so as to obtain compound at 3× the desired final assay concentration in buffer KB containing 3% DMSO. This 3× preparation is referred to below as "compound working solution".

Kinase Reaction:

Reactions were performed in 96-well U-bottom microtiter plates (such as Product #650101, Greiner Bio-One, Kremsmuenster Austria) in a final reaction volume of 30 microL. To each test well were added 10 microL of "compound working solution" containing appropriate dilution of compound, followed by 10 microL "ATP Mix" and 10 microL "Enzyme Mix", thus starting the reaction. Well contents were immediately mixed by pipetting, and reactions were incubated for 60 minutes at room temperature. After incubation, reactions were stopped by adding 100 microL/well "SPA bead suspension". Wells were incubated a further 15 minutes at room temperature, then 110 microL were withdrawn from each well and transferred to separate wells of 96-well opaque scintillation counting plates (such as OptiPlate™-96, PerkinElmer LAS, Inc. Boston, Mass., USA), each containing 100 microL/well 5M CsCl. After 4 hours resting at room temperature to allow SPA bead floatation, these plates were read using a scintillation counter (Packard TopCount NXT, PerkinElmer LAS, Inc. Boston, Mass., USA) in order to quantitate the light emitted from each well (proportional to the amount of phosphate incorporated into the substrate peptide during kinase reaction).

Many of the steps described above, such as those involving compound dilution, addition of mixes to the reaction, and transfer of completed reaction to counting plates can be automated using robotized pipetting stations (such as Multimek and Biomek liquid handlers, Beckman Coulter Inc., Fullerton Calif. USA), and a dilution curve of a known kinase inhibitor such as staurosporine can be routinely included as a positive control for IGF-1R inhibition.

Results: data were analyzed using the "Assay Explorer" software package (Elsevier MDL, San Leandro, Calif. 94577). For single compound concentrations, inhibitory activity was typically expressed as % inhibition obtained in presence of compound, compared to total activity of enzyme obtained when inhibitor is omitted.

Compounds showing desired inhibition can be further analyzed in order to study the potency of the inhibitor through IC$_{50}$ calculation. In this case, inhibition data obtained using serial dilutions of the inhibitor can be fitted by nonlinear regression using the following equation:

$$v = v_0 + \frac{(v_0 - v_b)}{1 + 10^{n(\log IC_{50} - \log[I])}}$$

where $v_b$ is the baseline velocity, v is the observed reaction velocity, $v_o$ is the velocity in the absence of inhibitors, and [I] is the inhibitor concentration.

Inhibition Assay for Aurora-2 Kinase Activity

The inhibiting activity and the potency of selected compounds was determined through a method of assay based on the use of the streptavidin scintillation proximity assay beads (Amersham-Pharmacia biotech) run in a 96 well plates. At the end of the reaction, the biotinylated peptide substrate was captured with the beads and subsequently allowed to stratify using CsCl.

When a radioactivity labeled phosphate moiety was transferred by the kinase to the beads-bound peptide, light emitted was measured in a scintillation counter.

The inhibition assay of Aurora-2 activity was performed in 96 wells plate according to the following protocol.

Kinase Reaction:

8 micro biotinylated peptide (4 repeats of LRRWSLG), 10 microM ATP (0.5 microCi $^{33}$Pγ-ATP), 10 nM Aurora2, 10 microM inhibitor in a final volume of 60 microL buffer (50 mM HEPES pH 7.0, 10 mM MgCl$_2$, 1 mM DTT, 0.125 mg/mL BSA, 3 microM orthovanadate) were added to each well of a 96 U bottom well plate. After 30-minute incubation at room temperature, reaction was stopped and biotinylated peptide captured by adding 100 microL of bead suspension.

Stratification:

100 microL of 7.5M CsCl were added to each well and let stand one hour before radioactivity was counted in the Top-Count instrument.

Results:

data were analyzed and expressed as % inhibition referred to total activity of enzyme (=100%).

All compounds showing inhibition ≥60% were further analyzed in order to study the potency of the inhibitor through IC$_{50}$ calculation.

The protocol used was the same described above, except that serial dilution of the inhibitor was used. Experimental data were fitted by nonlinear regression using the following equation:

$$v = v_0 + \frac{(v_0 - v_b)}{1 + 10^{n(\log IC_{50} - \log[I])}}$$

where $v_b$ is the baseline velocity, v is the observed reaction velocity, $v_o$ is the velocity in the absence of inhibitors, and [I] is the inhibitor concentration.

Western Blot Analysis of Receptor Phosphorylation Following Stimulation with IGF-1 in MCF-7 Human Breast Cancer Cells MCF-7 cells (ATCC #HTB-22) were seeded in 12-well tissue culture plates at 2×10$^5$ cells/well in E-MEM medium (MEM+Earle's BSS+2 mM glutamine+0.1 mM non-essential amino acids)+10% FCS, and incubated overnight at 37° C., 5% CO2, 100% relative humidity. Cells were then starved by replacing E-MEM+10% FCS with E-MEM+0.1% BSA, and incubating overnight. After this incubation, wells were treated with desired concentrations of compound for 1 hour at 37° C., and were then stimulated with 10 nM recombinant human IGF-1 (Invitrogen, Carlsbad, Calif., USA) for 10 minutes at 37° C. Cells were then washed with PBS and lysed in 100 microL/well cell lysis buffer (M-PER Mammalian Protein Extraction Reagent [Product #78501, Pierce, Rockford, Ill., USA]+10 mM EDTA+Protease inhibitor cocktail [Sigma-Aldrich product #P8340]+phosphatase inhibitor cocktail [Sigma-Aldrich products #P2850+#P5726]). Cell lysates were cleared by centrifugation at 10,000×g for 5 minutes, and 10 microg/lane of cleared lysate protein were run on NuPAGE gels (NuPAGE 4-12% 10-lane Bis-Tris gels, Invitrogen) with MOPS running buffer, then transferred onto Hybond-ECL nitrocellulose filters (Amersham Biosciences, Little Chalfont, Buckinghamshire, UK) using Mini PROTEAN II chambers (Blo-Rad Laboratories, Hercules, Calif., USA). Filters bearing transferred protein were incubated for 1 hour in blocking buffer (TBS+5% BSA+0.15% Tween 20), and probed for 2 hours in the same buffer containing 1/1000 rabbit anti-phospho IGF-1R Tyr1311/InsR Tyr1146 antibody (product #3021, Cell Signaling Technology, Beverly, Mass., USA) for the detection of phosphorylated IGF-1R, or 1/1000 dilution of rabbit IGF-Irβ(H-60) antibody (product #sc-9038, Santa Cruz Biotechnology, Inc., Santa Cruz, Calif., USA) for detecting total IGF-1R β chain. In either case, filters were then washed for 30 minutes with several changes of TBS+0.15% Tween 20, and incubated for 1 hour in washing buffer containing 1/5000 dilution of horseradish peroxidase conjugated anti-rabbit IgG (Amersham, product #NA934), then were washed again and developed using the ECL chemiluminescence system (Amersham) according to manufacturer's recommendations. Unless otherwise stated, reagents used were from Sigma-Aldrich, St. Louis, Mo., USA.

Growth Factor Induced S6 Ribosomal Protein Phosphorylation in Primary Human Fibroblasts.

Phosphorylation of S6 ribosomal protein in response to growth factor stimulation of normal human dermal fibroblasts (NHDF) was used to assess compound potency in inhibiting IGF-1 induced signal transduction in cells, and selectivity towards EGF and PDGF stimulus. NHDF cells obtained from PromoCell (Heidelberg, Germany), were maintained at 37° C. in a humidified atmosphere with 5% CO$_2$ in complete Fibroblast Growth Medium (PromoCell). For assay, NHDF were seeded in 384-well tissue culture plates (clear- and flat-bottomed black plates; Matrix Technologies Inc., Hudson, N.H., USA) at a density of 5000 cells/well in serum-free medium containing 0.1% bovine serum albumin (BSA) and incubated for 5 days. Starved cells were treated for 1 hour with desired doses of compounds and then stimulated for a further 2 hours with either 10 nM IGF-1 (Invitrogen Corp., CA, USA), 10 nM EGF (Gibco BRL, USA) or 1 nM PDGF-B/B (Roche Diagnostics GmbH, Germany). Cells were then fixed in PBS/3.7% paraformaldehyde for 20 minutes at room temperature, washed twice with PBS, and permeabilized with PBS/0.3% Triton X-100 for 15 minutes. Wells were then saturated with PBS/1% non-fat dry milk (Blo-Rad Laboratories, Hercules, Calif., USA) for 1 hour, and then probed for 1 hour at 37° C. with anti-phospho-S6 (Ser 235/236) antibody (Cell Signaling Technology, Beverly, Mass., USA, cat. #2211) at 1/200 dilution in PBS/1% milk/0.3% Tween 20. Wells were then washed twice with PBS, and incubated for 1 hour at 37° C. with PBS/1% milk/0.3% Tween 20+1 microg/mL DAPI (4,6-diamidino-2-phenylindole)+1/500 Goat anti-rabbit Cy5™-conjugated secondary antibody (Amersham Biosciences, Little Chalfont, Buckinghamshire, UK). Wells were then washed twice with PBS, and 40 microL PBS were left in each well for immunofluorescence analysis. Fluorescence images in the DAPI and Cy5™ channels were automatically acquired, stored and analysed using a Cellomics ArrayScan™ IV instrument (Cellomics, Pittsburgh, USA); the Cellomics Cytotoxicity Algorithm was used to quantify cytoplasmic fluorescence associated with phospho-S6 (Cy5™ signal parameter: "Mean Lyso Mass-pH") for each cell in 10 fields/well, and eventually expressed as a mean population value. Unless otherwise stated, reagents were obtained from Sigma-Aldrich, St, Louis, Mo., USA.

Biochemical and cell-based assay data for representative compounds are reported in Table 1.

TABLE 1

| Compound | IGF1R IC$_{50}$ (μM) Biochemical assay | Inhibition of IGF1R-induced S6 phosphorytation IC$_{50}$ (μM) |
|---|---|---|
| Example 24 | 0.34 | 3.05 |

The same compound was tested for inhibition of IGF1-induced IGF1R phosphorylation in MCF-7 cells and results are shown in FIG. 2.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the tablet form, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, eggs, silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations.

These pharmaceutical preparations may be manufactured in known manner, for example, by means of mixing, granulating, tabletting, sugar-coating, or film-coating processes. The liquid dispersions for oral administration may be, e.g., syrups, emulsions and suspensions. As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol.

The suspension or solutions for intramuscular injections may contain, together with the active compound, a pharmaceutically acceptable carrier, e.g., sterile water, olive oil, ethyl oleate, glycols, ergo propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

EXAMPLES

General Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 mL/min. Injection volume 10 μL. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water/0.01% trifluoroacetic acid, and mobile phase B was acetonitrile. Gradient from 10 to 90% B in 8 min, hold 90% B 2 min. Flow rate 20 mL/min. In alternative, mobile phase A was water/0.1% NH$_3$, and mobile phase B was acetonitrile. Gradient from 10 to 100% B in 8 min, hold 100% B 2 min. Flow rate 20 mL/min.

Example 1

Preparation of 4-(4-methyl-piperazin-1-yl)-2-nitro-benzoic acid

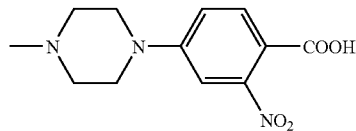 [SMILES: CN1CCN(c2ccc(C(=O)O)c([N+](=O)[O-])c2)CC1]

Step 1

Preparation of 4-fluoro-2-nitro-benzoic acid tert-butyl Ester

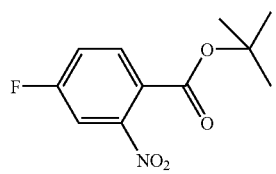

A solution of 4-fluoro-2-nitro-benzoic acid (10 g, 54 mmol), di-tert-butyl-dicarbonate (2 eq., 23.6 g, 108 mmol) and 4-(N,N-dimethylamino)pyridine (0.3 eq., 1.98 g, 16.2 mmol) in tert-butanol (100 mL) and dichloromethane (100 mL) was stirred at room temperature for 20 hours. The reaction mixture was then diluted with ethyl acetate (500 mL), washed with 1N HCl (500 mL), water (500 mL), brine (500 mL), dried over sodium sulphate and evaporated to dryness. The title compound was obtained as pale yellow oil (quantitative) and it was used in the next step without any further purification.

1H-NMR (400 MHz), δ (ppm, DMSO-$d_6$): 8.04 (dd, J=8.47, 2.50 Hz, 1H) 7.95 (dd, J=8.66, 5.37 Hz, 1H) 7.71 (ddd, J=8.66, 8.17, 2.56 Hz, 1H) 1.51 (s, 9H)

Step 2

Preparation of 4-(4-methyl-piperazin-1-yl)-2-nitro-benzoic acid tert-butyl Ester

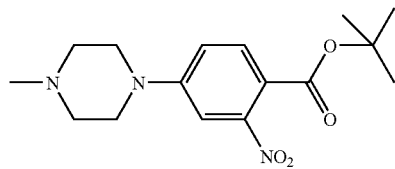 [SMILES: CN1CCN(c2ccc(C(=O)OC(C)(C)C)c([N+](=O)[O-])c2)CC1]

A solution of 4-fluoro-2-nitro-benzoic acid tert-butyl ester (13 g, 54 mmol) and N-methyl-piperazine (17 mL) was stirred at room temperature for 6 hours. The reaction mixture was then diluted with water (800 mL) and maintained under magnetic stirring for 20 hours. The resulting solid was filtered, washed thoroughly with water and dried under vacuum at 40° C. The title compound was obtained as yellow solid (16.4 g, 94% yield), and was used in the next step without any further purification.

1H-NMR (400 MHz), δ (ppm, DMSO-$d_6$): 7.69 (d, J=8.90 Hz, 1H) 7.29 (d, J=2.56 Hz, 1H), 7.15 (dd, J1=8.90 Hz, J2=2.56 Hz, 1H), 3.37 (m, 4H), 2.44 (m, 4H), 1.46 (s, 9H).

Based on Example 1, and using the suitable amine, the following compounds were obtained:

4-morpholin-4-yl-2-nitro-benzoic acid tert-butyl Ester

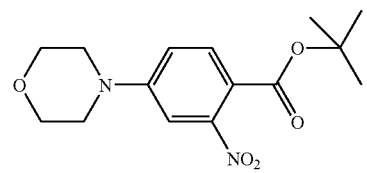 [SMILES: CC(C)(C)OC(=O)c1ccc(N2CCOCC2)cc1[N+](=O)[O-]]

1H-NMR (400 MHz), δ (ppm, DMSO-$d_6$): 7.71 (d, J=8.77 Hz, 1H), 7.31 (d, J=2.44 Hz, 1H), 7.17 (dd, J1=8.77 Hz, J2=2.44 Hz, 1H), 3.73 (m, 4H), 3.35 (m, 4H), 1.46 (s, 9H).

4-dimethylamino-2-nitro-benzoic acid tert-butyl Ester

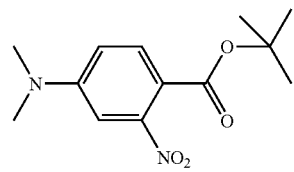 [SMILES: CN(C)c1ccc(C(=O)OC(C)(C)C)c([N+](=O)[O-])c1]

1H-NMR (400 MHz), δ (ppm, DMSO-$d_6$): 7.69 (d, J=8.90 Hz, 1H), 6.99 (d, J=2.68 Hz, 1H), 6.89 (dd, J1=8.90 Hz, J2=2.68 Hz, 1H), 3.04 (s, 6H), 1.46 (s, 9H).

Step 3

Preparation of 4-(4-methyl-piperazin-1-yl)-2-nitro-benzoic acid Hydrochloride

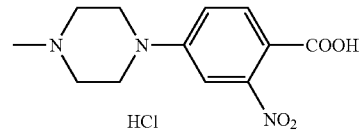

A mixture of tert-butyl 4-(4-methyl-piperazin-1-yl)-2-nitro benzoate (16.4 g, 51 mmol) and 37% HCl (100 mL) in 1,4-dioxane (200 mL) was stirred at room temperature for 4 hours. The resulting solid was filtered, washed thoroughly with 1,4-dioxane and dried under vacuum at 45° C. The title compound was obtained as a pale yellow solid (13.45 g, 87.5% yield) and it was used in the next step without any further purification.

1H-NMR (400 MHz), δ (ppm, DMSO-$d_6$): 10.27 (bs, 1H), 7.81 (d, J=8.90 Hz, 1H), 7.40 (d, J=2.69 Hz, 1H), 7.24 (dd, J1=8.90 Hz, J2=2.69 Hz, 1H), 4.13 (bs, 2H), 3.55-3.06 (bs, 6H), 2.83 (s, 3H).

Operating in an analogous way, the following compounds were obtained:

4-morpholin-4-yl-2-nitro-benzoic acid

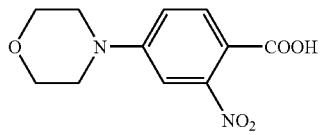 [SMILES: O=C(O)c1ccc(N2CCOCC2)cc1[N+](=O)[O-]]

1H-NMR (400 MHz), δ (ppm, DMSO-d$_6$): 12.98 (bs, 1H), 7.78 (d, J=8.91 Hz, 1H), 7.30 (d, J=2.44 Hz, 1H), 7.15 (dd, J1=8.91 Hz, J2=2.44 Hz, 1H), 3.73 (m, 4H), 3.33 (m, 4H).

4-dimethylamino-2-nitro-benzoic acid

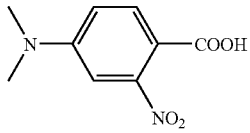

1H-NMR (400 MHz), δ (ppm, DMSO-d$_6$): 12.81 (bs, 1H), 7.72 (d, J=8.90 Hz, 1H), 6.96 (d, J=2.57 Hz, 1H), 6.84 (dd, J1=8.90 Hz, J2=2.58 Hz, 1H), 3.01 (s, 6H).

Example 2

Preparation of
4-(4-methyl-piperazin-1-yl)-3-nitro-benzoic acid

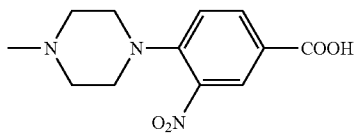

Step 1

Preparation of
4-(4-methyl-piperazin-1-yl)-3-nitro-benzoic acid Methyl Ester

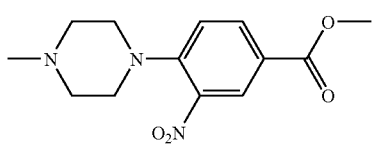

A mixture of 4-fluoro-3-nitro-benzoic acid methyl ester (10 g, 50.2 mmol), K$_2$CO$_3$ (7 g, 50.2 mmol) and 1-methyl-piperazine (11.2 mL, 100.4 mmol, 2 eq.) in 200 mL of N,N-dimethylformamide was stirred at 100° C. for 1 h. The solvent was then evaporated, the residue taken-up with water, extracted with ethyl acetate, dried over sodium sulphate and evaporated to dryness. The crude was purified by flash chromatography on silica gel, using a mixture dichloromethane-MeOH 9:1 as eluant, affording 14 g of the title compound as orange oil.

1H-NMR (400 MHz), δ (ppm, DMSO-d$_6$): 8.30 (d, J=2.1 Hz, 1H), 8.03 (dd, J1=2.1 Hz, J2=8.8 Hz, 1H), 7.36 (d, J=8.8 Hz, 1H), 3.86 (s, 3H), 3.18 (m, 4H), 2.49 (m, 4H), 2.27 (bs, 3H).

Step 2

Preparation of
4-(4-methyl-piperazin-1-yl)-3-nitro-benzoic acid Hydrochloride

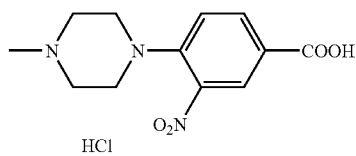 [SMILES: CN1CCN(c2ccc(C(=O)O)cc2[N+](=O)[O-])CC1 ; Cl]

A solution of 4-(4-methyl-piperazin-1-yl)-3-nitro-benzoic acid methyl ester (1.8 g, 6.4 mmol) in 35 mL of 5N HCl was stirred at 55° C. for 16 h. The reaction mixture was then evaporated to dryness affording the title compound (quantitative) that was used for the next step without any further purification.

1H-NMR (400 MHz), δ (ppm, DMSO-d$_6$): 13.09 (bs, 1H), 10.25 (bs, 1H), 8.38 (d, J=2.1 Hz, 1H), 8.10 (dd, J1=2.1 Hz, J2=8.8 Hz, 1H), 7.46 (d, J=8.8 Hz, 1H), 3.6-3.1 (m, 8H), 2.87 8 s, 3H).

By application of a procedure analogous to the one described above, the following compounds were prepared.

4-(4-Methyl-piperazin-1-yl)-3-trifluoromethyl-benzoic acid Hydrochloride

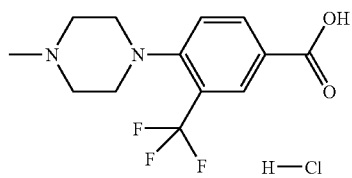 [SMILES: CN1CCN(c2ccc(C(=O)O)cc2C(F)(F)F)CC1 ; Cl]

4-(4-Methyl-piperazin-1-yl)-3-fluoro-benzoic acid Hydrochloride

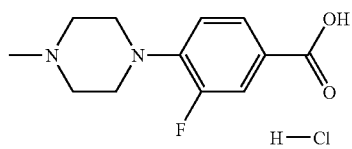

Step 1

4-(4-Methyl-piperazin-1-yl)-3-trifluoromethyl-benzoic acid Methyl Ester

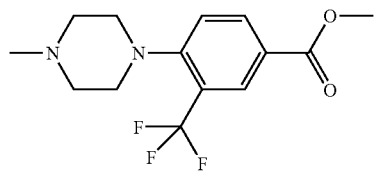

1H-NMR (400 MHz), δ (ppm, DMSO-d$_6$): 8.19-8.14 (m, 2H), 7.56 (d, J=8.3 Hz, 1H), 3.88 (s, 3H), 3.02 (m, 4H), 2.52 (m, 4H), 2.28 (s, 3H).

4-(4-Methyl-piperazin-1-yl)-3-fluoro-benzoic acid Methyl Ester

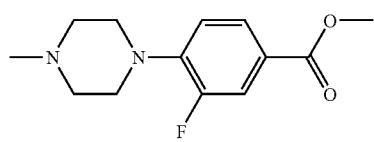

1H-NMR (400 MHz), δ (ppm, DMSO-d$_6$): 7.71 (dd, J1=1.9 Hz, J2=8.4 Hz, 1H), 7.60 (dd, J1=1.9 hz, J2=14.0 Hz, 1H), 7.12 (bt, J=8.7 Hz, 1H), 3.83 (s, 3H), 3.19 (m, 4H), 2.51 (m, 4H), 2.27 (bs, 3H).

Step 2

4-(4-Methyl-piperazin-1-yl)-3-trifluoromethyl-benzoic acid Hydrochloride

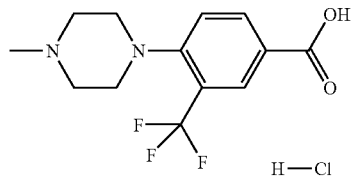 [SMILES: CN1CCN(c2ccc(C(=O)O)cc2C(F)(F)F)CC1 ; Cl]

1H-NMR (400 MHz), δ (ppm, DMSO-d$_6$): 10.17 (bs, 1H), 8.22 (dd, J1=2.0 Hz, J2=8.4 Hz, 1H), 8.18 (d, J=2.0 Hz, 1H), 7.64 (d, J=8.4 Hz, 1H), 3.60-3.05 (m, 8H), 2.89 (s, 3H).

4-(4-Methyl-piperazin-1-yl)-3-fluoro-benzoic acid Hydrochloride

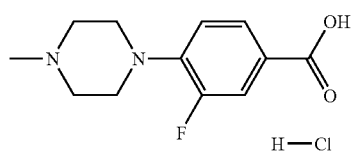

1H-NMR (400 MHz), δ (ppm, DMSO-d$_6$): 10.20 (bs, 1H), 7.73 (dd, J1=1.9 Hz, J2=8.3 Hz, 1H), 7.63 (dd, J1=1.9 Hz, J2=13.7 Hz, 1H), 7.19 (bt, J=8.7 Hz, 1H), 3.7-3.0 (m, 8H), 2.78 (s, 3H).

Example 3

Preparation of 2-fluoro-4-(4-methyl-piperazin-1-yl)-benzoic acid

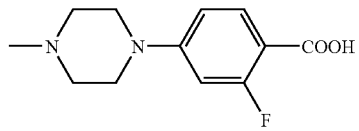 [SMILES: CN1CCN(c2ccc(C(=O)O)c(F)c2)CC1]

Step 1

Preparation of 2,4-difluoro-benzoic acid Methyl Ester

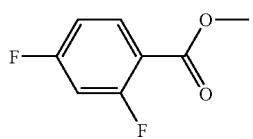

To 100 mL of methanol, 2,4-difluoro-benzoyl chloride (10 mL, 79.3 mmol) was added and the mixture stirred at room temperature for 2 hours. The solvent was then evaporated affording the title compound as pale yellow oil (quantitative).
1H-NMR (400 MHz), δ (ppm, DMSO-d$_6$): 8.0 (m, 1H), 7.44 (m, 1H), 7.25 (m, 1H), 3.87 (s, 3H).

Step 2

Preparation of 2-fluoro-4-(4-methyl-piperazin-1-yl)-benzoic acid Methyl Ester and 4-fluoro-2-(4-methyl-piperazin-1-yl)-benzoic acid Methyl Ester

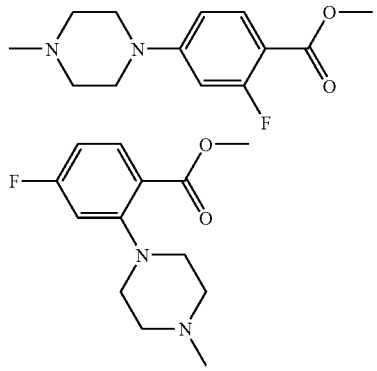

A mixture of 2,4-difluoro-benzoic acid methyl ester (4.5 g, 26.2 mmol), 1-methyl-piperazine (4.36 mL, 39.2 mmol, 1.5 eq.) and K$_2$CO$_3$ (3.62 g, 26.2 mmol, 1 eq.) in N,N-dimethylformamide (10 mL) was stirred at 100° C. for 4 hours. The mixture was then poured into 200 mL of water and extracted with 150 mL of EtOAc. The organic layer was separated, washed with water (100 mL) dried over sodium sulphate and evaporated to dryness. The crude was purified by flash chromatography on silica gel, using a mixture dichloromethane-MeOH-30% NH$_4$OH 95:5:0.5 as eluant, affording 1.65 g of 2-fluoro-4-(4-methyl-piperazin-1-yl)-benzoic acid methyl ester (first eluting, pale yellow solid) and 3.04 g of 4-fluoro-2-(4-methyl-piperazin-1-yl)-benzoic acid methyl ester (second eluting, yellow oil).

2-fluoro-4-(4-methyl-piperazin-1-yl)-benzoic acid Methyl Ester

1H-NMR (400 MHz), δ (ppm, DMSO-d$_6$): 7.72 (t, J=9.0 Hz, 1H), 6.84-6.74 (m, 2H), 3.78 (s, 3H), 3.4-3.3 (m, 4H), 2.46 (m, 4H), 2.25 (bs, 3H).

4-fluoro-2-(4-methyl-piperazin-1-yl)-benzoic acid Methyl Ester

1H-NMR (400 MHz), δ (ppm, DMSO-d$_6$): 7.68 (m, 1H), 6.88 (m, 1H), 6.80 (m, 1H), 3.80 (s, 3H), 3.01 (m, 4H), 2.49 (m, 4H), 2.27 (bs, 3H).

Step 3

Preparation of 2-fluoro-4-(4-methyl-piperazin-1-yl)-benzoic acid

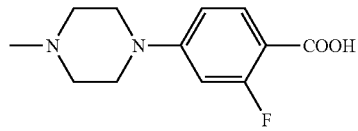 [SMILES: CN1CCN(c2ccc(C(=O)O)c(F)c2)CC1]

A mixture of methyl 4-(4-methylpiperazin-1-yl)-2-fluoro benzoate (800 mg, 3.17 mmol), 1N NaOH (6 mL) and MeOH (10 mL) was stirred at room temperature overnight, then 1N HCl (6 mL) was added. The solution was then evaporated to dryness affording a mixture of the title compound and NaCl that was used in the next step without any further purification.

Example 4

Preparation of 3-[(2-methoxy-ethyl)-methyl-amino]-4-(4-methyl-piperazin-1-yl)-benzoic acid

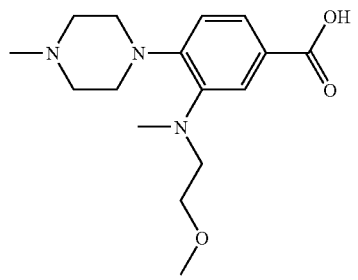 [SMILES: COCCN(C)c1cc(C(=O)O)ccc1N1CCN(C)CC1]

Step 1

Preparation of 3-bromo-4-(4-methyl-piperazin-1-yl)-benzoic acid Methyl Ester

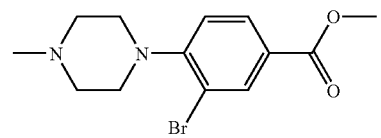

To a solution of 5 g (22.8 mmol) of 3-bromo-4-fluorobenzoic acid in 100 mL of methanol were added 1 mL of sulfuric acid and the reaction mixture was left standing at room temperature for 48 hours. The solvent is removed at reduced pressure, the residue taken up in dichloromethane, washed with saturated sodium hydrogencarbonate solution, water, brine and dried over anhydrous sodium sulfate. The solvent is evaporated and the residue used as such in the following step without purification.

The crude 3-bromo-4-fluorobenzoic acid methyl ester is dissolved in 120 mL of N,N-dimethylformamide, 4.32 g (43.1 mmol, 2 eq.) of N-methylpiperazine and 4.46 g (32.3 mmol, 1.5 eq.) of potassium carbonate were added and the reaction mixture heated at 80° C. for 8 hours. The mixture was poured into 300 mL of water and extracted with ethyl acetate. The organic phase was dried over sodium sulfate and evaporated to dryness.

1H-NMR (400 MHz), δ (ppm, DMSO-d$_6$): 8.08 (d, J=2.02 Hz, 1H), 7.91 (dd, J=2.02 Hz, 8.42 Hz, 1H), 7.25 (dd, J=8.42 Hz, 1H), 3.84 (s, 3H), 3.10 (m, 4H), 2.52 (m, 4H), 2.27 (s, 3H).

Step 2

Preparation of 3-(2-methoxy-ethylamino)-4-(4-methyl-piperazin-1-yl)-benzoic acid Methyl Ester

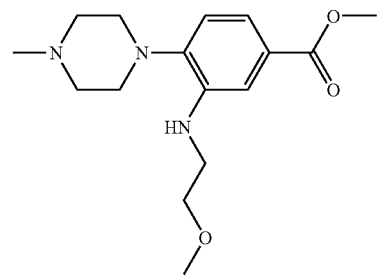

To a solution of 500 mg (1.59 mmol, 1 eq.) of 3-bromo-4-(4-methyl-piperazin-1-yl)-benzoic acid methyl ester in 5 mL of dry dioxane, in a double-necked round bottom flask, were added under argon atmosphere 780 mg (2.38 mmol, 1.5 eq.) of cesium carbonate, 30 mg of BINAP (0.047 mmol, 0.03 eq.), 14.55 mg of Pd$_2$(dba)$_3$ (0.0159 mmol, 0.1 eq.), 285 μL of 2-methoxy-ethanol-amine (1.4 eq.) and the resulting mixture was stirred at 100° C. for 48 h. The mixture was then evaporated and the residue purified by flash column chromatography, using dichloromethane-methanol 95:5 as eluant affording 280 mg of desired product.

1H-NMR (400 MHz), δ (ppm, DMSO-d$_6$): 7.29 (dd, J=1.97 Hz, 8.05 Hz, 1H), 7.15 (d, J=1.97 Hz, 1H), 7.04 (d, J=8.05 Hz, 1H), 4.93 (t, J=5.78 Hz, 1H), 3.81 (s, 3H), 3.58, (t, J=5.50 Hz, 2H), 3.31 (s, 3H), 3.26 (t, J=5.50 Hz, 2H), 2.88 (m, 4H), 2.55 (m, 4H), 2.30 (s, 3H).

Step 3

Preparation of 3-[(2-methoxy-ethyl)-methyl-amino]-4-(4-methyl-piperazin-1-yl)benzoic acid Methyl Ester

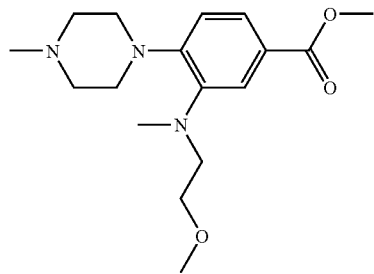

To a solution of 170 mg of 3-(2-methoxy-ethylamino)-4-(4-methyl-piperazin-1-yl)-benzoic acid methyl ester (0.55 mmol, 1 eq.) in 5 mL of acetic acid were added 3 mL of aqueous solution of formaldehyde and the resulting mixture stirred for 10 minutes at room temperature; a solution of NaCNBH$_3$ (680 mg, 11 mmol, 20 eq.) in 3 mL of MeOH was then added at 0° C. and the solution stirred for 5 minutes. The solvent was removed and the crude washed with water and dichloromethane. The combined organic layers were evaporated and the crude was purified by flash column chromatography, using dichloromethane-methanol 95:5 as eluant, affording 150 mg of the desired product.

1H-NMR (400 MHz), δ (ppm, DMSO-d$_6$): 7.52 (dd, J=2.04 Hz, 8.29 Hz, 1H), 7.49 (d, J=2.04 Hz, 1H), 6.97 (d, J=8.29 Hz, 1H), 3.81 (s, 3H), 3.34 (m, 11H), 2.81 (s, 3H), 2.52 (m, 4H), 2.29 (s, 3H).

Step 4

Preparation of 3-[(2-methoxy-ethyl)-methyl-amino]-4-(4-methyl-piperazin-1-yl)-benzoic acid

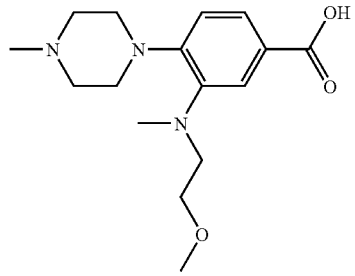 [SMILES: COCCN(C)c1cc(C(=O)O)ccc1N1CCN(C)CC1]

To a solution of 150 mg (0.47 mmol) of 3-[(2-methoxy-ethyl)-methyl-amino]-4-(4-methyl-piperazin-1-yl)-benzoic acid methyl ester in 5 mL of methanol were added 0.9 mL (0.93 mmol, 2 eq.) of 1N NaOH solution and the reaction mixture left standing overnight at room temperature. The solution was then added with 0.47 mL of 2N hydrochloric acid, the solvent evaporated, and the residue dried at 70° C. under vacuum. The compound was used as such in the subsequent step.

1H-NMR (400 MHz), δ (ppm, DMSO-d$_6$): 7.51 (m, 2H), 6.95 (d, J=8.35 Hz, 1H), 3.34 (m, 8H), 3.19 (s, 3H), 2.80 (s, 3H), 2.52 (m, 4H), 2.30 (s, 3H).

Example 5

Preparation of 6,6-dimethyl-3-[4-(4-methyl-piperazin-1-yl)-2-nitro-benzoylamino]-4H,6H-pyrrolo[3,4-c]pyrazole-2,6-dicarboxylic acid 5-tert-butyl ester 2-ethyl Ester

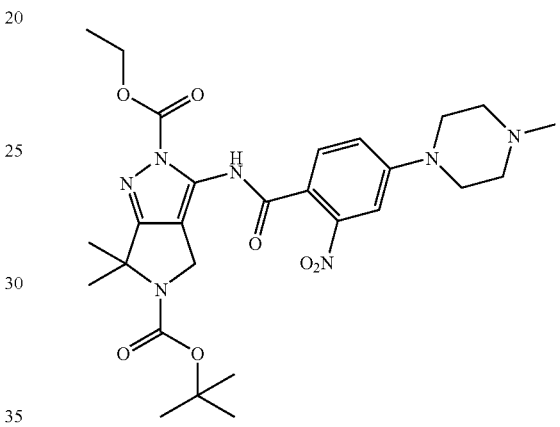

4-(4-methylpiperazin-1-yl)-2-nitro-benzoic acid (15 g, 49.7 mmol) in dry tetrahydrofuran (100 mL) was stirred with thionyl chloride (5 eq., 18.1 mL, 248.7 mmol) and a few drops of N,N-dimethylformamide at 80° C. for about 14 hours. After removal of the solvent under vacuum, the crude material was added portion-wise to a solution of 3-amino-6,6-dimethyl-4H,6H-pyrrolo[3,4-c]pyrazole-2,5-dicarboxylic acid 5-tert-butyl ester 2-ethyl ester (16.1 g, 49.7 mmol) and N,N-diethylisopropylamine (5 eq., 43.4 mL, 248.7 mmol) in 1,4-dioxane (200 mL) maintained under magnetic stirring at 80° C. The reaction mixture was stirred for about 6 hours at 80° C. After removal of the solvent, the crude material was diluted with dichloromethane (200 mL), washed with saturated sodium hydrogen carbonate solution (200 mL), dried over sodium sulphate, evaporated to dryness and purified by flash chromatography on silica gel using acetone as the eluant. The title compound was obtained as light yellow powder (13.5 g, 47% yield).

1H-NMR (400 MHz), δ (ppm, DMSO-d$_6$): 10.70, 10.67 (s, 1H), 7.68, 7.66 (d, J1=8.78 Hz, 1H), 7.48 (bs, 1H), 7.30 (dd, J1=8.78 Hz, J2=2.56 Hz, 1H), 4.47-4.39 (m, 4H), 3.41 (m, 4H), 2.52 (m, 4H), 2.27 (s, 3H), 1.63, 1.62 (s, 6H), 1.49, 1.46 (s, 9H), 1.37, 1.36 (t, J=7.07 Hz, 3H); mixture of rotamers.

Based on Example 5, and using the suitable acid chloride, the following compounds in Examples 6-15 were obtained:

Example 6

6,6-Dimethyl-3-[4-(4-methyl-piperazin-1-yl)-3-nitro-benzoylamino]-4H,6H-pyrrolo[3,4-c]pyrazole-2,5-dicarboxylic acid 5-tert-butyl ester 2-ethyl Ester

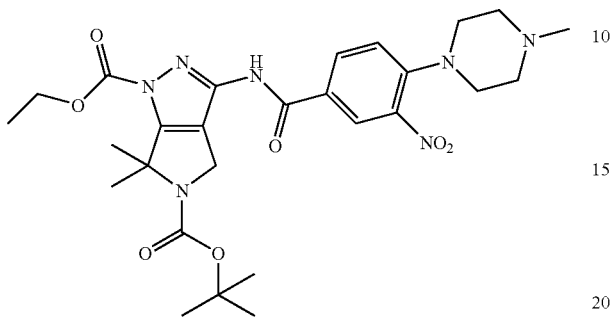

ESI(+) MS: m/z 572 (MH+).

Example 7

3-[2-Fluoro-4-(4-methyl-piperazin-1-yl)-benzoylamino]-6,6-dimethyl-4H,6H-pyrrolo[3,4-c]pyrazole-2,5-dicarboxylic acid 5-tert-butyl ester 2-ethyl Ester

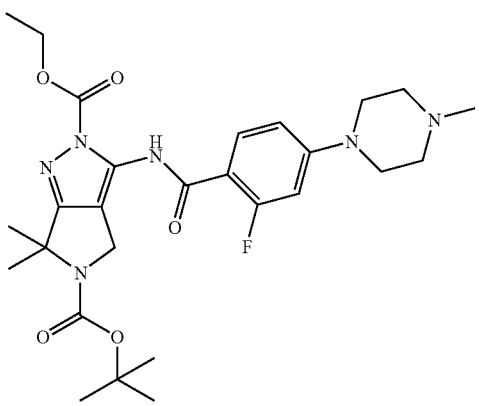 [SMILES: CCOC(=O)n1nc2c(c1NC(=O)c1ccc(N3CCN(C)CC3)cc1F)CN(C(=O)OC(C)(C)C)C2(C)C]

1H-NMR (400 MHz), δ (ppm, DMSO-$d_6$): 11.05, 11.02 (s, 1H), 7.86, 7.72 (m, 1H), 6.95-6.86, 6.83-6.75 (m, 2H), 4.61, 4.58 (s, 2H), 4.47 (q, J=7.07 Hz, 2H), 3.43-3.27 (m, 4H), 2.50-2.43 (m, 4H), 2.26 (bs, 3H), 1.63, 1.61 (s, 6H), 1.50, 1.48 (s, 9H), 1.38 (t, J=7.07 Hz, 3H); mixture of rotamers.

Example 8

3-[3-Fluoro-(4-methyl-piperazin-1-yl)-benzoylamino]-6,6-dimethyl-4,6-dihydro-pyrrolo[3,4-c]pyrazole-1,5-dicarboxylic acid 5-tert-butyl ester 1-ethyl Ester

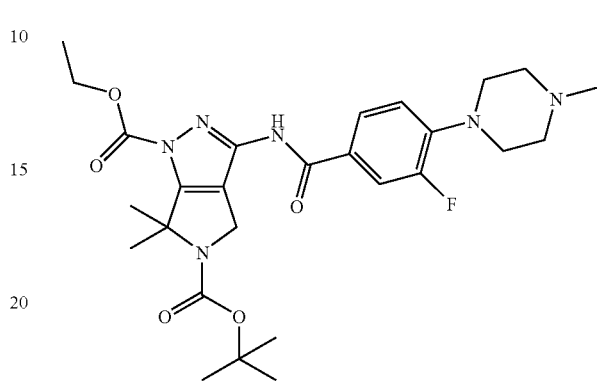

1H-NMR (400 MHz), δ (ppm, DMSO-$d_6$): 11.34 (s, 1H), 7.9-7.8 (m, 2H), 7.10 (m, 1H), 4.49 (bs, 2H), 4.45 (q, J=7.2 Hz, 2H), 73.18 (m, 4H), 2.52 (m, 4H), 2.27 (bs, 3H), 1.78, 1.77 (2 s, 6H), 1.50, 1.47 (2 s, 9H), 1.37 (t, J=7.2 Hz, 3H), mixture of rotamers.

Example 9

6,6-Dimethyl-3-(4-morpholin-4-yl-2-nitro-benzoylamino)-4H,6H-pyrrolo[3,4-c]pyrazole-2,5-dicarboxylic acid 5-tert-butyl ester 2-ethyl Ester

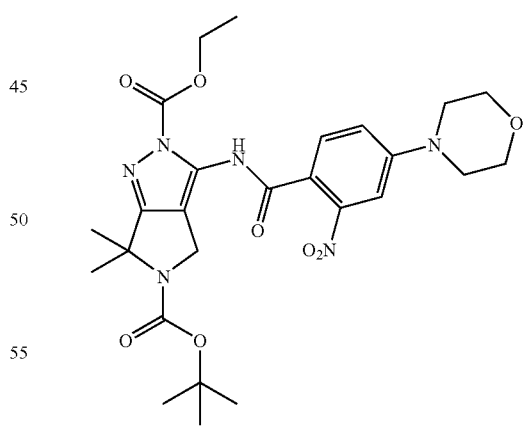

1H-NMR (400 MHz), δ (ppm, DMSO-$d_6$): 10.68 (s, 1H), 7.68, 7.66 (d, J=8.65 Hz, 1H), 7.47 (d, 1H), 7.29 (dd, J=8.65 Hz, J2=2.56 Hz, 1H), 4.45-4.36 (m, 4H), 3.73 (m, 4H), 3.34 (m, 4H), 1.61, 1.59 (s, 6H), 1.47, 1.43 (s, 9H), 1.34, 1.33 (t, J=7.08 Hz, 3H); mixture of rotamers.

Example 10

3-(4-Dimethylamino-2-nitro-benzoylamino)-6,6-dimethyl-4H,6H-pyrrolo[3,4-c]pyrazole-2,5-dicarboxylic acid 5-tert-butyl ester 2-ethyl Ester

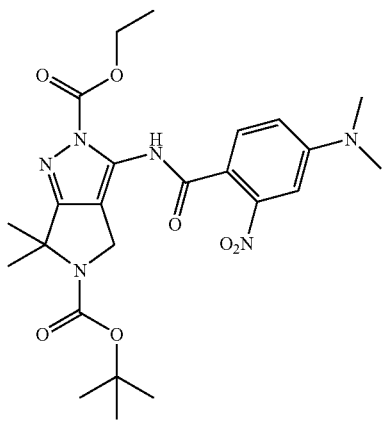

1H-NMR (400 MHz), δ (ppm, DMSO-$d_6$): 10.65, 10.62 (bs, 1H), 7.67, 7.66 (d, J1=8.70 Hz, 1H), 7.18 (bs, 1H), 7.01 (dd, J1=8.70 Hz, J2=2.56 Hz, 1H), 4.47-4.41 (m, 4H), 3.07 (s, 6H), 1.63, 1.61 (s, 6H), 1.49, 1.46 (s, 9H), 1.37, 1.36 (t, J=7.07 Hz, 3H); mixture of rotamers.

Example 11

3-[4-(4-Methyl-piperazin-1-yl)-2-trifluoromethyl-benzoylamino]-4,6-dihydro-pyrrolo[3,4-c]pyrazole-1,5-dicarboxylic acid 5-tert-butyl ester 1-ethyl Ester

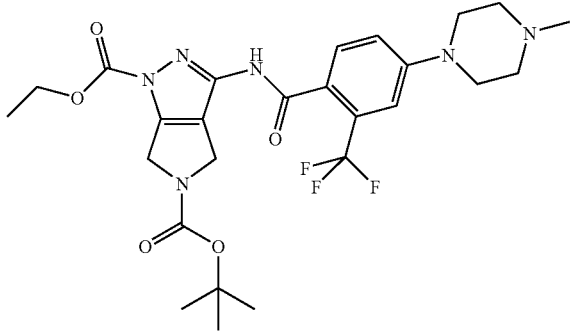 [SMILES: CCOC(=O)n1nc(NC(=O)c2ccc(N3CCN(C)CC3)cc2C(F)(F)F)c2c1CN(C(=O)OC(C)(C)C)C2]

1H-NMR (400 MHz), δ (ppm, DMSO-$d_6$): 11.39 (s, 1H), 7.52 (m, 1H), 7.21 (m, 2H), 4.60 (m, 2H), 4.47 (m, 2H), 4.40 (q, J=7.07 Hz, 2H), 3.41-3.27 (m, 4H), 2.53-2.46 (m, 4H), 2.27 (bs, 3H), 1.47, 1.46 (s, 9H), 1.35, 1.34 (t, J=7.07 Hz, 3H); mixture of rotamers.

Example 12

3-[4-(4-Methyl-piperazin-1-yl)-3-trifluoromethyl-benzoylamino]-4,6-dihydro-pyrrolo[3,4-c]pyrazole-1,5-dicarboxylic acid 5-tert-butyl ester 1-ethyl Ester

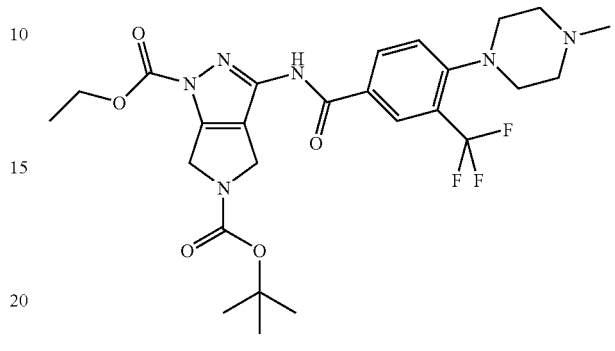

1H-NMR (400 MHz), δ (ppm, DMSO-$d_6$): 11.67 (s, 1H), 8.38, 8.30, 8.14 (3 m, 2H), 7.55 (m, 1H), 4.62 (m, 2H), 4.53 (m, 2H), 4.42 (q, J=7.0 Hz, 2H), 3.00 (m, 4H), 2.50 (m, 4H), 2.26 (bs, 3H), 1.48 (bs, 9H), 1.36, 1.35 (2 t, J=7.0 Hz, 3H), mixture of rotamers.

Example 13

3-[4-(4-Methyl-piperazin-1-yl)-3-nitro-benzoylamino]-4,6-dihydro-pyrrolo[3,4-c]pyrazole-1,5-dicarboxylic acid 5-tert-butyl ester 1-ethyl Ester

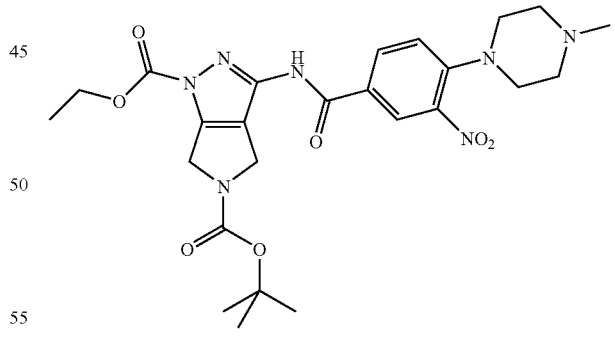

1H-NMR (400 MHz), δ (ppm, DMSO-$d_6$): 11.58 (s, 1H), 8.56 (m, 1H), 8.21 (dd, J1=2.3 Hz, J2=8.9 Hz, 1H), 7.36 (dd, J1=2.6 Hz, J1=8.9 Hz, 1H), 4.61 (m, 2H), 4.53 (m, 2H), 4.41 (q, J=7.2 Hz, 2H), 3.17 (m, 4H), 2.47 (m, 4H), 2.26 (bs, 3H), 1.48 (s, 9H), 1.36 (t, J=7.1 Hz, 3H).

Example 14

3-[3-[(2-Methoxy-ethyl)-methyl-amino]-4-(4-methyl-piperazin-1-yl)-benzoylamino]-4,6-dihydro-pyrrolo[3,4-c]pyrazole-1,5-dicarboxylic acid 5-tert-butyl ester 1-ethyl Ester

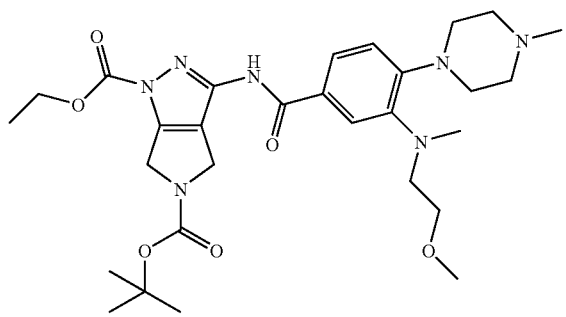 [SMILES: CCOC(=O)n1nc(NC(=O)c2ccc(N3CCN(C)CC3)c(N(C)CCOC)c2)c2c1CN(C(=O)OC(C)(C)C)C2]

ESI(+) MS: m/z 586 (MH$^+$).

Example 15

6,6-Dimethyl-3-[4-(4-methyl-piperazin-1-yl)-benzoylamino]-4H,6H-pyrrolo[3,4-c]pyrazole-2,5-dicarboxylic acid 5-tert-butyl ester 2-ethyl Ester

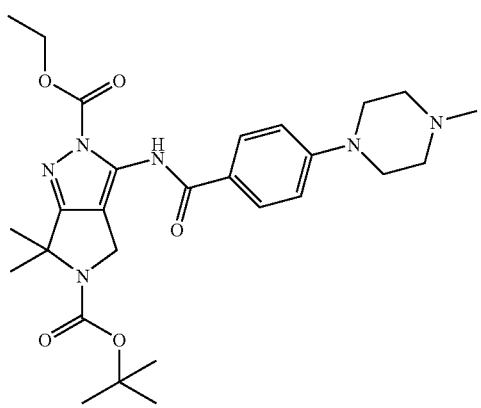 [SMILES: CCOC(=O)n1nc2c(c1NC(=O)c1ccc(N3CCN(C)CC3)cc1)CN(C(=O)OC(C)(C)C)C2(C)C]

1H-NMR (400 MHz), δ (ppm, DMSO-d$_6$): 10.69 (s, 1H), 7.76 (m, 2H), 7.08 (m, 2H), 4.55 (m, 2H), 4.48 (q, J=7.1 Hz, 2H), 3.35 (m, 4H), 2.50 (m, 4H), 2.27 (bs, 3H), 1.62, 1.63 (2 s, 6H), 1.50, 1.47 (2 s, 9H), 1.38 (t, J=7.1 Hz, 3H); mixture of rotamers.

Example 16

Preparation of 6,6-dimethyl-3-[4-(4-methyl-piperazin-1-yl)-2-nitro-benzoylamino]-5,6-dihydro-4H-pyrrolo[3,4-c]pyrazole-2-carboxylic acid ethyl ester dihydrochloride

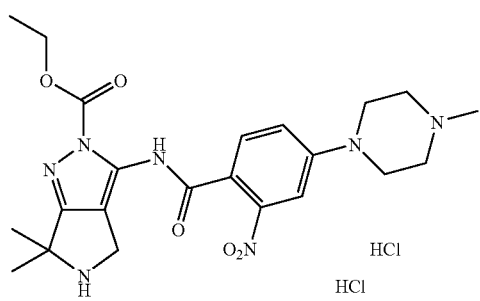 [SMILES: CCOC(=O)n1nc2c(c1NC(=O)c1ccc(N3CCN(C)CC3)cc1[N+](=O)[O-])CNC2(C)C ; Cl ; Cl]

A solution of 4N HCl in 1,4-dioxane (4 eq., 18.4 mL, 73.6 mmol) was added to a stirred solution of 6,6-dimethyl-3-[4-(4-methyl-piperazin-1-yl)-2-nitro-benzoylamino]-4H,6H-pyrrolo[3,4-c]pyrazole-2,5-dicarboxylic acid 5-tert-butyl ester 2-ethyl ester (10.5 g, 18.4 mmol) in 1,4-dioxane (100 mL) at room temperature. Stirring was continued for 30 hours. After removal of the solvent, the crude material was treated with diethyl ether (2×100 mL) and evaporated to dryness. The title compound was obtained after crystallization from diethyl ether as yellow solid (10 g, quantitative).

1H-NMR (400 MHz), δ (ppm, DMSO-d$_6$): 10.88 (s, 2H), 9.94 (bs, 1H), 7.75 (d, J1=8.78 Hz, 1H), 7.61 (d, J2=2.56 Hz, 1H), 7.40 (dd, J1=8.78 Hz, J2=2.56 Hz, 1H), 4.50-4.43 (m, 4H), 4.14 (m, 2H), 3.51 (m, 2H), 3.45-3.05 (m, 4H), 2.84 (s, 3H), 1.69 (s, 6H), 1.37 (t, J=7.07 Hz, 3H).

Based on Example 16, the following compounds in Examples 17-26 were obtained:

Example 17

6,6-Dimethyl-3-[4-(4-methyl-piperazin-1-yl)-3-nitro-benzoylamino]-5,6-dihydro-4H-pyrrolo[3,4-c]pyrazole-2-carboxylic acid ethyl ester dihydrochloride

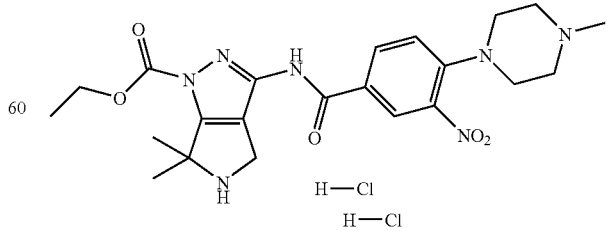

ESI(+) MS: m/z 472 (MH$^+$).

Example 18

6,6-Dimethyl-3-(4-morpholin-4-yl-2-nitro-benzoylamino)-5,6-dihydro-4H-pyrrolo[3,4-c]pyrazole-2-carboxylic acid ethyl ester hydrochloride

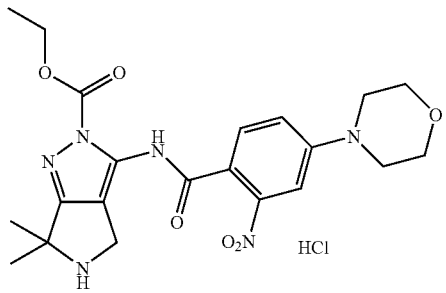 [SMILES: CCOC(=O)n1nc2c(c1NC(=O)c1ccc(N3CCOCC3)cc1[N+](=O)[O-])CNC2(C)C ; Cl]

1H-NMR (400 MHz), δ (ppm, DMSO-d$_6$): 10.56 (s, 1H), 768 (d, J1=8.66 Hz, 1H), 7.46 (d, J2=2.44 Hz, 1H), 7.29 (dd, J1=8.66 Hz, J2=2.44 Hz, 1H), 4.40 (q, J=7.07 Hz, 2H), 3.88 (s, 2H), 3.75 (m, 4H), 3.34 (m, 4H), 1.37-1.32 (m, 9H).

Example 19

3-(4-Dimethylamino-2-nitro-benzoylamino)-6,6-dimethyl-5,6-dihydro-4H-pyrrolo[3,4-c]pyrazole-2-carboxylic acid ethyl ester hydrochloride

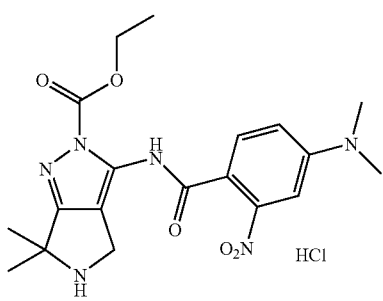

1H-NMR (400 MHz), δ (ppm, DMSO-d$_6$): 10.78 (s, 1H), 9.83 (bs, NH$_2^+$), 7.67 (d, J1=8.90 Hz, 1H), 7.18 (d, J2=2.56 Hz, 1H), 7.02 (dd, J1=8.90 Hz, J2=2.56 Hz, 1H), 4.50 (m, 2H), 4.47 (q, J=7.08 Hz, 2H), 3.08 (s, 6H), 1.68 (s, 6H), 1.38 (t, J=7.08 Hz, 3H).

Example 20

3-[2-Fluoro-4-(4-methyl-piperazin-1-yl)-benzoylamino]-6,6-dimethyl-5,6-dihydro-4H-pyrrolo[3,4-c]pyrazole-2-carboxylic acid ethyl ester dihydrochloride

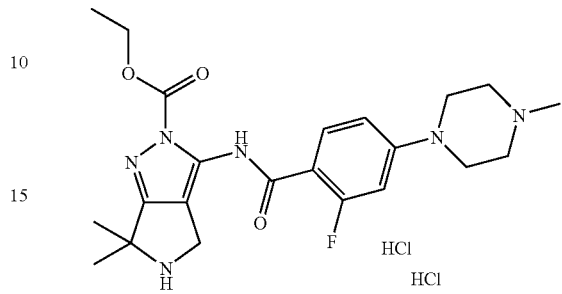

1H-NMR (400 MHz), δ (ppm, DMSO-d$_6$): 11.13, 11.10 (s, 1H), 7.91, 7.78 (m, 1H), 7.06-7.00, 6.94-6.89 (m, 2H), 4.64, 4.63 (bs, 2H), 4.49 (q, J=7.08 Hz, 2H), 4.17-4.12 (m, bs, 2H), 3.55-3.49 (m, bs, 2H), 3.41-3.28 (m, bs, 2H), 3.17-3.07 (m, bs, 2H), 2.87, 2.83 (bs, 3H), 1.68, 1.65 (s, 6H), 1.39 (t, J=7.08 Hz, 3H); mixture of rotamers.

Example 21

3-[4-(4-Methyl-piperazin-1-yl)-2-trifluoromethyl-benzoylamino]-5,6-dihydro-4H-pyrrolo[3,4-c]pyrazole-1-carboxylic acid ethyl ester dihydrochloride

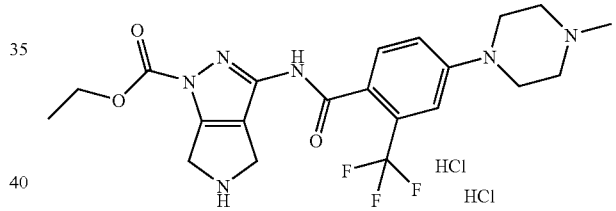

1H-NMR (400 MHz) δ (ppm, DMSO-d$_6$): 11.64 (s, 1H), 10.23 (bs, NH$_2^+$), 7.61 (d, J1=8.66 Hz, 1H), 7.35 (d, bs, J22=2.31 Hz, 1H), 7.30 (dd, J1=8.66 Hz, J2=2.31 Hz, 1H), 4.56 (m, bs, 2H), 4.45-4.40 (m, 4H), 4.09 (m, bs, 2H), 3.52 (m, bs, 2H), 3.26-3.09 (m, bs, 4H), 2.85, 2.84 (s, 3H), 1.36 (t, J=7.07 Hz, 3H), mixture of rotamers.

Example 22

3-[4-(4-Methyl-piperazin-1-yl)-3-trifluoromethyl-benzoylamino]-5,6-dihydro-4H-pyrrolo[3,4-c]pyrazole-1-carboxylic acid ethyl ester dihydrochloride

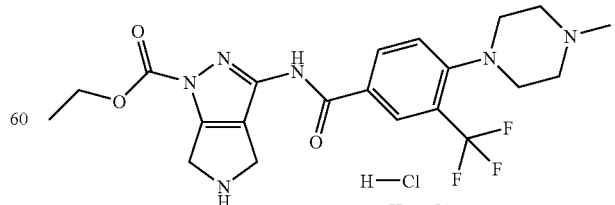

1H-NMR (400 MHz), δ (ppm, DMSO-d$_6$): 11.90, 10.45, 10.27, 10.17 (4 bs, 4H), 8.43 (m, 1H), 8.36 (m, 1H), 7.65 (m, 1H), 4.58 (m, 2H), 4.50 (m, 2H), 4.44 (q, J=7.1 Hz, 2H), 3.5-3.1 (m, 8H), 2.89 (bs, 3H), 1.37 (t, J=7.1 Hz, 3H).

Example 23

3-[4-(4-Methyl-piperazin-1-yl)-3-nitro-benzoylamino]-5,6-dihydro-4H-pyrrolo[3,4-c]pyrazole-1-carboxylic acid ethyl ester hydrochloride

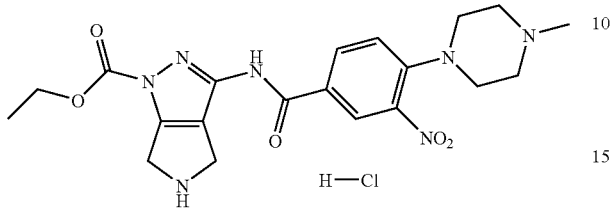

1H-NMR (400 MHz), δ (ppm, DMSO-d$_6$): 11.83 (s, 1H), 10.58, 10.20, 10.05 (3 bs, 2H), 8.65 (d, J=2.3 Hz, 1H), 8.28 (dd, J1=2.3 Hz, J2=8.9 Hz, 1H), 7.49 (d, J=8.9 Hz, 1H), 4.57 (m, 2H), 4.49 (m, 2H), 4.44 (q, J=7.1 Hz, 2H), 3.6-3.45 (m, 4H), 3.35-3.1 (m, 4H), 2.87 (bs, 3H), 1.37 (t, J=7.1 Hz, 3H).

Example 24

3-[3-[(2-Methoxy-ethyl)-methyl-amino]-4-(4-methyl-piperazin-1-yl)-benzoylamino]-5,6-dihydro-4H-pyrrolo[3,4-c]pyrazole-1-carboxylic acid ethyl ester hydrochloride

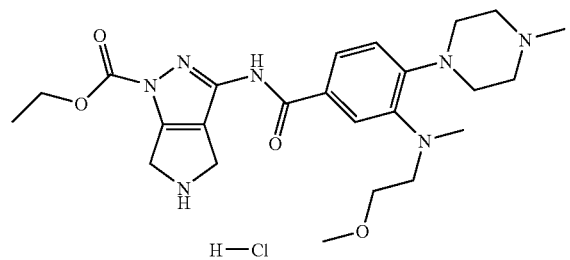 [SMILES: CCOC(=O)n1nc(NC(=O)c2ccc(N3CCN(C)CC3)c(N(C)CCOC)c2)c2c1CNC2 ; Cl]

ESI(+) MS: m/z 486 (MH$^+$).

Example 25

6,6-Dimethyl-3-[4-(4-methyl-piperazin-1-yl)-benzoylamino]-5,6-dihydro-4H-pyrrolo[3,4-c]pyrazole-2-carboxylic acid ethyl ester dihydrochloride

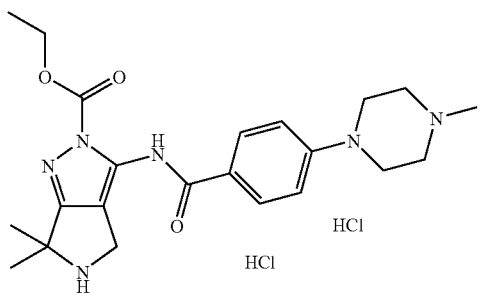 [SMILES: CCOC(=O)n1nc2c(c1NC(=O)c1ccc(N3CCN(C)CC3)cc1)CNC2(C)C ; Cl ; Cl]

1H-NMR (400 MHz), δ (ppm, DMSO-d$_6$): 11.39 (s, 1H), 10.68 (bs, 1H), 10.22 (bs, 2H), 8.00 (m, 2H), 7.10 (m, 2H), 4.51 (m, 2H), 4.47 (q, J=7.1 Hz, 2H), 4.12-4.03 (m, 2H), 3.49 (m, 2H), 3.28-3.06 (m, 4H), 2.84, 2.83 (2 bs, 3H), 1.80 (bs, 6H) 1.37 (t, J=7.1 Hz, 3H).

Example 26

3-[3-Fluoro-4-(4-methyl-piperazin-1-yl)-benzoylamino]-6,6-dimethyl-5,6-dihydro-4H-pyrrolo[3,4-c]pyrazole-1-carboxylic acid ethyl ester

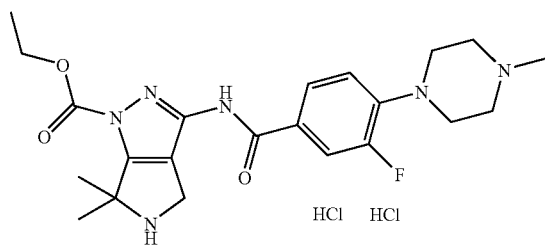 [SMILES: CCOC(=O)n1nc(NC(=O)c2ccc(N3CCN(C)CC3)c(F)c2)c2c1C(C)(C)NC2 ; Cl ; Cl]

1H-NMR (400 MHz), δ (ppm, DMSO-d$_6$): 11.60 (s, 1H), 10.60 (bs, 1H), 10.19 (bs, 2H), 7.94-7.88 (m, 2H), 7.23 (m, 1H), 4.51 (bs, 2H), 4.47 (q, J=7.2 Hz, 2H), 3.76-3.44 (m, 4H), 3.23 (m, 4H), 2.85 (bs, 3H), 1.80 (s, 6H), 1.37 (t, J=7.2 Hz, 3H).

Example 27

Preparation of 5-(3,5-difluoro-benzenesulfonyl)-6,6-dimethyl-3-[4-(4-methyl-piperazin-1-yl)-2-nitro-benzoylamino]-5,6-dihydro-4H-pyrrolo[3,4-c]pyrazole-2-carboxylic acid ethyl ester

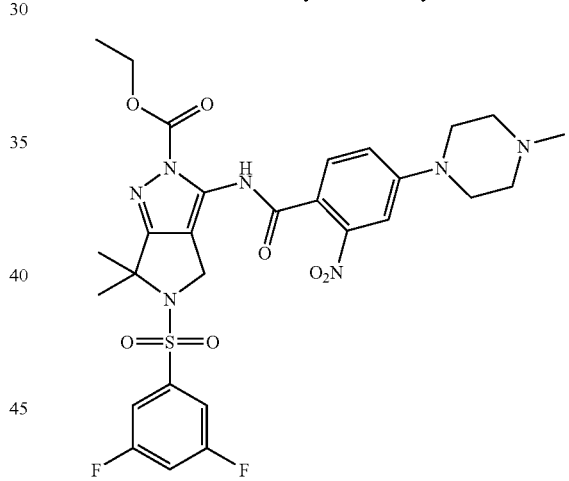

3,5-difluoro-benzenesulfonyl chloride (1 eq., 3.9 g, 18.4 mmol) was added portion-wise to a stirred solution of 6,6-dimethyl-3-[4-(4-methyl-piperazin-1-yl)-2-nitro-benzoylamino]-5,6-dihydro-4H-pyrrolo[3,4-c]pyrazole-2-carboxylic acid ethyl ester dihydrochloride (10 g, 18.4 mmol) and N,N-diisopropylethylamine (6 eq, 19.3 mL, 110.4 mmol) in dry dichloromethane (100 mL) at room temperature. Stirring was continued for about 4 hours. The reaction mixture was diluted with dichloromethane (100 mL) then washed with saturated sodium hydrogen carbonate (150 mL), dried over sodium sulphate, evaporated to dryness and purified by flesh chromatography on silica gel using acetone as the eluant. The title compound was obtained as yellow solid (9 g, 65% yield).

1H-NMR (400 MHz), δ (ppm, DMSO-d$_6$): 10.71 (s, 1H), 7.69-7.62 (m, 4H), 7.47 (d, J2=2.44 Hz, 1H), 7.29 (dd, J1=9.03 Hz, J2=2.44 Hz, 1H), 4.58 (s, 2H), 4.43 (q, J=7.07 Hz, 2H), 3.41 (m, 4H), 2.50 (m, 4H), 2.26 (s, 3H), 1.67 (s, 6H), 1.35 (t, J=7.07 Hz, 3H).

Based on Example 27, the following compounds in Examples 28-38 were obtained:

Example 28

5-(3,5-Difluoro-benzenesulfonyl)-6,6-dimethyl-3-[4-(4-methyl-piperazin-1-yl)-3-nitro-benzoylamino]-5,6-dihydro-4H-pyrrolo[3,4-c]pyrazole-1-carboxylic acid ethyl ester

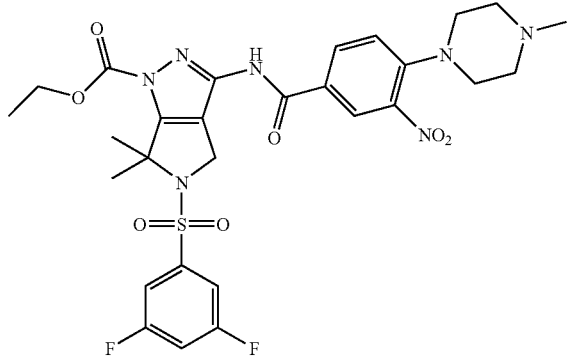 [SMILES: CCOC(=O)n1nc(NC(=O)c2ccc(N3CCN(C)CC3)c([N+](=O)[O-])c2)c2c1C(C)(C)N(S(=O)(=O)c1cc(F)cc(F)c1)C2]

1H-NMR (400 MHz), δ (ppm, DMSO-$d_6$): 10.80 (s, 1H), 8.35 (d, J=2.2 Hz, 1H), 8.01 (dd, J1=2.2 Hz, J2=8.9 Hz, 1H), 7.7-7.6 (m, 3H), 7.45 (d, J=8.9 Hz, 1H), 4.69 (bs, 2H), 4.47 (q, J=7.1 Hz, 2H), 3.19 (m, 4H), 2.47 (m, 4H), 2.26 (s, 3H), 1.68 (s, 6H), 1.37 (t, J=7.1 Hz, 3H).

Example 29

5-(3,6-Difluoro-benzenesulfonyl)-6,6-dimethyl-3-(4-morpholin-4-yl-2-nitro-benzoylamino)-5,6-dihydro-4H-pyrrolo[3,4-c]pyrazole-2-carboxylic acid ethyl ester

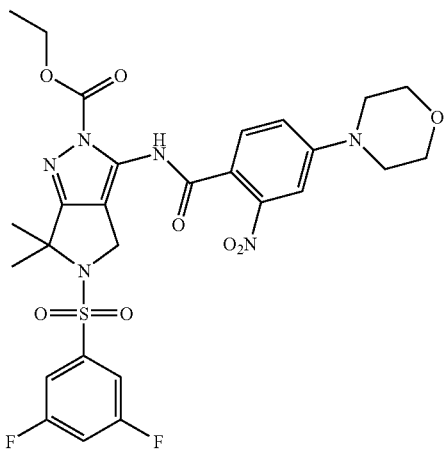 [SMILES: CCOC(=O)n1nc2c(c1NC(=O)c1ccc(N3CCOCC3)cc1[N+](=O)[O-])CN(S(=O)(=O)c1cc(F)cc(F)c1)C2(C)C]

1H-NMR (400 MHz), δ (ppm, DMSO-$d_6$): 10.71 (s, 1H), 7.66 (d, J1=8.78 Hz, 1H), 7.67-7.59 (m, 3H), 7.46 (d, J2=2.56 Hz, 1H), 7.28 (dd, J1=8.78 Hz, J2=2.56 Hz, 1H), 4.56 (s, 2H), 4.40 (q, J=7.07 Hz, 2H), 3.73 (m, 4H), 3.35 (m, 4H), 1.65 (s, 6H), 1.32 (t, J=7.07 Hz, 3H).

Example 30

5-(3,5-Difluoro-benzenesulfonyl)-3-(4-dimethylamino-2-nitro-benzoylamino)-6,6-dimethyl-5,6-dihydro-4H-pyrrolo[3,4-c]pyrazole-2-carboxylic acid ethyl ester

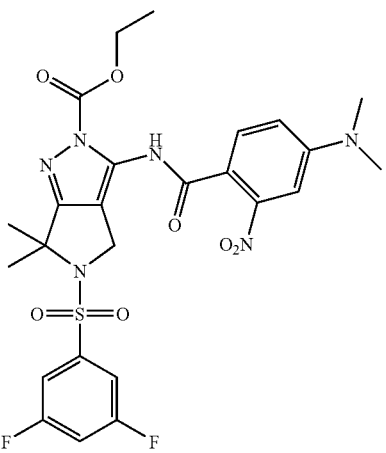

1H-NMR (400 MHz), δ (ppm, DMSO-$d_6$): 10.64 (s, 1H), 7.66-7.59 (m, 4H), 7.16 (d, J2=2.56 Hz, 1H), 6.98 (dd, J1=8.90 Hz, J2=2.56 Hz, 1H), 4.56 (s, 2H), 4.41 (q, J=7.08 Hz, 2H), 3.04 (s, 6H), 1.64 (s, 6H), 1.33 (t, J=7.08 Hz, 3H).

Example 31

5-(3,5-Difluoro-benzenesulfonyl)-3-[2-fluoro-4-(4-methyl-piperazin-1-yl)-benzoylamino]-6,6-dimethyl-5,6-dihydro-4H-pyrrolo[3,4-c]pyrazole-2-carboxylic acid ethyl ester

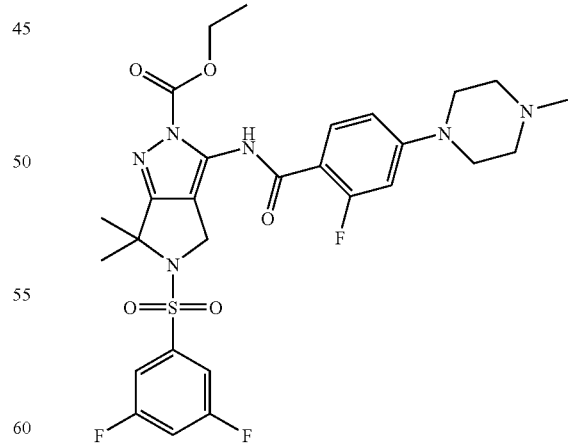

1H-NMR (400 MHz), δ (ppm, DMSO-$d_6$): 11.05, 11.02 (s, 1H), 7.87 (m, 1H), 7.69-7.62 (m, 3H), 6.96-6.86 (m, 2H), 4.76 (s, 2H), 4.47 (q, J=7.08 Hz, 2H), 3.44-3.30 (m, 4H), 2.57-2.49 (m, 4H), 2.30 (bs, 3H), 1.67 (s, 6H), 1.37 (t, J=7.08 Hz, 3H); mixture of rotamers.

Example 32

5-Benzenesulfonyl-3-[4-(4-methyl-piperazin-1-yl)-2-trifluoromethyl-benzoylamino]-5,6-dihydro-4H-pyrrolo[3,4-c]pyrazole-1-carboxylic acid ethyl ester

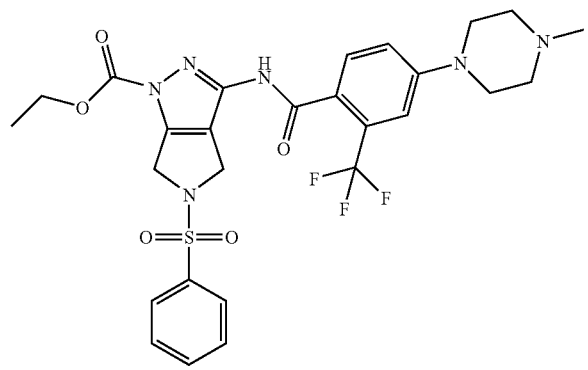 [SMILES: CCOC(=O)n1nc(NC(=O)c2ccc(N3CCN(C)CC3)cc2C(F)(F)F)c2c1CN(S(=O)(=O)c1ccccc1)C2]

1H-NMR (400 MHz), δ (ppm, DMSO-d$_6$): 11.41 (s, 1H), 7.88-7.94 (m, 2H), 7.71-7.78 (m, 1H), 7.64-7.70 (m, 2H), 7.50 (d, J=8.66 Hz, 1H) 7.15-7.25 (m, 2H), 4.65-4.72 (m, 2H), 4.47-4.52 (m, 2H), 4.38 (q, J=7.07 Hz, 2H), 3.24-3.43 (m, 4H), 2.42-2.55 (m, 4H), 2.27 (s, 3H), 133 (t, J=7.13 Hz, 3H).

Example 33

5-(3-Fluoro-benzenesulfonyl)-3-[4-(4-methyl-piperazin-1-yl)-2-trifluoromethyl-benzoylamino]-5,6-dihydro-4H-pyrrolo[3,4-c]pyrazole-1-carboxylic acid ethyl ester

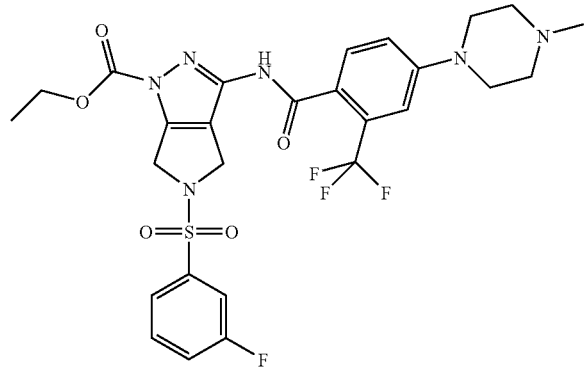 [SMILES: CCOC(=O)n1nc(NC(=O)c2ccc(N3CCN(C)CC3)cc2C(F)(F)F)c2c1CN(S(=O)(=O)c1cccc(F)c1)C2]

1H-NMR (400 MHz), δ (ppm, DMSO-d$_6$): 11.42 (s, 1H), 7.5-7.80 (m, 4H), 7.50 (d, J=8.54 Hz, 1H), 7.16-7.24 (m, 2H), 4.70-4.74 (m, 2H), 4.49-4.53 (m, 2H) 4.39 (q, J=7.03 Hz, 2H), 3.26-3.40 (m, 4H), 2.47-2.56 (m, 4H) 2.27 (s, 3H) 1.34 (t, J=7.07 Hz, 3H).

Example 34

5-(3-Fluoro-benzenesulfonyl)-3-[4-(4-methyl-piperazin-1-yl)-3-trifluoromethyl-benzoylamino]-5,6-dihydro-4H-pyrrolo[3,4-c]pyrazole-1-carboxylic acid ethyl ester

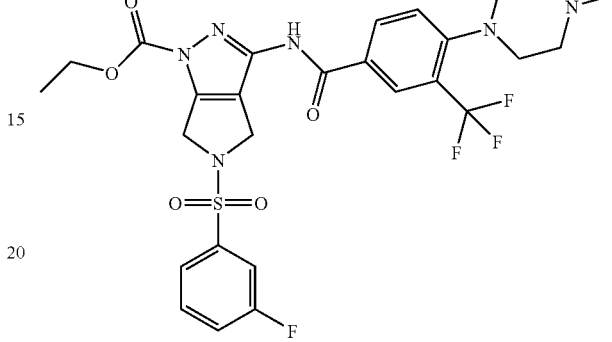

ESI(+) MS: m/z 625 (MH$^+$).

Example 35

5-(3-Fluoro-benzenesulfonyl)-3-[4-(4-methyl-piperazin-1-yl)-3-nitro-benzoylamino]-5,6-dihydro-4H-pyrrolo[3,4-c]pyrazole-1-carboxylic acid ethyl ester

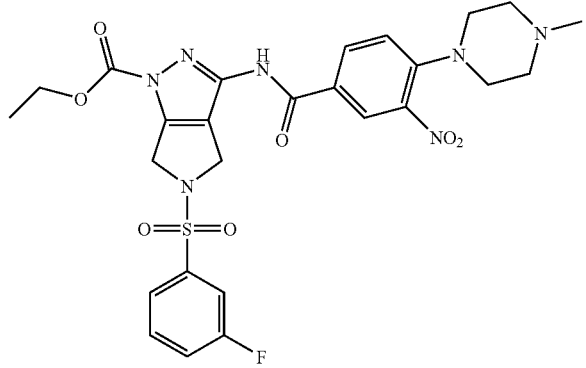

1H-NMR (400 MHz), δ (ppm, DMSO-d$_6$): 11.60 (bs, 1H), 8.54 (d, J=2.2 Hz, 1H), 8.18 (dd, J1=2.2 Hz, J2=8.9 Hz, 1H), 7.81-7.68 (m, 3H), 7.60 (m, 1H), 7.34 (d, J=8.9 Hz, 1H), 4.72 (m, 2H), 4.58 (m, 2H), 4.40 (q, J=7.0 Hz, 2H), 3.15 (m, 4H), 2.44 (m, 4H), 2.23 (s, 3H), 1.35 (t, J=7.0 Hz, 3H).

Example 36

5-(3-Fluoro-benzenesulfonyl)-3-[3-[(2-methoxy-ethyl)-methyl-amino]-4-(4-methyl-piperazin-1-yl)-benzoylamino]-5,6-dihydro-4H-pyrrolo[3,4-c]pyrazole-1-carboxylic acid ethyl ester

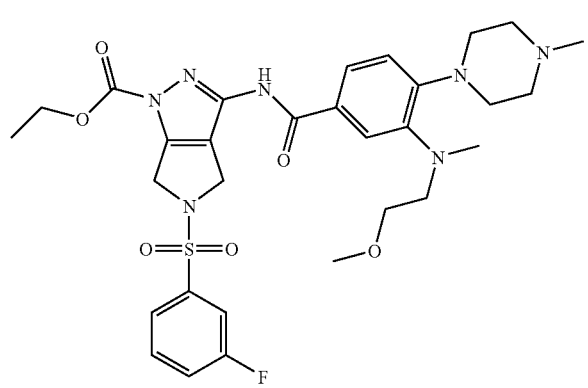 [SMILES: CCOC(=O)n1nc(NC(=O)c2ccc(N3CCN(C)CC3)c(N(C)CCOC)c2)c2c1CN(S(=O)(=O)c1cccc(F)c1)C2]

ESI(+) MS: m/z 644 (MH+).

Example 37

5-(3,6-Difluoro-benzenesulfonyl)-6,6-dimethyl-3-[4-(4-methyl-piperazin-1-yl)-benzoylamino]-5,6-dihydro-4H-pyrrolo[3,4-c]pyrazole-2-carboxylic acid ethyl ester

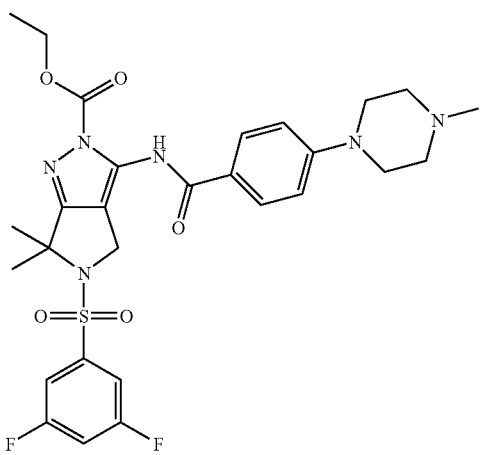 [SMILES: CCOC(=O)n1nc2c(c1NC(=O)c1ccc(N3CCN(C)CC3)cc1)CN(S(=O)(=O)c1cc(F)cc(F)c1)C2(C)C]

1H-NMR (400 MHz), δ (ppm, DMSO-$d_6$): 10.69 (s, 1H), 7.76 (m, 2H), 7.67-7.63 (m, 3H), 7.10 (m, 2H), 4.72 (s, 2H), 4.47 (q, J=7.1 Hz, 2H), 3.35 (m, 4H), 2.6-2.2 (m, 7H), 1.67 (bs, 6H), 1.37 (t, J=7.1 Hz, 3H).

Example 38

5-(3,5-Difluoro-benzenesulfonyl)-3-[3-fluoro-4-(4-methyl-piperazin-1-yl)-benzoylamino]-6,6-dimethyl-5,6-dihydro-4H-pyrrolo[3,4-c]pyrazole-1-carboxylic acid ethyl ester

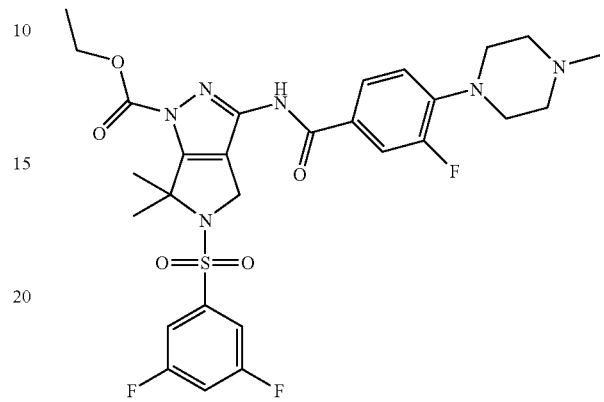

ESI(+) MS: m/z 621 (MH+).

Example 39

Preparation of 3-[2-amino-4-(4-methyl-piperazin-1-yl)-benzoylamino]-5-(3,5-difluoro-benzenesulfonyl)-6,6-dimethyl-5,6-dihydro-4H-pyrrolo[3,4-c]pyrazole-2-carboxylic acid ethyl ester dihydrochloride

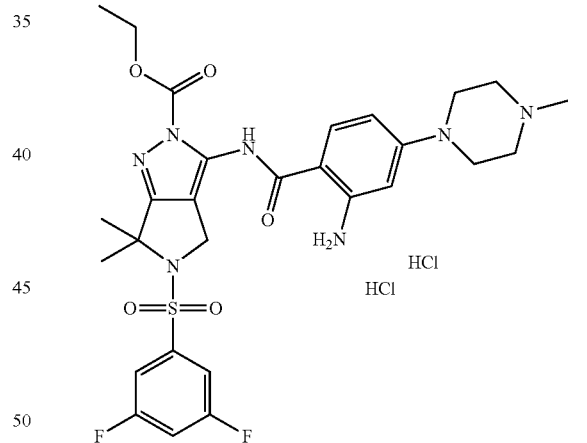

A suspension of 5-(3,5-difluoro-benzenesulfonyl)-6,6-dimethyl-3-[4-(4-methyl-piperazin-1 yl)-2-nitro-benzoylamino]-5,6-dihydro-4H-pyrrolo[3,4-c]pyrazole-2-carboxylic acid ethyl ester (1.50 g, 2.3 mmol), cyclohexene (15 eq., 20 mL), 2N HCl (13 eq., 15 mL), in tetrahydrofuran-water-ethanol (2:1.5:1.5, 50 mL) was treated with 10% Pd—C (0.55 g). The reaction mixture was stirred at 70° C. for 3 hours, and then filtered on decalite. The filtering pad was washed thoroughly with tetrahydrofuran and ethanol. The filtrate was then evaporated to dryness affording the title compound as beige powder (1.4 g, 93% yield) that was used in the next steps without any further purification.

1H-NMR (400 MHz), δ (ppm, DMSO-$d_6$): 10.60, 10.40 (bs, 1H), 7.64 (m, 3H), 7.34 (d, J1=9.02 Hz, 1H), 6.68 (bs, NH$_3^+$), 6.39 (dd, J1=9.02 Hz, J2=2.31 Hz, 1H), 6.26 (d, J2=2.31 Hz, 1H), 4.71 (s, 2H), 4.43 (q, J=7.07 Hz, 2H), 3.88 (m, 2H), 3.48 (m, 2H), 3.11 (m, 4H), 2.81, 2.80 (s, 3H), 1.63 (s, 6H), 1.34 (t, J=7.07 Hz, 3H); mixture of rotamers.

Based on Example 39, the following compounds in Examples 40-41 were also obtained:

Example 40

3-(2-Amino-4-morpholin-4-yl-benzoylamino)-5-(3,5-difluoro-benzenesulfonyl)-6,6-dimethyl-5,6-dihydro-4H-pyrrolo

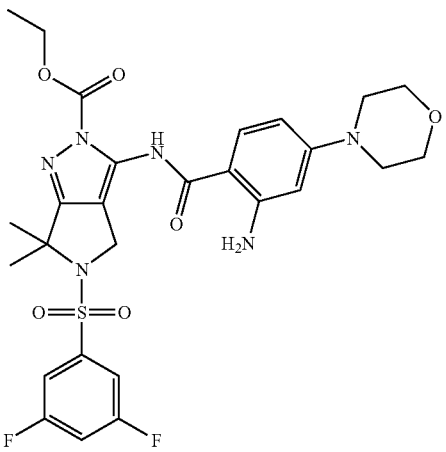

1H-NMR (400 MHz), δ (ppm, DMSO-d6): 10.54 (bs, 1H), 7.65-7.60 (m, 3H), 7.30 (d, J1=9.03 Hz, 1H), 6.34 (dd, J1=9.03 Hz, J2=2.44 Hz, 1H), 6.20 (d, J2=2.44 Hz, 1H), 4.71 (s, 2H), 4.43 (q, J=7.08 Hz, 2H), 3.70 (m, 4H), 3.17 (m, 4H), 1.63 (s, 6H), 1.34 (t, J=7.08 Hz, 3H); mixture of rotamers.

Example 41

3-(2-Amino-4-dimethylamino-benzoylamino)-5-(3,5-difluoro-benzenesulfonyl)-6,6-dimethyl-5,6-dihydro-4H-pyrrolo[3,4-c]pyrazole-2-carboxylic acid ethyl ester

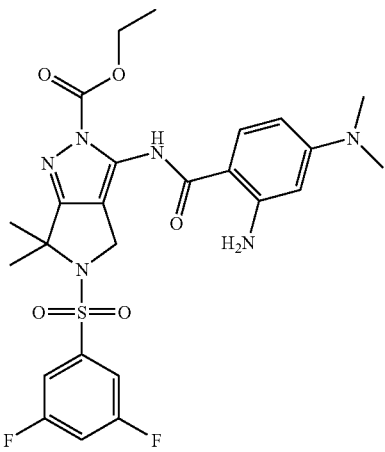 [SMILES: CCOC(=O)n1nc2c(c1NC(=O)c1ccc(N(C)C)cc1N)CN(S(=O)(=O)c1cc(F)cc(F)c1)C2(C)C]

1H-NMR (400 MHz), δ (ppm, DMSO-d6): 10.66 (bs, 1H), 7.65 (m, 2H), 7.29 (d, J1=9.03 Hz, 1H), 7.18 (m, 1H), 6.18 (dd, J1=9.03 Hz, J2=2.57 Hz, 1H), 6.01 (d, J2=2.57 Hz, 1H), 4.73 (s, 2H), 4.46 (q, J=7.08 Hz, 2H), 2.96 (s, 6H), 1.65 (s, 6H), 1.37 (t, J=7.08 Hz, 3H); mixture of rotamers.

Example 42

3-[3-Amino-4-(4-methyl-piperazin-1-yl)-benzoylamino]-5-(3-fluoro-benzenesulfonyl)-5,6-dihydro-4H-pyrrolo[3,4-c]pyrazole-1-carboxylic acid ethyl ester

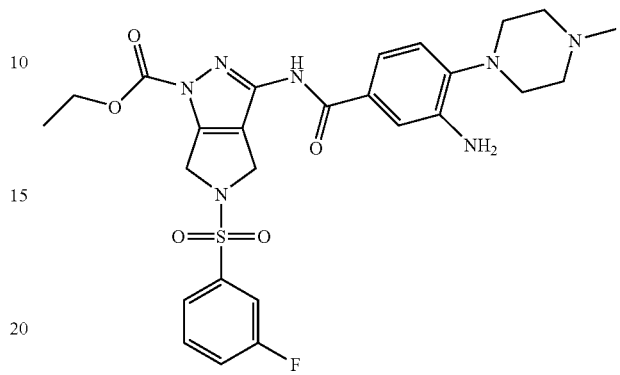

To a solution of 360 mg (1.91 mmol, 5 eq.) of SnCl2 in 3 mL of ethanol at 60° C. were added a solution of 230 mg (0.39 mmol) of 5-(3-fluoro-benzenesulfonyl)-3-[4-(4-methyl-piperazin-1-yl)-3-nitro-benzoylamino]-5,6-dihydro-4H-pyrrolo[3,4-c]pyrazole-1-carboxylic acid ethyl ester in 2 mL of ethanol and 2 mL of concentrated hydrochloric acid. After 2 hours, the solvent was removed under reduced pressure, the residue was treated with saturated sodium hydrogencarbonate solution, extracted with ethyl acetate, and the organic phase dried over anhydrous sodium sulfate. The solvent was evaporated and the residue was purified by flash column chromatography, using dichloromethane-methanol 9:1 as eluant, to give 120 mg (54% yield) of 3-[3-amino-4-(4-methyl-piperazin-1-yl)-benzoylamino]-5-(3-fluoro-benzenesulfonyl)-5,6-dihydro-4H-pyrrolo[3,4-c]pyrazole-1-carboxylic acid ethyl ester as white solid.

ESI(+) MS: m/z 572 (MH+).

Example 43

Preparation of N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide

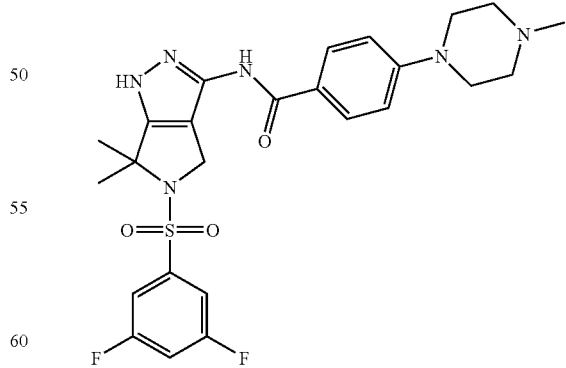

A mixture of 5-(3,5-difluoro-benzenesulfonyl)-6,6-dimethyl-3-[4-(4-methyl-piperazin-1-yl)-benzoylamino]-5,6-dihydro-4H-pyrrolo[3,4-c]pyrazole-2-carboxylic acid ethyl ester (1.6 g, 3 mmol) in MeOH (60 mL) and triethylamine (5 mL) was heated at 60° C. for 2 hours. The reaction mixture was then evaporated to dryness and the crude residue crystallized from ethyl acetate, filtered, washed with diethyl ether and dried under vacuum affording the title compound as white solid (1.2 g).

1H-NMR (400 MHz), δ (ppm, DMSO-d$_6$): 12.44, 12.11 (two bs, 1H), 10.62 (bs, 1H), 7.90 (m, 2H), 7.69-7.56 (m, 3H), 6.99 (m, 2H), 4.65-450 (m, 2H), 3.31 (m, 4H), 2.49 (m, 4H), 2.26 (bs, 3H), 1.67 (bs, 6H); mixture of tautomers.

Based on Example 43, starting from the suitable precursor the following compounds in Examples 44-56 were obtained:

Example 44

N-[5-(3-Fluoro-benzenesulfonyl)-1,4,5,6-tetrahydro-pyrrolo[3,4-c]pyrazol-3-yl]-4-(4-methyl-piperazin-1-yl)-2-nitro-benzamide

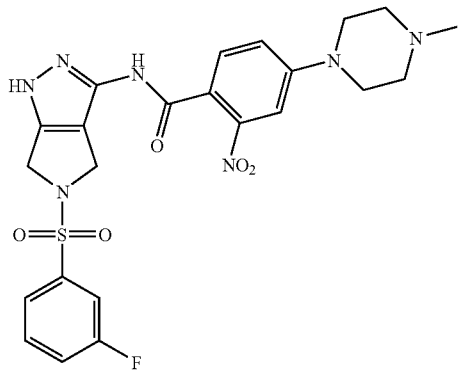 [SMILES: CN1CCN(c2ccc(C(=O)Nc3n[nH]c4c3CN(S(=O)(=O)c3cccc(F)c3)C4)c([N+](=O)[O-])c2)CC1]

1H-NMR (400 MHz), δ (ppm, DMSO-d$_6$): 12.39 (bs, 1H), 11.02 (bs, 1H), 7.73 (m, 3H), 7.59 (m, 2H), 7.41 (m, 1H), 7.22 (m, 1H), 4.52-4.40 (m, 4H), 3.33 (m, 4H), 2.45 (m, 4H), 2.24 (s, 3H); mixture of tautomers.

Example 45

N-[5-(3,5-Difluoro-benzenesulfonyl)-6,6-dimethyl-1,4,5,6-tetrahydro-pyrrolo[3,4-c]pyrazol-3-yl]-4-(4-methyl-piperazin-1-yl)-2-nitro-benzamide

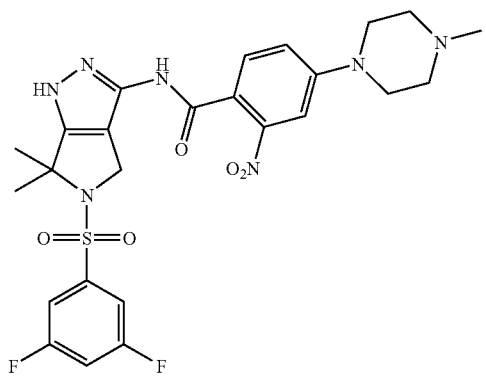 [SMILES: CN1CCN(c2ccc(C(=O)Nc3n[nH]c4c3CN(S(=O)(=O)c3cc(F)cc(F)c3)C4(C)C)c([N+](=O)[O-])c2)CC1]

1H-NMR (400 MHz), δ (ppm, DMSO-d$_6$): 12.51, 12.39 (bs, 1H), 11.15, 11.07 (bs, 1H), 7.68-7.57 (m, 4H), 7.42 (m, bs, 1H), 7.23 (m, bs, 1H), 4.60-4.41 (bs, 2H), 3.42-3.27 (m, 4H), 2.45 (m, 4H), 2.24 (s, 3H), 1.68 (bs, 6H); mixture of tautomers.

Example 46

N-[5-(3,5-Difluoro-benzenesulfonyl)-6,6-dimethyl-1,4,5,6-tetrahydro-pyrrolo[3,4-c]pyrazol-3-yl]-4-(4-methyl-piperazin-1-yl)-3-nitro-benzamide

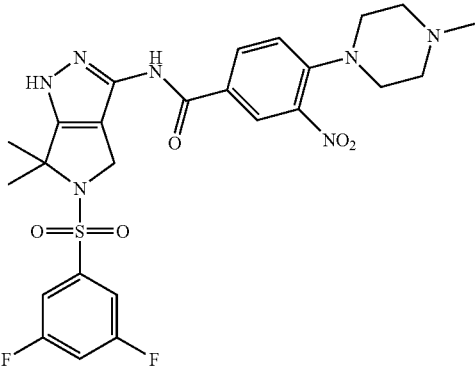 [SMILES: CN1CCN(c2ccc(C(=O)Nc3n[nH]c4c3CN(S(=O)(=O)c3cc(F)cc(F)c3)C4(C)C)cc2[N+](=O)[O-])CC1]

1H-NMR (400 MHz), δ (ppm, DMSO-d$_6$): 12.55, 12.28 (2 bs, 1H), 11.06, 11.00 (2 bs, 1H), 8.52-8.40 (m, 1H), 8.20-8.05 (m, 1H), 7.70-7.58 (m, 3H), 7.44-7.31 (m, 1H), 4.65-4.50 (m, 2H), 3.15 (m, 4H), 2.47 (m, 4H), 2.26 (bs, 3H), 1.68 (bs, 6H), mixture of tautomers.

Example 47

2-Amino-N-[5-(3,5-difluoro-benzenesulfonyl)-6,6-dimethyl-1,4,5,6-tetrahydro-pyrrolo[3,4-c]pyrazol-3-yl]-4-morpholin-4-yl-benzamide

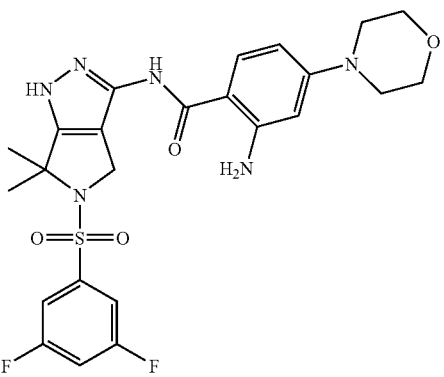 [SMILES: CC1(C)c2[nH]nc(NC(=O)c3ccc(N4CCOCC4)cc3N)c2CN1S(=O)(=O)c1cc(F)cc(F)c1]

1H-NMR (400 MHz), δ (ppm, DMSO-d$_6$): 12.35, 11.96 (bs, 1H), 10.24 (s, 1H), 7.65-7.55 (m, 4H), 6.54 (bs, 2H), 6.22 (m, bs, 1H), 6.16 (d, J=1.83 Hz, 1H), 4.53 (bs, 2H), 3.70 (m, 4H), 3.13 (m, 4H), 1.62 (s, 6H); mixture of tautomers.

Example 48

2-Amino-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide

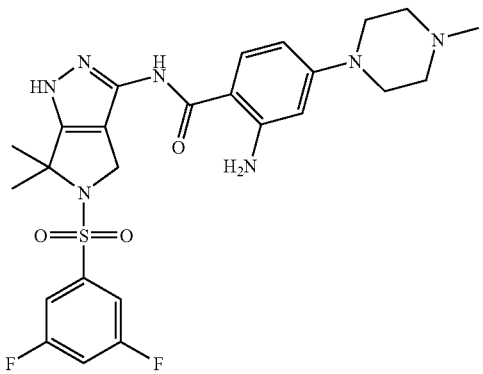

1H-NMR (400 MHz), δ (ppm, DMSO-$d_6$): 12.37, 11.99 (bs, 1H), 10.25 (bs, 1H), 7.67-7.59 (m, 4H), 6.55 (bs, 2H), 6.30-6.15 (m, bs, 2H), 4.56 (bs, 2H), 3.20 (m, bs, 4H), 2.43 (m, 4H), 2.23 (s, 3H), 1.65 (bs, 6H); mixture of tautomers.

Example 49

N-[5-(3,5-Difluoro-benzenesulfonyl)-6,6-dimethyl-1,4,5,6-tetrahydro-pyrrolo[3,4-c]pyrazol-3-yl]-2-fluoro-4-(4-methyl-piperazin-1-yl)-benzamide

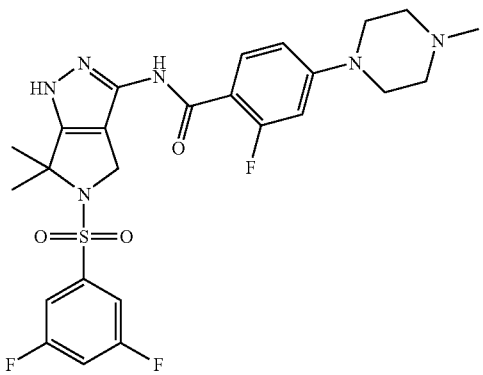 [SMILES: CN1CCN(c2ccc(C(=O)Nc3n[nH]c4c3CN(S(=O)(=O)c3cc(F)cc(F)c3)C4(C)C)c(F)c2)CC1]

1H-NMR (400 MHz), δ (ppm, DMSO-$d_6$): 12.47, 12.18 (bs, 1H) 10.27, 10.19 (bs, 1H), 7.68-7.58 (m, 4H), 6.90-6.75 (m, bs, 2H), 4.60, 4.55 (bs, 2H), 3.34 (m, 4H), 2.47 (m, bs, 4H), 2.26 (bs, 3H), 1.67, 1.64 (bs, 6H); mixture of tautomers.

Example 50

N-[5-(3,5-Difluoro-benzenesulfonyl)-6,6-dimethyl-1,4,5,6-tetrahydro-pyrrolo[3,4-c]pyrazol-3-yl]-3-fluoro-4-(4-methyl-piperazin-1-yl)-benzamide

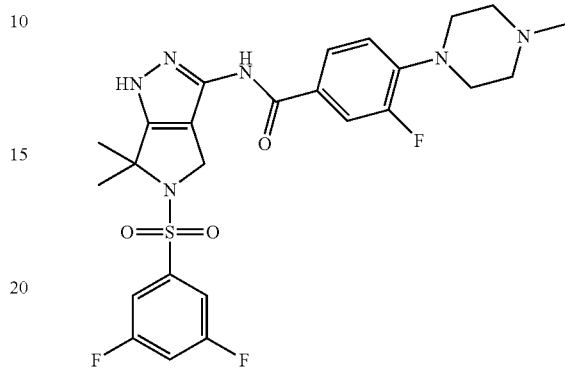

1H-NMR (400 MHz), δ (ppm, DMSO-$d_6$): 12.51, 12.24 (2 bs, 1H), 10.84 (s, 1H), 7.80 (m, 2H), 7.69-7.58 (m, 3H), 7.11 (m, 1H), 4.63-4.50 (m, 2H), 3.17 (m, 4H), 2.54 (m, 4H), 2.29 (bs, 3H), 1.67 (bs, 6H), mixture of tautomers.

Example 51

N-(5-Benzenesulfonyl-1,4,5,6-tetrahydro-pyrrolo[3,4-c]pyrazol-3-yl)-4-(4-methyl-piperazin-1-yl)-2-trifluoromethyl-benzamide

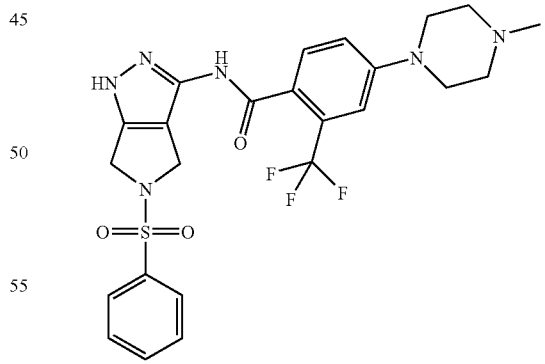

1H-NMR (400 MHz), δ (ppm, DMSO-$d_6$): 12.28 (s, 1H), 10.80 (s, 1H), 7.87-7.90 (m, 2H), 7.69-7.77 (m, 1H), 7.61-7.68 (m, 2H), 7.40-7.53 (m, 1H), 7.16-7.32 (m, 2H), 4.32-4.56 (m, 4H), 3.19-3.43 (m, 4H) 2.42-2.60 (m, 4H) 2.27 (s, 3H).

Example 52

N-[5-(3-Fluoro-benzenesulfonyl)-1,4,5,6-tetrahydro-pyrrolo[3,4-c]pyrazol-3-yl]-4-(4-methyl-piperazin-1-yl)-2-trifluoromethyl-benzamide

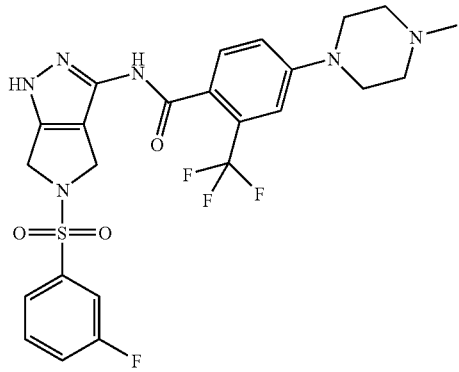 [SMILES: CN1CCN(c2ccc(C(=O)Nc3n[nH]c4c3CN(S(=O)(=O)c3cccc(F)c3)C4)c(C(F)(F)F)c2)CC1]

1H-NMR (400 MHz), δ (ppm, DMSO-$d_6$): 12.37 (bs, 1H), 11.03, 10.84 (bs, 1H), 7.76-7.13 (m, 7H), 4.54, 4.43 (m, bs, 4H), 3.41-3.26 (m, 4H), 2.65 (m, bs, 4H), 2.39 (bs, 3H); mixture of tautomers.

Example 54

N-[5-(3-Fluoro-benzenesulfonyl)-1,4,5,6-tetrahydro-pyrrolo[3,4-c]pyrazol-3-yl]-4-(4-methyl-piperazin-1-yl)-3-nitro-benzamide

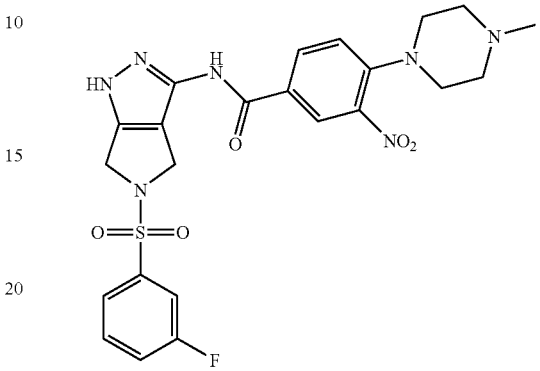

1H-NMR (400 MHz), δ (ppm, DMSO-$d_6$): 12.45, 12.26 (2 bs, 1H), 11.00 (bs, 1H), 8.52-8.37 (m, 1H), 8.20-8.00 (m, 1H), 7.80-7.67 (m, 3H), 7.59 (m, 1H), 7.45-7.28 (m, 1H), 4.61-4.38 (m, 4H), 3.15 (m, 4H), 2.46 (m, 4H), 2.25 (bs, 3H), mixture of tautomers.

Example 53

N-[5-(3-Fluoro-benzenesulfonyl)-1,4,5,6-tetrahydro-pyrrolo[3,4-c]pyrazol-3-yl]-4-(4-methyl-piperazin-1-yl)-3-trifluoromethyl-benzamide

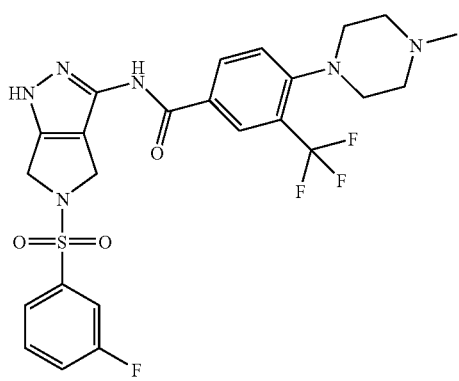 [SMILES: CN1CCN(c2ccc(C(=O)Nc3n[nH]c4c3CN(S(=O)(=O)c3cccc(F)c3)C4)cc2C(F)(F)F)CC1]

1H-NMR (400 MHz), δ (ppm, DMSO-$d_6$): 12.47, 12.30 (2 bs, 1H), 11.10 (bs, 1H), 8.84-8.17 (m, 2H), 7.81-7.67 (m, 3H), 7.63-7.52 (m, 2H), 4.62-4.37 (m, 4H), 2.99 (m, 4H), 2.51 (m, 4H), 2.27 (bs, 3H), mixture of tautomers.

Example 55

2-Amino-N-[5-(3-fluoro-benzenesulfonyl)-1,4,5,6-tetrahydro-pyrrolo[3,4-c]pyrazol-3-yl]-4-(4-methyl-piperazin-1-yl)-benzamide

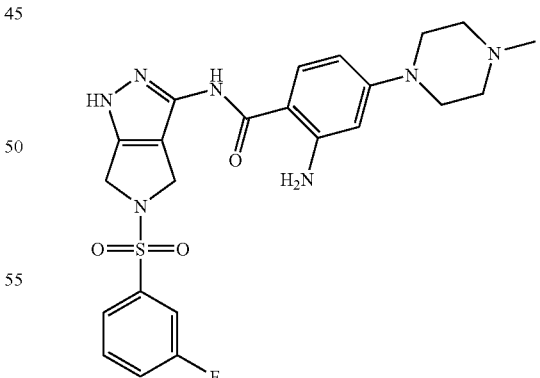

1H-NMR (400 MHz), δ (ppm, DMSO-$d_6$): 12.27, 11.95 (bs, 1H), 10.21 (bs 1H), 7.77-7.51 (m, 5H), 6.66, 6.55 (bs, 2H), 6.26-6.17 (m, bs, 2H), 4.55-4.41 (m, bs, 4H), 3.21 (m, bs, 4H), 2.47 (m, bs, 4H), 2.26 (s, 3H); mixture of tautomers.

Example 56

3-Amino-N-[5-(3-fluoro-benzenesulfonyl)-1,4,5,6-tetrahydro-pyrrolo[3,4-c]pyrazol-3-yl]-4-(4-methyl-piperazin-1-yl)-benzamide

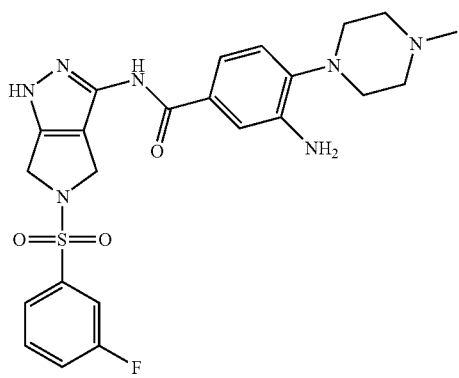 [SMILES: CN1CCN(c2ccc(C(=O)Nc3n[nH]c4c3CN(S(=O)(=O)c3cccc(F)c3)C4)cc2[N+](=O)[O-])CC1]

1H-NMR (400 MHz), δ (ppm, DMSO-$d_6$): 12.35, 12.12 (2 bs, 1H), 10.65, 10.54 (2 bs, 1H), 7.78-7.67 (m, 3H), 7.59 (m, 1H), 7.31-7.12 (m, 2H), 7.0-6.88 (m, 1H), 4.84 (m, 2H), 4.6-4.3 (m, 4H), 2.88 (m, 4H), 2.53 (m, 4H), 2.27 (bs, 3H), mixture of tautomers.

Example 57

Preparation of N-[5-(3-fluoro-benzenesulfonyl)-1,4,5,6-tetrahydro-pyrrolo[3,4-c]pyrazol-3-yl]-3-[(2-hydroxyethyl)-methyl-amino]-4-(4-methyl-piperazin-1-yl)-benzamide

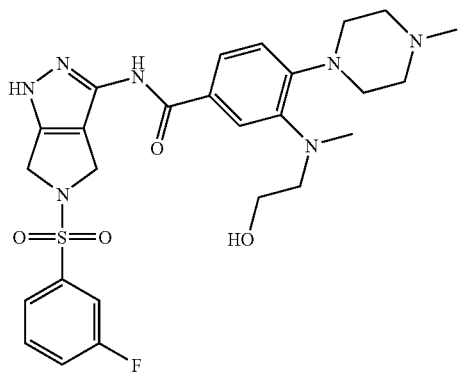 [SMILES: CN1CCN(c2ccc(C(=O)Nc3n[nH]c4c3CN(S(=O)(=O)c3cccc(F)c3)C4)cc2N(C)CCO)CC1]

A solution of 5-(3-fluoro-benzenesulfonyl)-3-[3-[(2-methoxy-ethyl)-methyl-amino]-4-(4-methyl-piperazin-1-yl)-benzoylamino]-5,6-dihydro-4H-pyrrolo[3,4-c]pyrazole-1-carboxylic acid ethyl ester (120 mg, 0.186 mmol) in 5 mL of 1M BBr$_3$ in dichloromethane was stirred at room temperature for 24 h. The mixture was washed with saturated aqueous NaHCO$_3$ and the combined organic layers were evaporated to dryness. The resulting crude (110 mg) was then dissolved in 4 mL of MeOH and 0.5 mL of triethylamine and the mixture was stirred at room temperature for 3 h. The solvent was removed and the final product was purified by flash column chromatography, using dichloromethane-methanol-aqueous ammonia 9:1:0.5 as eluant, affording 70 mg of yellow solid.

1H-NMR (400 MHz), δ (ppm, DMSO-$d_6$): 12.39, 12.14 (2 bs, 1H), 10.71 (bs, 1H), 7.80-7.67 (m, 3H), 7.63-7.48 (m, 3H), 6.93 (m, 1H), 4.6-4.4 (m, 5H), 3.50 (m, 2H), 3.28 (m, 2H), 3.18 (m, 4H), 2.83 (s, 3H), 2.59 (m, 4H), 2.30 (bs, 3H), mixture of tautomers.

Example 58

Preparation of 2-(cyclobutanecarbonyl-amino)-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide

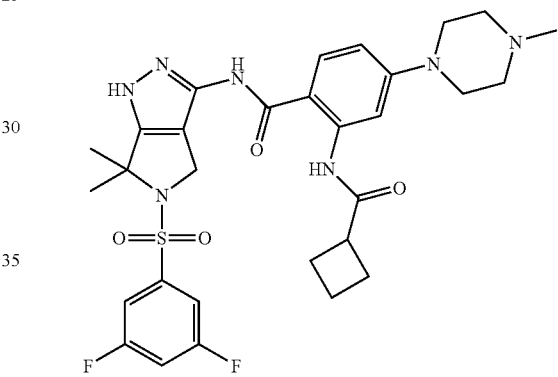

To a solution of 3-[2-amino-4-(4-methyl-piperazin-1-yl)-benzoylamino]-5-(3,5-difluoro-benzenesulfonyl)-6,6-dimethyl-5,6-dihydro-4H-pyrrolo[3,4-c]pyrazole-2-carboxylic acid ethyl ester (105 mg, 0.17 mmol) in dichloromethane (5 mL) and N,N-diisopropylethylamine (1 mL), cyclobutanecarbonyl chloride (28.5 microL, 0.25 mmol) was added and the reaction mixture stirred at room temperature for 2 hours. The mixture was then diluted with dichloromethane (30 mL), washed with water (30 mL), dried over sodium sulphate and evaporated to dryness. The crude oil was then treated with MeOH (5 mL) and triethylamine (3 mL) and stirred at room temperature for 2 hours. The solvent was removed under vacuum and the residue purified by flash chromatography on silica gel, using a mixture dichloromethane-MeOH-30% NH$_4$OH 100:10:1 as the eluant, affording the title compound as white solid (21 mg).

1H-NMR (400 MHz), δ (ppm, DMSO-$d_6$): 12.53, 12.16 (bs, 1H), 11.62, 11.37 (bs, 1H), 10.79 (s, 1H), 8.17 (d, J2=2.44 Hz, 1H), 7.88, 7.75 (m, bs, 1H), 7.67 (m, 1H), 7.58 (m, 2H), 6.75, 6.67 (m, bs, 1H), 4.57, 4.52 (bs, 2H), 3.36-3.21 (m, 5H), 2.48 (m, 4H), 2.26 (s, 3H), 2.24-2.15 (m, 2H), 2.03-1.96 (m, 2H), 1.87-1.78 (m, 2H), 1.70, 1.66 (bs, 6H); mixture of tautomers.

Based on Example 58, and using the suitable acid chloride, the following compounds in Examples 59-61 were obtained.

Example 59

N-[5-(3,5-Difluoro-benzenesulfonyl)-6,6-dimethyl-1,4,5,6-tetrahydro-pyrrolo[3,4-c]pyrazol-3-yl]-2-isobutyrylamino-4-(4-methyl-piperazin-1-yl)-benzamide

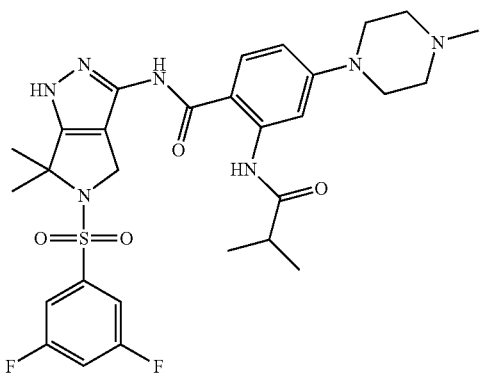 [SMILES: CC(C)C(=O)Nc1cc(N2CCN(C)CC2)ccc1C(=O)Nc1n[nH]c2c1CN(S(=O)(=O)c1cc(F)cc(F)c1)C2(C)C]

1H-NMR (400 MHz), δ (ppm, DMSO-$d_6$): 12.53, 12.19 (bs, 1H) 11.69, 11.47 (bs, 1H), 10.79 (s, 1H), 8.15 (d, J2=2.44 Hz, 1H), 7.87, 7.76 (m, bs, 1H), 7.67 (m, 1H), 7.58 (m, 2H), 6.76, 6.68 (m, bs, 1H), 4.57, 4.52 (bs, 2H), 3.42-3.25 (m, 5H), 2.47 (m, 4H), 2.25 (s, 3H), 1.70, 1.66 (bs, 6H), 1.18 (d, 6.95 Hz, 6H); mixture of tautomers.

Example 60

N-[5-(3,5-Difluoro-benzenesulfonyl)-6,6-dimethyl-1,4,5,6-tetrahydro-pyrrolo[3,4-c]pyrazol-3-yl]-2-(2-dimethylamino-acetylamino)-4-(4-methyl-piperazin-1-yl)benzamide

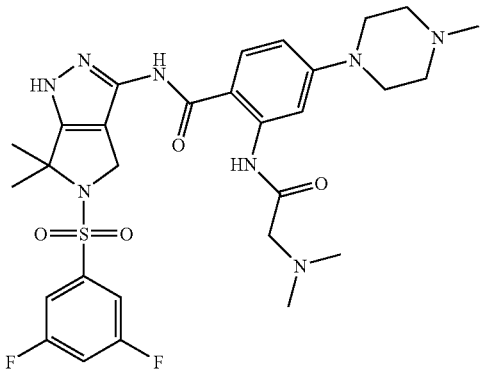 [SMILES: CN(C)CC(=O)Nc1cc(N2CCN(C)CC2)ccc1C(=O)Nc1n[nH]c2c1CN(S(=O)(=O)c1cc(F)cc(F)c1)C2(C)C]

1H-NMR (400 MHz), δ (ppm, DMSO-$d_6$): 12.21, 12.08 (bs, 1H), 10.76 (s, 1H), 8.26 (d, J2=2.56 Hz, 1H), 7.92, 7.85 (m, bs, 1H), 7.68 (m, 1H), 7.55 (m, 2H), 6.76, 6.68 (m, bs, 1H), 4.64, 4.57 (bs, 2H), 3.29 (m, 4H), 3.06 (s, 2H), 2.45 (m, 4H), 2.30 (s, 6H), 2.23 (s, 3H), 1.70 (bs, 6H), mixture of tautomers.

Example 61

N-[5-(3-Fluoro-benzenesulfonyl)-1,4,5,6-tetrahydro-pyrrolo[3,4-c]pyrazol-3-yl]-3-(2-methoxy-acetylamino)-4-(4-methyl-piperazin-1-yl)-benzamide

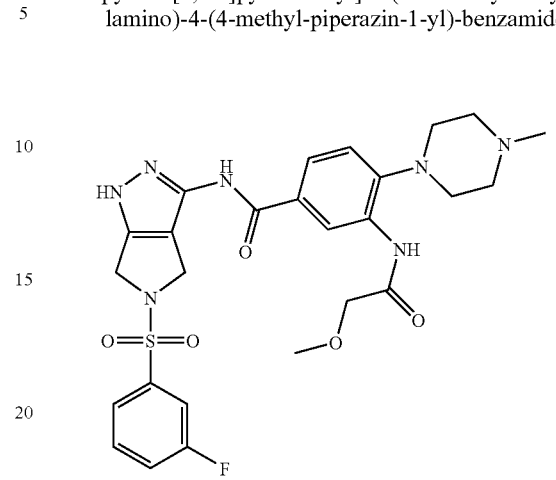

1H-NMR (400 MHz), δ (ppm, DMSO-$d_6$): 12.41, 12.19, 10.85, 9.27, 8.77 (5 bs, 3H), 7.8-7.1 (m, 7H), 4.6-4.4 (m, 4H), 4.08 (s, 2H), 3.50 (s, 3H), 3.7-2.3 (m, 8H), 2.94 (bs, 3H), mixture of tautomers.

Example 62

Preparation of 5-(3,6-difluoro-benzenesulfonyl)-3-(2-{[(S)-1-(9H-fluoren-9-ylmethoxycarbonyl)-pyrrolidine-2-carbonyl]-amino}-4-morpholin-4-yl-benzoylamino)-6,6-dimethyl-5,6-dihydro-4H-pyrrolo[3,4-c]pyrazole-2-carboxylic acid ethyl ester

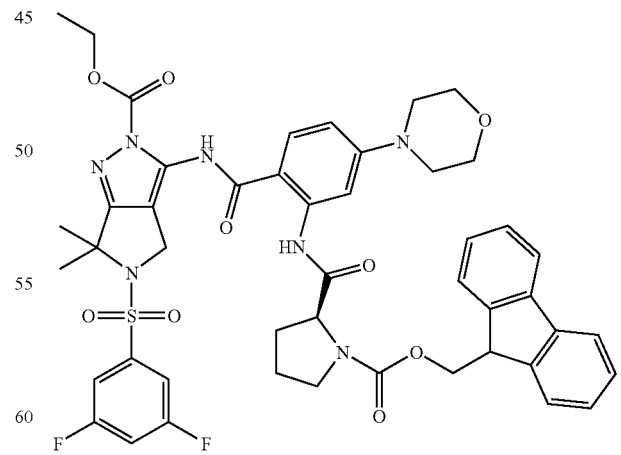

To a solution of ethyl 3-(2-amino-4-morpholin-4-yl-benzoylamino)-5-(3,5-difluoro-benzenesulfonyl)-6,6-dimethyl- 5,6-dihydro-4H-pyrrolo[3,4-c]pyrazole-2-carboxylic acid ethyl ester (0.3 g, 0.5 mmol) and N,N-diisopropylethylamine (260 microL) in dichloromethane (15 mL), (S)-2-chlorocarbonyl-1-(9H-fluoren-9-ylmethoxycarbonyl)-pyrrolidine (0.266 g, 0.75 mmol, 1.5 eq.) was added and the reaction mixture stirred at room temperature for 12 hours. After removal of the solvent under vacuum, the crude residue was purified by flash chromatography on silica gel, using a mixture hexane-ethyl acetate 1:1 as the eluant, giving the title compound as yellow powder (0.33 g).

1H-NMR (400 MHz), δ (ppm, DMSO-$d_6$): 11.95, 11.75 (2 bs, 1H), 10.76, 10.66 (2 bs, 1H), 8.26, 8.15 (2 bs, 1H), 7.86 (m, 2H), 7.72-7.53 (m, 5H), 7.89 (m, 2H), 7.25 (m, 2H), 6.99-6.88 (m, 2H), 4.72 (m, 2H), 4.46 (q, 2H), 4.42-4.1 (m, 2H), 3.78 (m, 4H), 3.70-3.57 (m, 2H), 3.33 (m, 4H), 2.39-2.29 (m, 2H), 2.13-1.79 (m, 2H), 1.67, 1.64 (s, 3H), 1.57, 1.53 (s, 3H), 1.37 (t, J=7.19 Hz, 3H); mixture of rotamers.

Based on Example 62, and using the suitable acid chloride, the following compounds in Examples 63-64 were obtained:

Example 63

5-(3,5-Difluoro-benzenesulfonyl)-3-(4-dimethylamino-2-{2-[(9H-fluoren-9-ylmethoxycarbonyl)-methyl-amino]-acetylamino}-benzoylamino)-6,6-dimethyl-5,6-dihydro-4H-pyrrolo[3,4-c]pyrazole-2-carboxylic acid ethyl ester

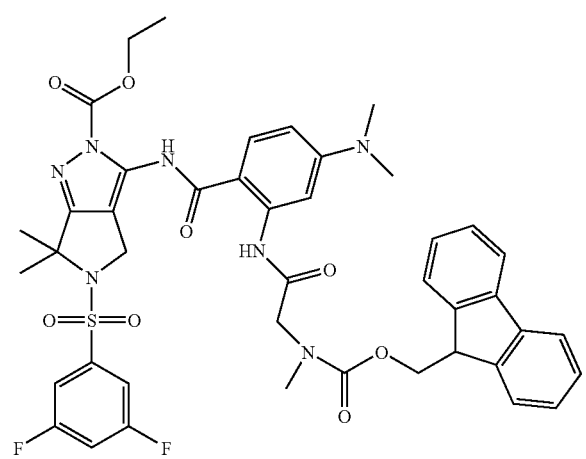 [SMILES: CCOC(=O)n1nc2c(c1NC(=O)c1ccc(N(C)C)cc1NC(=O)CN(C)C(=O)OCC1c3ccccc3-c3ccccc31)CN(S(=O)(=O)c1cc(F)cc(F)c1)C2(C)C]

1H-NMR (400 MHz), δ (ppm, DMSO-$d_6$): 11.92, 11.60 (s, 1H), 10.67, 10.64 (s, 1H), 8.1-7.8 (m, 3H), 7.75-7.30 (m, 6H), 7.22 (m, 2H), 6.95 (m, 2H), 6.62 (m, 1H), 4.73, 4.71 (s, 2H), 4.44 (q, J=7.20 Hz, 2H), 4.28 (d, J=6.95 Hz, 2H), 4.16 (t, J=6.95 Hz, 1H), 4.05 (s, 2H), 3.12, 3.08 (s, 3H), 3.05, 3.02 (s, 6H), 1.56, 1.55 (bs, 6H), 1.35 (t, J=7.20 Hz, 3H); mixture of rotamers.

Example 64

5-(3,5-Difluoro-benzenesulfonyl)-3-{2-(2-[(9H-fluoren-9-ylmethoxycarbonyl)-methyl-amino]-acetylamino}-4-morpholinyl-benzoylamino)-6,6-dimethyl-5,6-dihydro-4H-pyrrolo[3,4-c]pyrazole-2-carboxylic acid ethyl ester

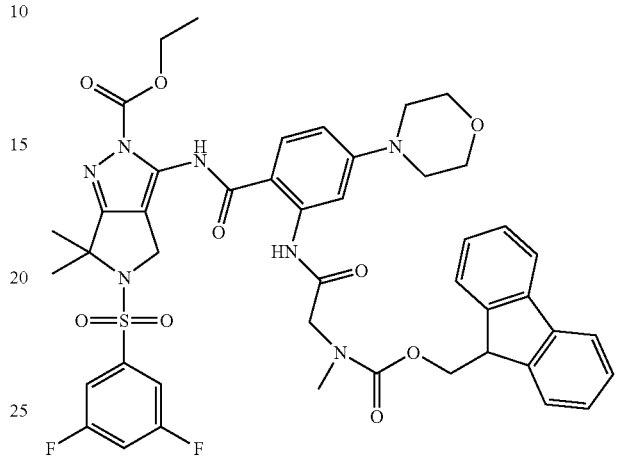

Example 65

Preparation of (S)-pyrrolidine-2-carboxylic acid {2-[5-(3,5-difluoro-benzenesulfonyl)-6,6-dimethyl-1,4,5,6-tetrahydro-pyrrolo[3,4-c]pyrazol-3-ylcarbamoyl]-5-morpholin-4-yl-phenyl}-amide

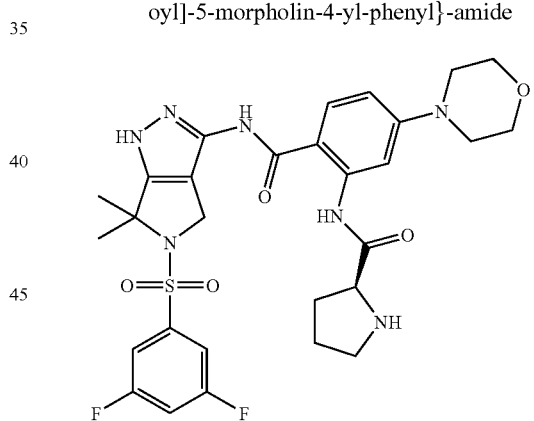

To a solution of ethyl 5-(3,5-difluoro-benzenesulfonyl)-3-(2-{[(S)-1-(9H-fluoren-9-ylmethoxycarbonyl)-pyrrolidine-2-carbonyl]-amino}-4-morpholin-4-yl-benzoylamino)-6,6-dimethyl-5,6-dihydro-4H-pyrrolo[3,4-c]pyrazole-2-carboxylic acid ethyl ester (0.3 g, 0.32 mmol) in MeOH (10 mL) and dichloromethane (3 mL), piperidine (1 mL) was added and the reaction mixture stirred at room temperature for 12 hours. After evaporation to dryness, the residue was washed with petroleum ether and purified by flash chromatography on silica gel, using a mixture dichloromethane-MeOH 95:5 as the eluant, affording the title compound as pale yellow powder (0.15 g).

1H-NMR (400 MHz), δ (ppm, DMSO-$d_6$): 12.49-12.19 (bs, 2H), 10.74 (bs, 1H), 8.27 (d, J2=2.56 Hz, 1H), 7.76 (m, bs, 1H), 7.67 (m, 1H), 7.58 (m, 2H), 6.70 (m, bs, 1H), 4.66-4.53 (m, bs, 2H), 3.74 (m, 5H), 3.23 (m, 4H), 3.01-2.84 (m, 2H), 2.11-1.61 (m, 10H); mixture of tautomers.

Based on Example 65, starting from the suitable precursor, the following compound in Example 66 was obtained:

Example 66

N-[5-(3,5-Difluoro-benzenesulfonyl)-6,6-dimethyl-2,4,5,6-tetrahydro-pyrrolo[3,4-c]pyrazol-3-yl]-2-(2-methylamino-acetylamino)-4-morpholin-4-yl-benzamide

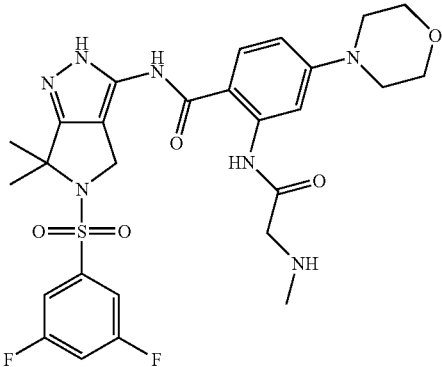 [SMILES: CNCC(=O)Nc1cc(N2CCOCC2)ccc1C(=O)Nc1[nH]nc2c1CN(S(=O)(=O)c1cc(F)cc(F)c1)C2(C)C]

1H-NMR (400 MHz), δ (ppm, DMSO-$d_6$): 12.50, 12.17 (bs, 1H), 10.54 (bs, 1H), 8.28 (d, J2=2.56 Hz, 1H), 7.82-7.72 (m, bs, 1H), 7.66 (m, 1H), 7.58 (m, 2H), 6.79-6.67 (m, bs, 1H), 4.62, 4.56 (s, 2H), 4.75 (m, 4H), 3.23 (m, 6H), 2.35 (s, 3H), 1.69 (s, 6H); mixture of tautomers.

Example 67

Preparation of 2-((S)-2-amino-propionylamino)-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide

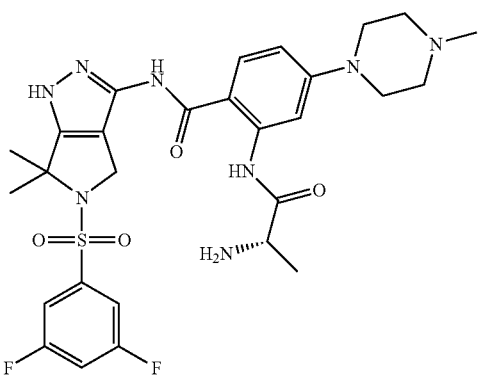 [SMILES: C[C@H](N)C(=O)Nc1cc(N2CCN(C)CC2)ccc1C(=O)Nc1n[nH]c2c1CN(S(=O)(=O)c1cc(F)cc(F)c1)C2(C)C]

To a solution of 2-amino-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide (0.188 g, 0.34 mmol), N,N-diisopropylethylamine (0.59 mL, 3.4 mmol) and dichloromethane (10 mL), (S)-2-[(9H-fluoren-9-ylmethoxycarbonyl)amino]-propionyl chloride (0.448 g, 1.36 mmol, 4 eq.) was added and the reaction mixture stirred at room temperature overnight. After evaporation to dryness, the residue was treated with dichloromethane (10 mL), triethylamine (5 mL) and MeOH (5 mL) and the mixture stirred at room temperature for 72 hours. The solvent was then removed under vacuum and the residue purified by preparative HPLC/MS affording the title compound as white solid (0.105 g).

1H-NMR (400 MHz), δ (ppm, DMSO-$d_6$): 12.47 (bs, 1H), 12.25 (bs, 1H), 10.77 (bs, 1H), 8.26 (d, J2=1.83 Hz, 1H), 7.73 (m, bs, 1H), 7.65 (m, 1H), 7.59 (m, 2H), 6.67 (bs, 1H), 4.58 (bs, 2H), 3.41 (m, 1H), 3.27 (m, 4H), 3.18 (d, J=5.25 Hz, 2H), 2.45 (m, 4H), 2.23 (s, 3H), 1.67 (s, 6H), 1.26 (d, J=7.07 Hz, 3H); mixture of tautomers.

Based on Example 67, the following compounds in Examples 68-69 were obtained:

Example 68

N-[5-(3,5-Difluoro-benzenesulfonyl)-6,6-dimethyl-1,4,5,6-tetrahydro-pyrrolo[3,4-c]pyrazol-3-yl]-2-(2-methylamino-acetylamino)-4-(4-methyl-piperazin-1-yl)-benzamide

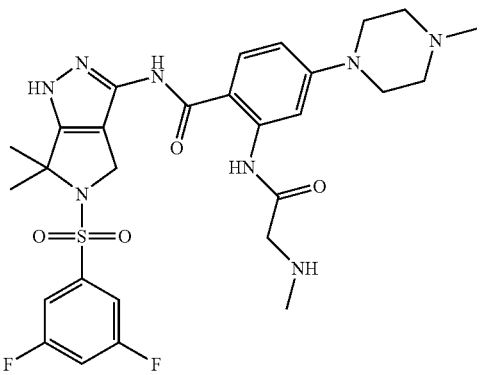 [SMILES: CNCC(=O)Nc1cc(N2CCN(C)CC2)ccc1C(=O)Nc1n[nH]c2c1CN(S(=O)(=O)c1cc(F)cc(F)c1)C2(C)C]

1H-NMR (400 MHz), δ (ppm, DMSO-$d_6$): 12.50, 12.22 (bs, 1H), 10.74 (bs, 1H), 8.28 (d, J2=2.56 Hz, 1H), 7.78 (m, bs, 1H), 7.66 (m, 1H), 7.58 (m, 2H), 7.28 (bs, 1H), 6.68 (bs, 2H), 4.61 (m, 2H), 3.27 (m, 4H), 3.23 (s, 2H), 2.45 (m, 4H), 2.35 (s, 3H), 2.24 (s, 3H), 1.68 (bs, 6H); mixture of tautomers.

Example 69

(S)-Pyrrolidine-2-carboxylic acid [2-[5-(3,5-difluoro-benzenesulfonyl)-6,6-dimethyl-1,4,5,6-tetrahydro-pyrrolo[3,4-c]pyrazol-3-ylcarbamoyl]-5-(4-methyl-piperazin-1-yl)-phenyl]-amide

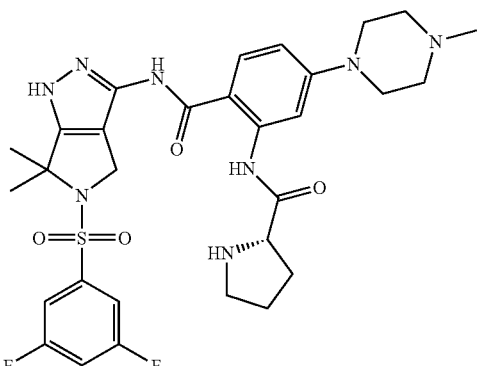

1H-NMR (400 MHz), δ (ppm, DMSO-$d_6$): 12.48 (bs, 1H), 12.18 (bs, 1H), 10.73 (bs, 1H), 8.26 (d, J2=2.56 Hz, 1H), 7.75 (m, 1H), 7.67 (m, 1H), 7.57 (m, 2H), 6.68 (m, 1H), 4.63-4.54 (m, 2H), 3.72 (m, 1H), 3.26 (m, 4H), 3.01-2.84 (m, 2H), 2.45 (m, 4H), 2.24 (s, 3H), 2.07 (m, 1H), 1.81-1.61 (m, 9H); mixture of tautomers.

We claim:

1. A compound represented by formula (I)

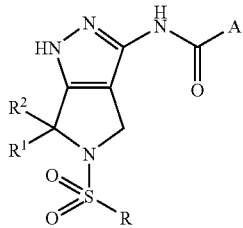

(I)

wherein:

R is aryl;

R¹ and R² are methyl;

A is selected from the group consisting of:

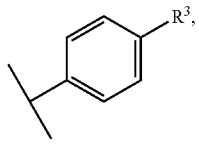

A0

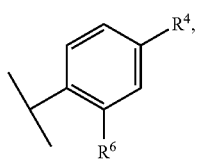

A2

R³ is heterocycloalkyl;

R⁴ is selected from the group consisting of NR⁸R⁹ and heterocycloalkyl;

R⁶ is selected from the group consisting of halogen and NHCOR¹¹;

R⁸ and R⁹, which can be the same or different, are each independently selected from the group consisting of hydrogen and (C₁-C₄)alkyl;

R¹¹ is selected from the group consisting of isopropyl, cyclobutyl and —CH₂N(CH₃)₂ or a pharmaceutically acceptable salt thereof.

2. A compound according to claim 1, wherein:

R is selected from the group consisting of phenyl, a 2-substituted-phenyl, a 3-substituted-phenyl, a 2,6-di-substituted-phenyl and a 3,5-di-substituted-phenyl;

A is selected from the group consisting of:

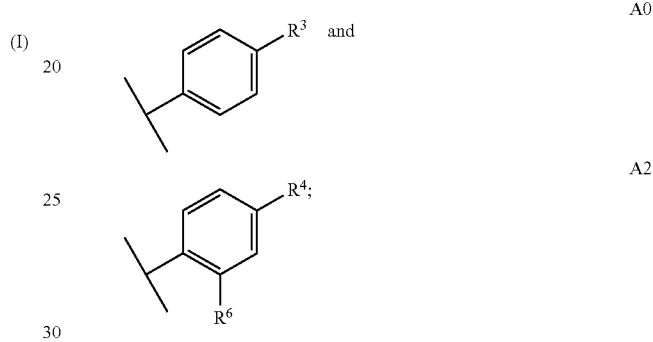

R¹ and R² are each methyl;

R³ is a six-membered heterocycloalkyl;

R⁴ is selected from the group consisting of NR⁸R⁹ and a six-membered heterocycloalkyl;

R⁶ is selected from the group consisting of halogen, and NHCOR¹¹;

R⁸ and R⁹, which can be the same or different, are each independently selected from the group consisting of hydrogen and (C₁-C₄)alkyl; and R¹¹ is selected from the group consisting of isopropyl, cyclobutyl and —CH₂N(CH₃)₂.

3. A compound according to claim 1, wherein:

R is selected from the group consisting of phenyl, a 3-substituted-phenyl and a 3,5-di-substituted-phenyl;

A is selected from the group consisting of:

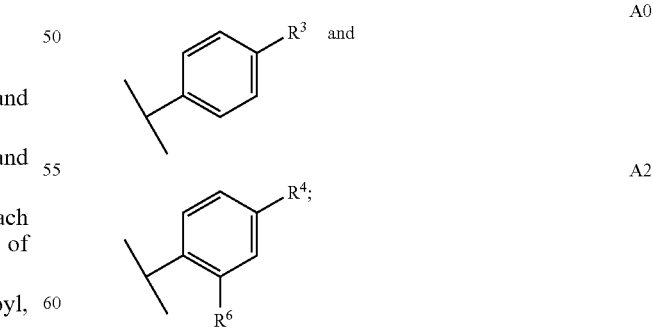

R¹ and R² are each methyl;

R³ is selected from the group consisting of morpholine and a substituted piperazine;

R⁴ is selected from the group consisting of NR⁸R⁹, morpholine and a substituted piperazine $R^6$ is selected from the group consisting of fluorine and $NHCOR^{11}$;

$R^8$ and $R^9$ are each methyl; and $R^{11}$ is selected from the group consisting of isopropyl, cyclobutyl and $-CH_2N(CH_3)_2$.

4. A pharmaceutical composition comprising an amount of the compound according to claim 1, or a pharmaceutically acceptable salt thereof, and a pharmaceutically acceptable carrier.

5. A compound according to claim 1 selected from the group consisting of:

N-(5-Benzenesulfonyl-6,6-dimethyl-1,4,5,6-tetrahydro-pyrrolo[3,4-c]pyrazol-3-yl)-4-piperazin-1-yl-benzamide;

N-(5-Benzenesulfonyl-6,6-dimethyl-1,4,5,6-tetrahydro-pyrrolo[3,4-c]pyrazol-3-yl)-4-(4-methyl-piperazin-1-yl)-benzamide;

N-(5-Benzenesulfonyl-6,6-dimethyl-1,4,5,6-tetrahydro-pyrrolo[3,4-c]pyrazol-3-yl)-4-morpholin-4-yl-benzamide;

N-[5-(2-Fluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

N-[5-(3-Fluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

N-[5-(3-Fluoro-benzenesulfonyl)-6,6-dimethyl-1,4,5,6-tetrahydro-pyrrolo[3,4-c]pyrazol-3-yl]-4-morpholin-4-yl-benzamide;

N-[5-(4-Fluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

N-[5-(3,4-Difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

N-[5-(3,5-Difluoro-benzenesulfonyl)-6,6-dimethyl-1,4,5,6-tetrahydro-pyrrolo[3,4-e]pyrazol-3-yl]-4-piperazin-1-yl-benzamide;

N-[5-(3,5-Difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

N-[5-(3,5-Difluoro-benzenesulfonyl)-6,6-dimethyl-1,4,5,6-tetrahydro-pyrrolo[3,4-e]pyrazol-3-yl]-4-(4-ethyl-piperazin-1-yl)-benzamide;

N-[5-(3,5-Difluoro-benzenesulfonyl)-6,6-dimethyl-1,4,5,6-tetrahydro-pyrrolo[3,4-c]pyrazol-3-yl]-4-(4-isopropyl-piperazin-1-yl)-benzamide;

4-(4-tert-Butyl-piperazin-1-yl)-N-[5-(3,5-difluoro-benzenesulfonyl)-6,6-dimethyl-1,4,5,6-tetrahydro-pyrrolo[3,4-c]pyrazol-3-yl]-benzamide;

4-(4-Cyclopropyl-piperazin-1-yl)-N-[5-(3,5-difluoro-benzenesulfonyl)-6,6-dimethyl-1,4,5,6-tetrahydro-pyrrolo[3,4-c]pyrazol-3-yl]-benzamide;

N-[5-(3,5-Difluoro-benzenesulfonyl)-6,6-dimethyl-1,4,5,6-tetrahydro-pyrrolo[3,4-c]pyrazol-3-yl]-4-morpholin-4-yl-benzamide;

N-[5-(3,5-Difluoro-benzenesulfonyl)-6,6-dimethyl-1,4,5,6-tetrahydro-pyrrolo[3,4-c]pyrazol-3-yl]-2-fluoro-4-(4-methyl-piperazin-1-yl)-benzamide;

N-[5-(3,5-Difluoro-benzenesulfonyl)-6,6-dimethyl-1,4,5,6-tetrahydro-pyrrolo[3,4-c]pyrazol-3-yl]-2-isobutyrylamino-4-(4-methyl-piperazin-1-yl)-benzamide;

2-(Cyclobutanecarbonyl-amino)-N-[5-(3,5-difluoro-benzenesulfonyl)-6,6-dimethyl-1,4,5,6-tetrahydro-pyrrolo[3,4-c]pyrazol-3-yl]-4-(4-methyl-piperazin-1-yl)-benzamide;

N-[5-(3,5-Difluoro-benzenesulfonyl)-6,6-dimethyl-1,4,5,6-tetrahydro-pyrrolo[3,4-c]pyrazol-3-yl]-2-(2-dimethylamino-acetylamino)-4-(4-methyl-piperazin-1-yl)-benzamide;

N-[5-(3,5-Difluoro-benzenesulfonyl)-6,6-dimethyl-1,4,5,6-tetrahydro-pyrrolo[3,4-c]pyrazol-3-yl]-2-(2-dimethylamino-acetylamino)-4-morpholin-4-yl-benzamide; and N-[5-(3,5-Difluoro-benzenesulfonyl)-6,6-dimethyl-1,4,5,6-tetrahydro-pyrrolo[3,4-c]pyrazol-3-yl]-4-dimethylamino-2-(2-dimethylamino-acetylamino)-benzamide.

\* \* \* \* \*

SEQUENCE LISTING

<160> NUMBER OF SEQ ID NOS: 4

<210> SEQ ID NO 1
<211> LENGTH: 33
<212> TYPE: DNA
<213> ORGANISM: Artificial
<220> FEATURE:
<223> OTHER INFORMATION: Forward primer

<400> SEQUENCE: 1
ctcggatcca gaaagagaaa taacagcagg ctg                                    33

<210> SEQ ID NO 2
<211> LENGTH: 36
<212> TYPE: DNA
<213> ORGANISM: Artificial
<220> FEATURE:
<223> OTHER INFORMATION: Reverse primer

<400> SEQUENCE: 2
ctcggatcct cagcaggtcg aagactgggg cagcgg                                 36

<210> SEQ ID NO 3
<211> LENGTH: 639
<212> TYPE: PRT
<213> ORGANISM: Artificial
<220> FEATURE:
<223> OTHER INFORMATION: Fusion protein

<400> SEQUENCE: 3

Met Gly Ser Pro Ile Leu Gly Tyr Trp Lys Ile Lys Gly Leu Val Gln
1               5                   10                  15

Pro Thr Arg Leu Leu Leu Glu Tyr Leu Glu Glu Lys Tyr Glu Glu His
            20                  25                  30

Leu Tyr Glu Arg Asp Glu Gly Asp Lys Trp Arg Asn Lys Lys Phe Glu
        35                  40                  45

Leu Gly Leu Glu Phe Pro Asn Leu Pro Tyr Tyr Ile Asp Gly Asp Val
    50                  55                  60

Lys Leu Thr Gln Ser Met Ala Ile Ile Arg Tyr Ile Ala Asp Lys His
65                  70                  75                  80

Asn Met Leu Gly Gly Cys Pro Lys Glu Arg Ala Glu Ile Ser Met Leu
                85                  90                  95

Glu Gly Ala Val Leu Asp Ile Arg Tyr Gly Val Ser Arg Ile Ala Tyr
            100                 105                 110

Ser Lys Asp Phe Glu Thr Leu Lys Val Asp Phe Leu Ser Lys Leu Pro
        115                 120                 125

Glu Met Leu Lys Met Phe Glu Asp Arg Leu Cys His Lys Thr Tyr Leu
    130                 135                 140

Asn Gly Asp His Val Thr His Pro Asp Phe Met Leu Tyr Asp Ala Leu
145                 150                 155                 160

Asp Val Val Leu Tyr Met Asp Pro Met Cys Leu Asp Ala Phe Pro Lys
                165                 170                 175

Leu Val Cys Phe Lys Lys Arg Ile Glu Ala Ile Pro Gln Ile Asp Lys
            180                 185                 190

Tyr Leu Lys Ser Ser Lys Tyr Ile Ala Trp Pro Leu Gln Gly Trp Gln
        195                 200                 205

Ala Thr Phe Gly Gly Gly Asp His Pro Pro Lys Ser Asp Leu Glu Val
    210                 215                 220

Leu Phe Gln Gly Pro Gly Ser Arg Lys Arg Asn Asn Ser Arg Leu Gly

```
            225                 230                 235                 240
        Asn Gly Val Leu Tyr Ala Ser Val Asn Pro Glu Tyr Phe Ser Ala Ala
                        245                 250                 255
        Asp Val Tyr Val Pro Asp Glu Trp Glu Val Ala Arg Glu Lys Ile Thr
                        260                 265                 270
        Met Ser Arg Glu Leu Gly Gln Gly Ser Phe Gly Met Val Tyr Glu Gly
                    275                 280                 285
        Val Ala Lys Gly Val Val Lys Asp Pro Glu Thr Arg Val Ala Ile
            290                 295                 300
        Lys Thr Val Asn Glu Ala Ala Ser Met Arg Glu Arg Ile Glu Phe Leu
        305                 310                 315                 320
        Asn Glu Ala Ser Val Met Lys Glu Phe Asn Cys His His Val Val Arg
                            325                 330                 335
        Leu Leu Gly Val Val Ser Gln Gly Gln Pro Thr Leu Val Ile Met Glu
                        340                 345                 350
        Leu Met Thr Arg Gly Asp Leu Lys Ser Tyr Leu Arg Ser Leu Arg Pro
                    355                 360                 365
        Glu Met Glu Asn Asn Pro Val Leu Ala Pro Pro Ser Leu Ser Lys Met
            370                 375                 380
        Ile Gln Met Ala Gly Glu Ile Ala Asp Gly Cys Ala Asn Leu Asn Ala
        385                 390                 395                 400
        Asn Lys Phe Val His Arg Asp Leu Ala Ala Arg Asn Cys Met Val Ala
                        405                 410                 415
        Glu Asp Phe Thr Val Lys Ile Gly Asp Phe Gly Met Thr Arg Asp Ile
                        420                 425                 430
        Tyr Glu Thr Asp Tyr Tyr Arg Lys Gly Gly Lys Gly Leu Leu Pro Val
                    435                 440                 445
        Arg Trp Met Ser Pro Glu Ser Leu Lys Asp Gly Val Phe Thr Thr Tyr
            450                 455                 460
        Ser Asp Val Trp Ser Phe Gly Val Val Leu Trp Glu Ile Ala Thr Leu
        465                 470                 475                 480
        Ala Glu Gln Pro Tyr Gln Gly Leu Ser Asn Glu Gln Val Leu Arg Phe
                        485                 490                 495
        Val Met Glu Gly Gly Leu Leu Asp Lys Pro Asp Asn Cys Pro Asp Met
                        500                 505                 510
        Leu Phe Glu Leu Met Arg Met Cys Trp Gln Tyr Asn Pro Lys Met Arg
                    515                 520                 525
        Pro Ser Phe Leu Glu Ile Ile Ser Ser Ile Lys Glu Glu Met Glu Pro
            530                 535                 540
        Gly Phe Arg Glu Val Ser Phe Tyr Tyr Ser Glu Glu Asn Lys Leu Pro
        545                 550                 555                 560
        Glu Pro Glu Glu Leu Asp Leu Glu Pro Glu Asn Met Glu Ser Val Pro
                        565                 570                 575
        Leu Asp Pro Ser Ala Ser Ser Ser Leu Pro Leu Pro Asp Arg His
                        580                 585                 590
        Ser Gly His Lys Ala Glu Asn Gly Pro Gly Pro Gly Val Leu Val Leu
                    595                 600                 605
        Arg Ala Ser Phe Asp Glu Arg Gln Pro Tyr Ala His Met Asn Gly Gly
            610                 615                 620
        Arg Lys Asn Glu Arg Ala Leu Pro Leu Pro Gln Ser Ser Thr Cys
        625                 630                 635

<210> SEQ ID NO 4
```

```
<211> LENGTH: 19
<212> TYPE: PRT
<213> ORGANISM: Artificial
<220> FEATURE:
<223> OTHER INFORMATION: Synthetic peptide

<400> SEQUENCE: 4

Lys Lys Lys Ser Pro Gly Glu Tyr Val Asn Ile Glu Phe Gly Gly Gly
1               5                   10                  15

Gly Gly Lys
```